(12) United States Patent
Lu et al.

(10) Patent No.: US 8,933,210 B2
(45) Date of Patent: Jan. 13, 2015

(54) LABEL-FREE FUNCTIONAL NUCLEIC ACID SENSORS FOR DETECTING TARGET AGENTS

(75) Inventors: Yi Lu, Champaign, IL (US); Yu Xiang, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 97 days.

(21) Appl. No.: 13/267,414

(22) Filed: Oct. 6, 2011

(65) Prior Publication Data
US 2012/0252128 A1    Oct. 4, 2012

Related U.S. Application Data

(60) Provisional application No. 61/404,673, filed on Oct. 6, 2010.

(51) Int. Cl.
C07H 21/02    (2006.01)
C07H 21/04    (2006.01)

(52) U.S. Cl.
USPC ............ 536/23.1; 435/6.1; 435/91.1; 436/73; 436/81; 436/82; 436/94; 536/24.3

(58) Field of Classification Search
USPC ......... 435/6, 91.1, 91.31, 6.1; 536/23.1, 24.5, 536/24.3; 436/73, 81, 82, 94
See application file for complete search history.

(56) References Cited

U.S. PATENT DOCUMENTS

| 7,192,708 B2 | 3/2007 | Lu et al. |
| 7,332,283 B2 | 2/2008 | Lu et al. |
| 7,485,419 B2 | 2/2009 | Lu et al. |
| 7,534,560 B2 | 5/2009 | Lu et al. |
| 7,612,185 B2 | 11/2009 | Lu et al. |
| 2006/0094026 A1 | 5/2006 | Lu et al. |
| 2007/0037171 A1 | 2/2007 | Lu et al. |

OTHER PUBLICATIONS

Xiang et al., Anal. Chem., vol. 82, pp. 4122-4129 (2010).*
Brown et al., "A Lead-Dependent DNAzyme with a Two-Step Mechanism," *Biochem.* 42:7152-7161, 2003.
Brown et al., "Biochemical Characterization of a Uranyl Ion-Specific DNAzyme," *ChemBioChem* 10:486-492, 2009.
Liu and Lu, "Adenosine-Dependent Assembly of Aptazyme-Functionalized Gold Nanoparticles and its Application as a Colorimetric Biosensor," *Anal. Chem* 76:1627-1632, 2004.
Liu and Lu, "Preparation of Aptamer-Linked Gold Nanoparticle Purple Aggregates for Colorimetric Sensing of Analytes," *Nat. Protoc.* 1:246-252, 2006.
Liu and Lu, "Fast Colorimetric Sensing of Adenosine and Cocaine Based on a General Sensor Design Involving Aptamers and Nanoparticles," *Angew. Chem. Int. Ed.* 45:90-94, 2006.
Nutiu and Li, "Structure-Switching Signaling Aptamers," *J. Am. Chem. Soc.* 125:4771-4778, 2003.
Nutiu and Li, "A DNA-Protein Nanoengine for 'On-Demand' Release and Precise Delivery of Molecules," *Angew. Chem. Int. Ed.* 44:5464-5467, 2005.
Xiang et al., "Abasic Site-Containing DNAzyme and Aptamer for Label-Free Fluorescent Detection of $Pb^{2+}$ and Adenosine with High Sensitivity, Selectivity, and Tunable Dynamic Range," *J. Am. Chem. Soc.* 131:15352-15357, 2009.
Xiang et al., "Label-Free Fluorescent Functional DNA Sensors Using Unmodified DNA: A Vacant Site Approach," *Anal. Chem.* 82:4122-4129, 2010.
Xu and Lu, "Label-Free Fluorescent Aptamer Sensor Based on Regulation of Malachite Green Fluorescence," *Anal. Chem.* 82:574-578, 2010.

\* cited by examiner

*Primary Examiner* — Jane Zara
(74) *Attorney, Agent, or Firm* — Klarquist Sparkman, LLP

(57) ABSTRACT

A general methodology to design label-free fluorescent functional nucleic acid sensors using a vacant site approach and an abasic site approach is described. In one example, a method for designing label-free fluorescent functional nucleic acid sensors (e.g., those that include a DNAzyme, aptamer or aptazyme) that have a tunable dynamic range through the introduction of an abasic site (e.g., dSpacer) or a vacant site into the functional nucleic acids. Also provided is a general method for designing label-free fluorescent aptamer sensors based on the regulation of malachite green (MG) fluorescence. A general method for designing label-free fluorescent catalytic and molecular beacons (CAMBs) is also provided. The methods demonstrated here can be used to design many other label-free fluorescent sensors to detect a wide range of analytes. Sensors and methods of using the disclosed sensors are also provided.

19 Claims, 41 Drawing Sheets

FIG. 1A
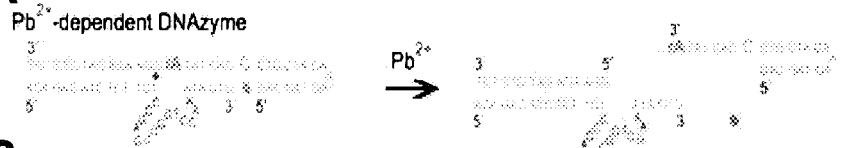
FIG. 1B
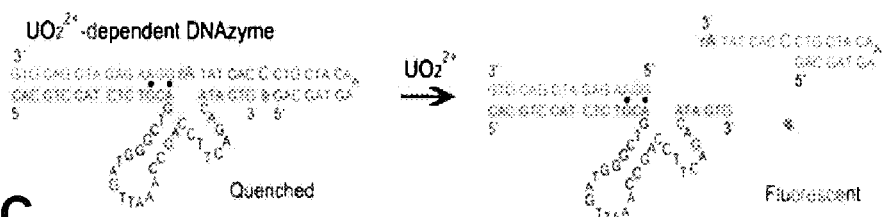
FIG. 1C
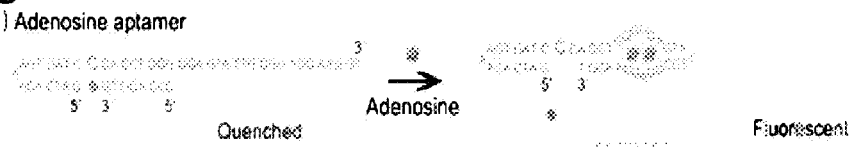
FIG. 1D
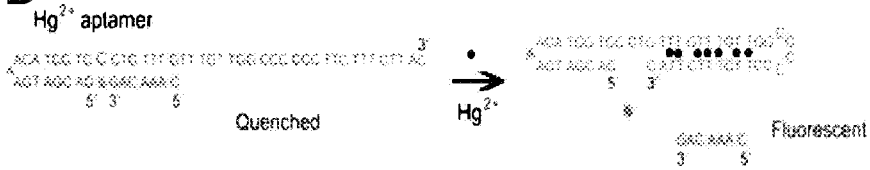
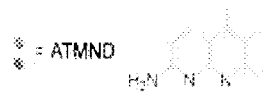
FIG. 1E
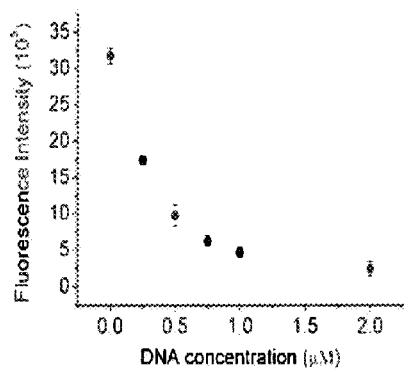

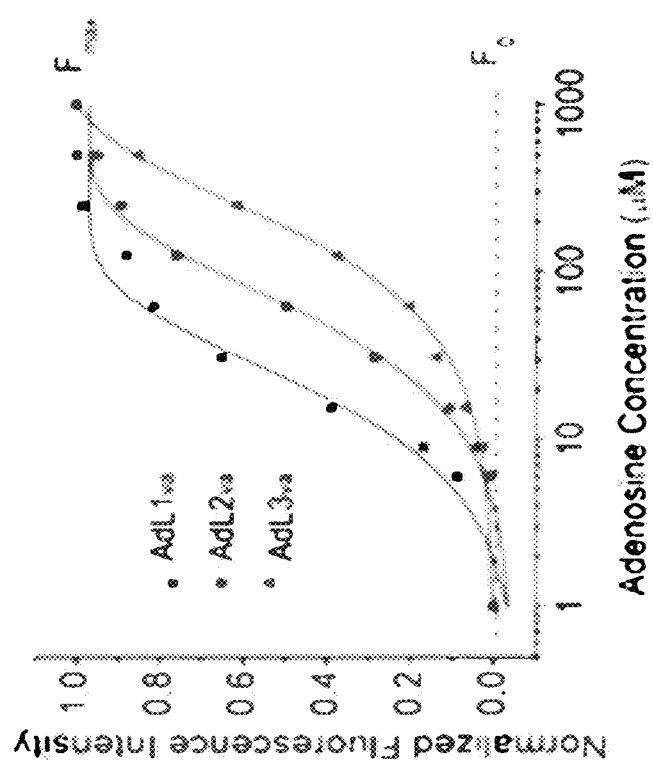
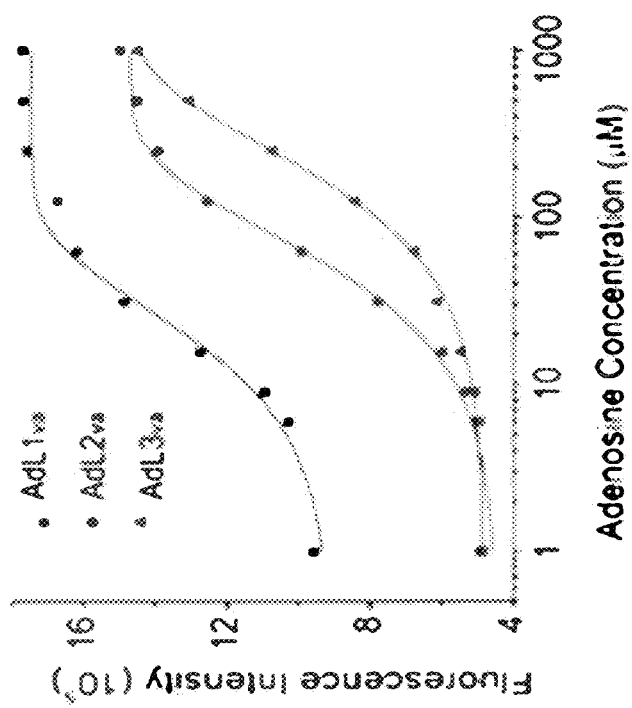
FIG. 7A
FIG. 7B

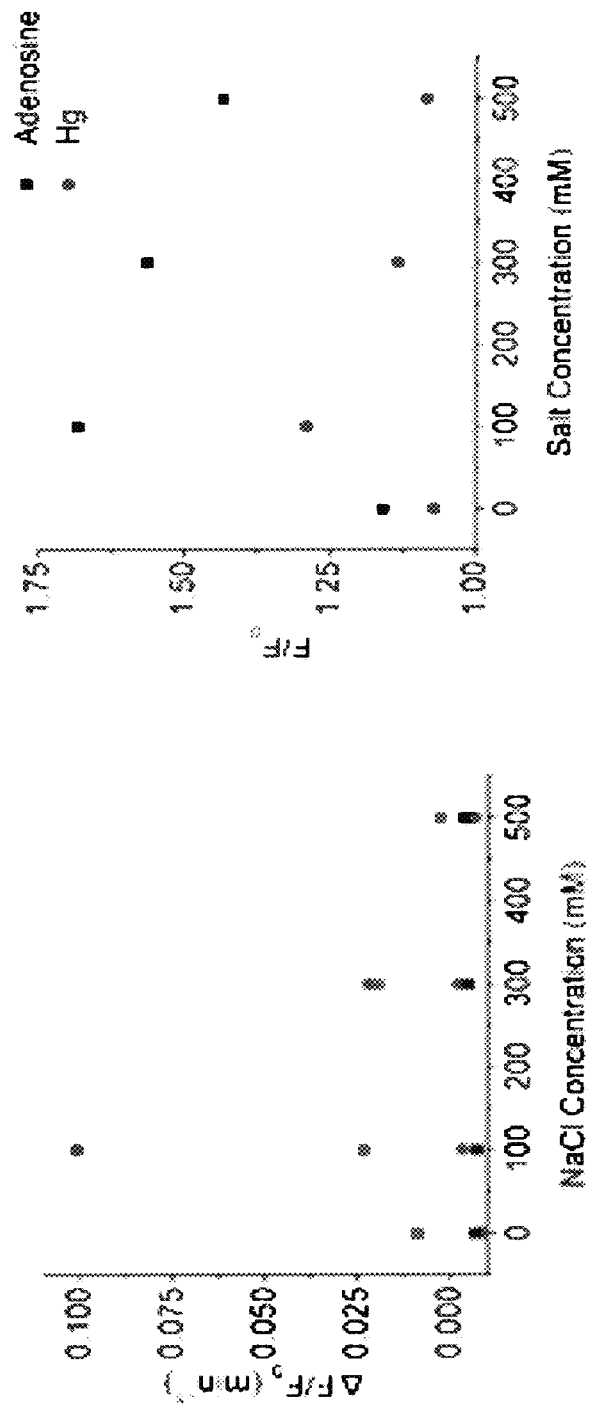

FIG. 9A          FIG. 9B
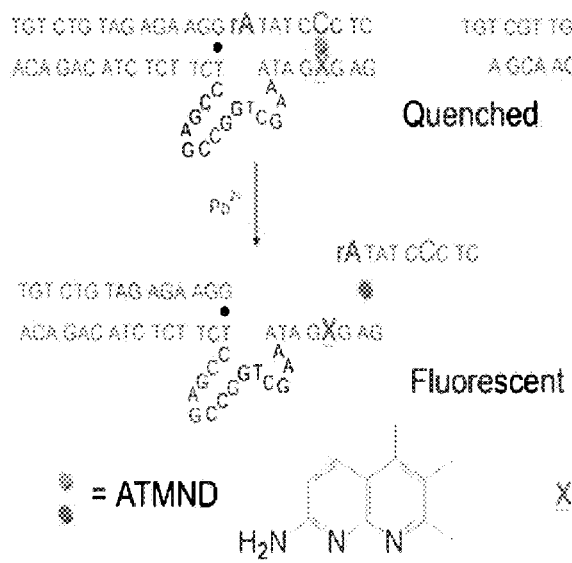
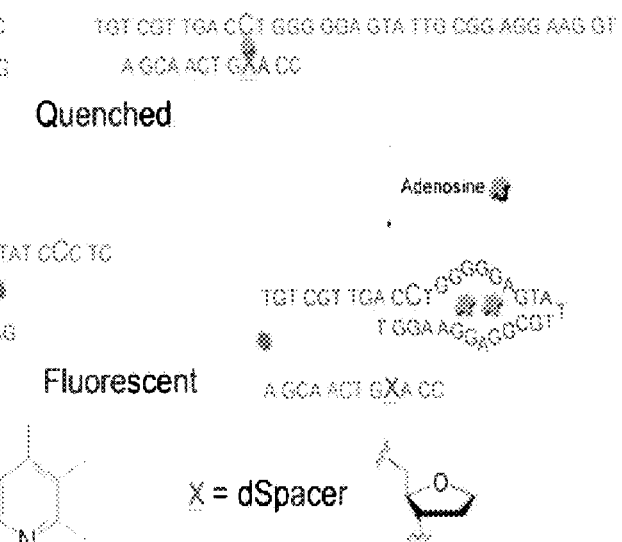
FIG. 9C          FIG. 9D
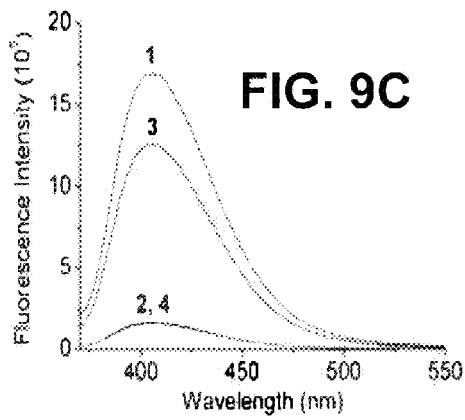
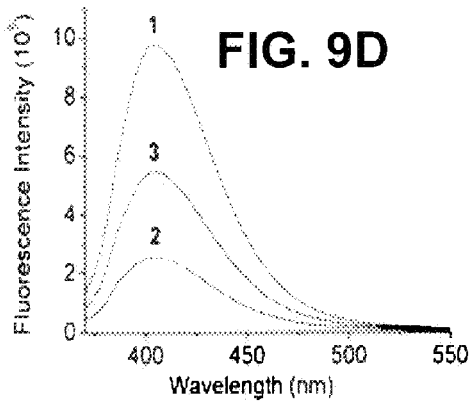

FIG. 9E
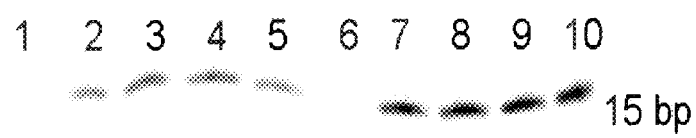
FIG. 9F  FIG. 9G
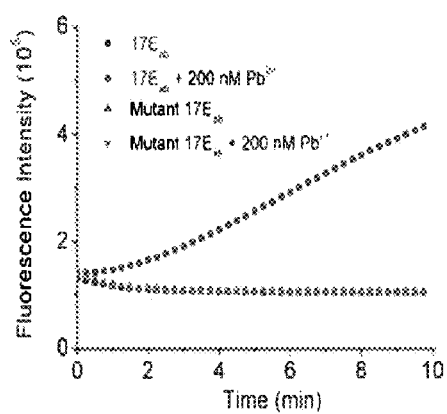
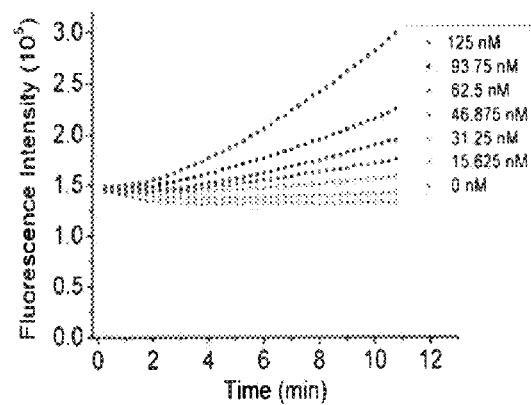

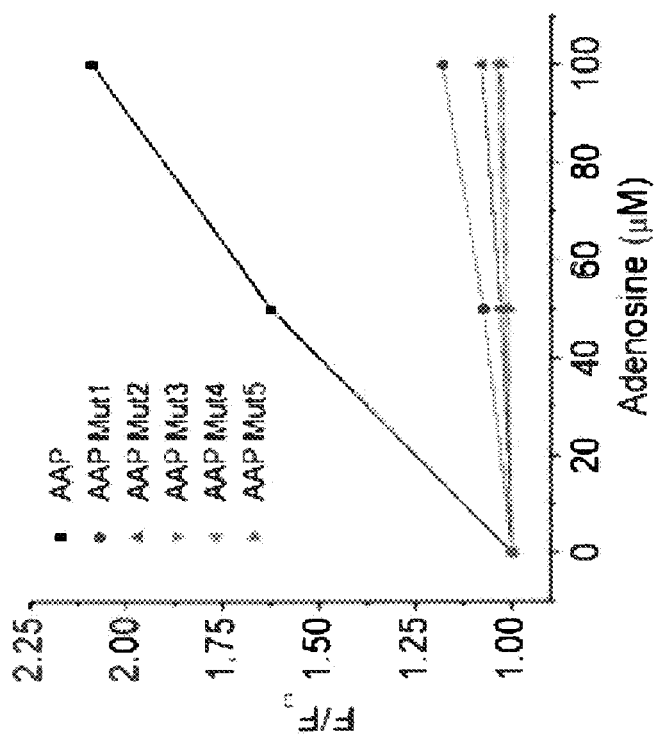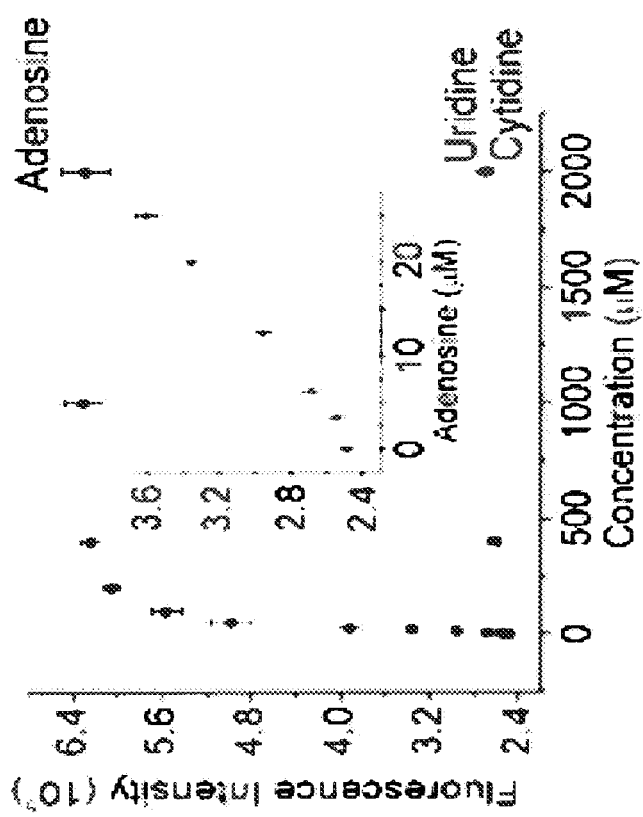
FIG. 13A
FIG. 13B

FIG. 16A  FIG. 16B
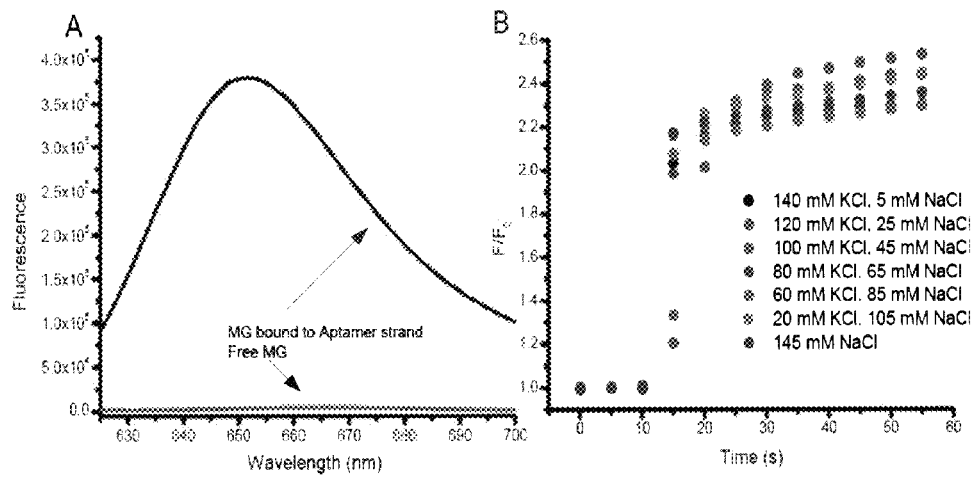
FIG. 17
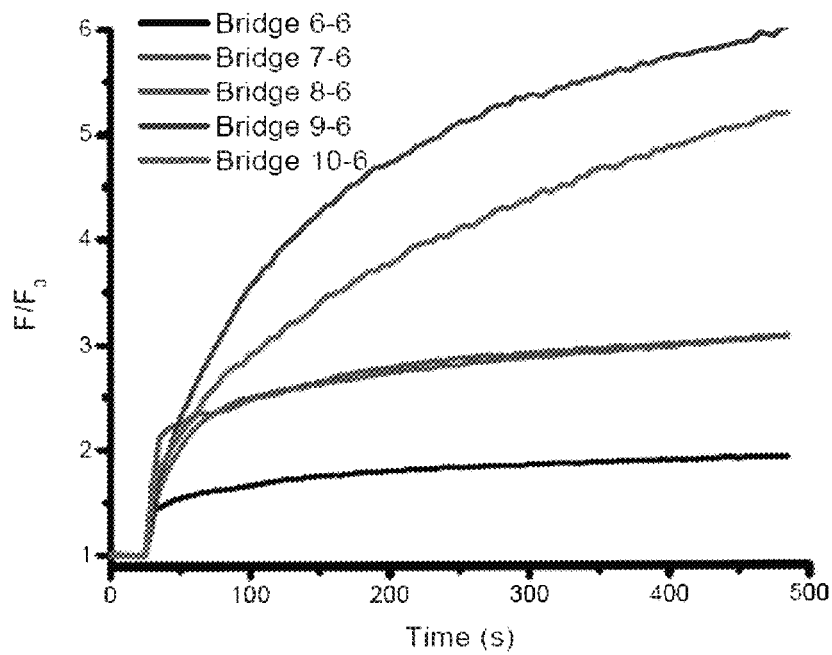

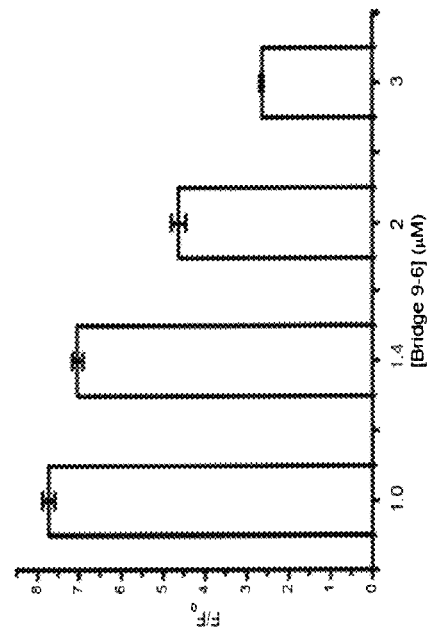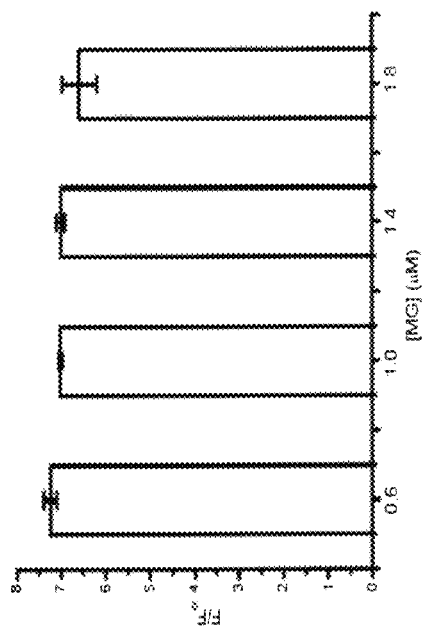

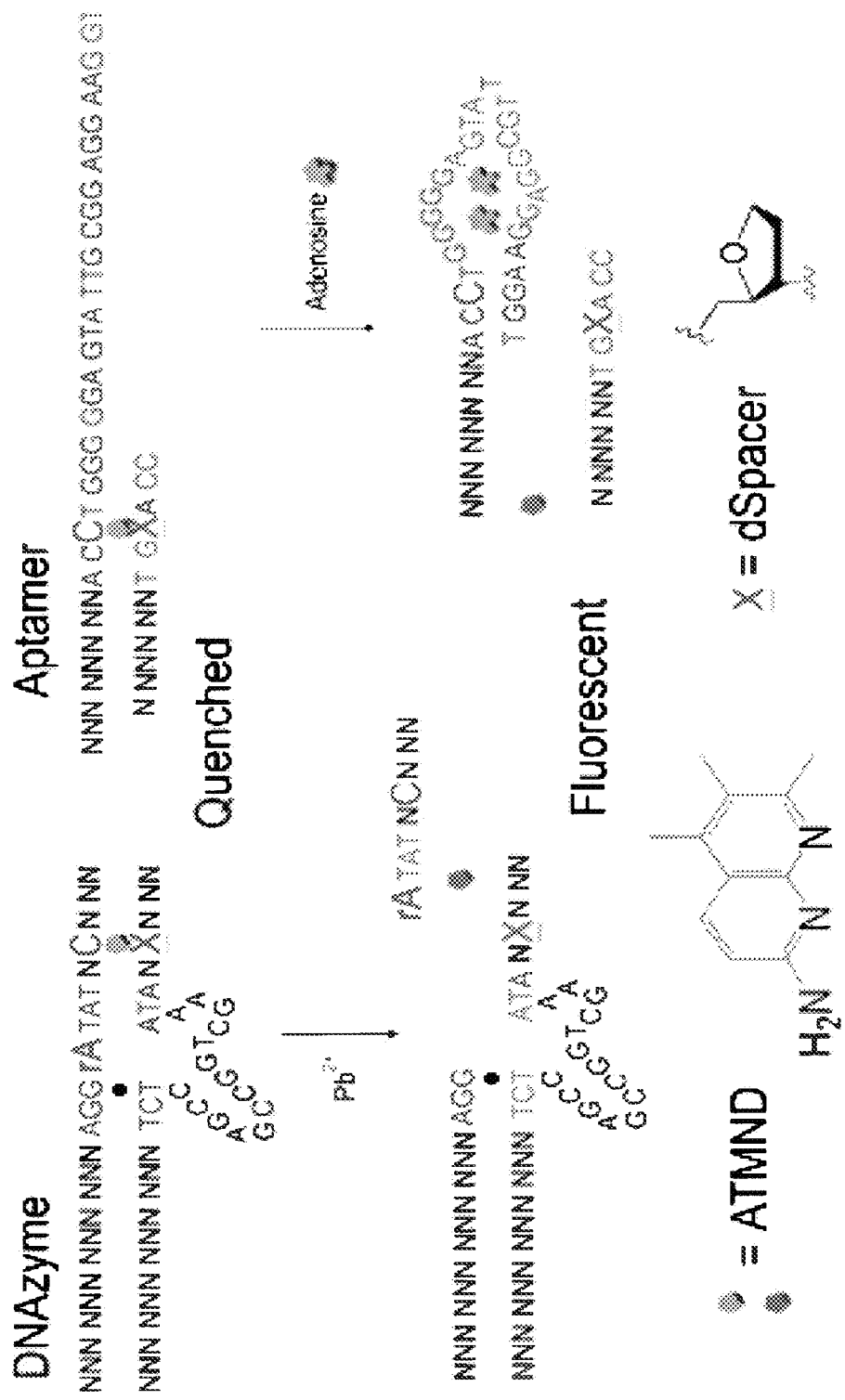

FIG. 22
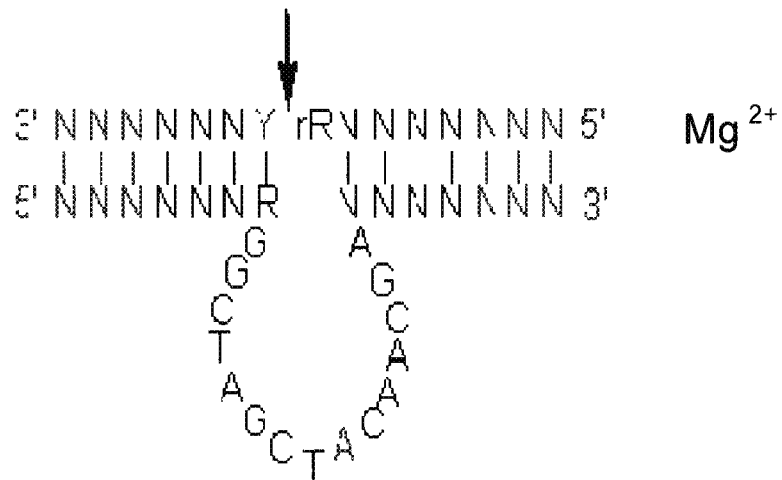
Mg²⁺
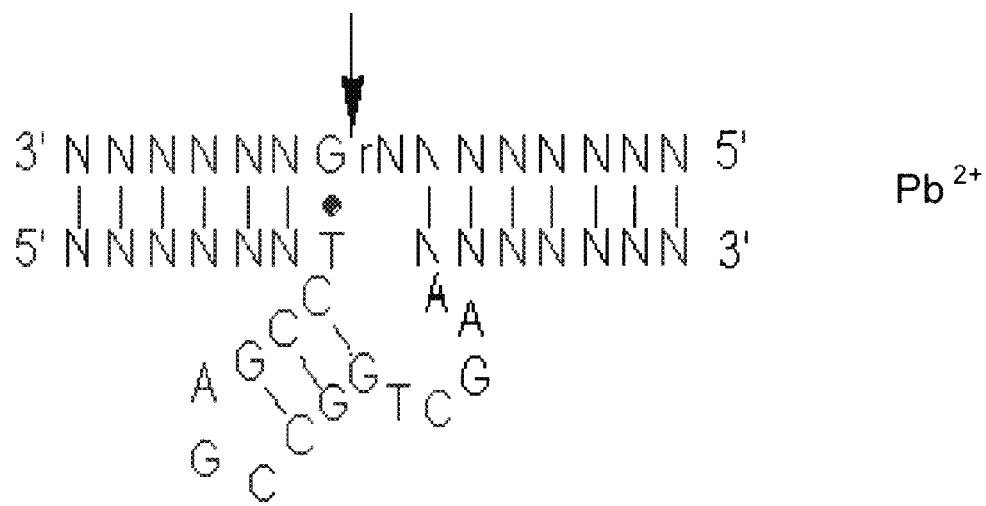
Pb²⁺
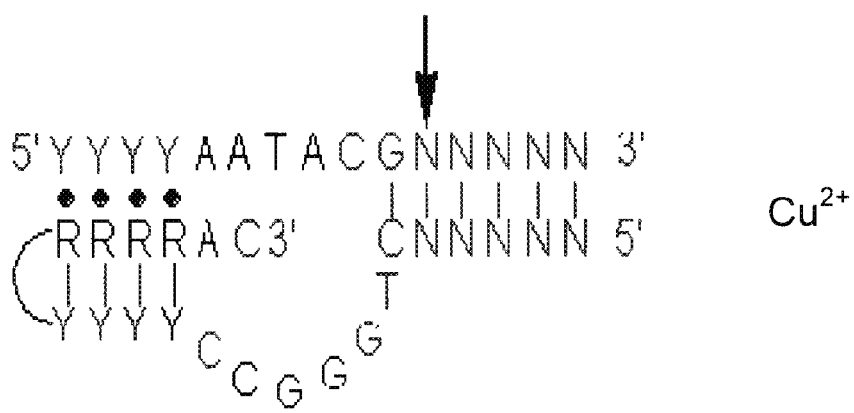
Cu²⁺

FIG. 23
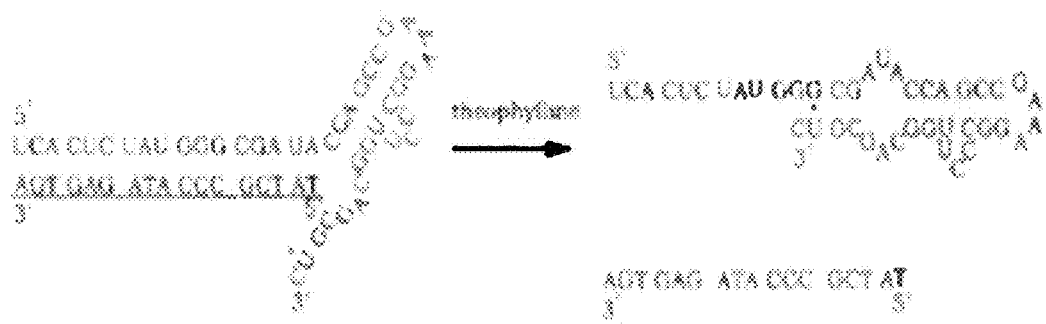
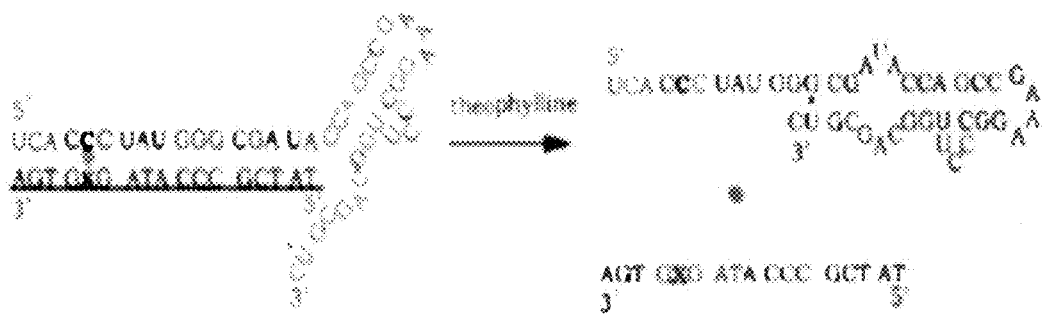
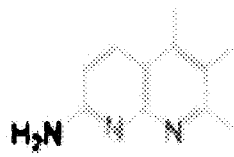

LABEL-FREE FUNCTIONAL NUCLEIC ACID SENSORS FOR DETECTING TARGET AGENTS

CROSS-REFERENCE TO RELATED APPLICATION

This application claims priority to U.S. Provisional Application No. 61/404,673 filed Oct. 6, 2010, herein incorporated by reference.

ACKNOWLEDGMENT OF GOVERNMENT SUPPORT

This invention was made with government support under DE-FG02-08ER64568 awarded by the Department of Energy, under ES16865 awarded by The National Institutes of Health, and CTS-0120978 and DMI-0328162 awarded by the National Science Foundation. The government has certain rights in the invention.

FIELD

This application relates to label-free nucleic acid sensor molecules (such as catalytic nucleic acids and aptamers), kits containing such sensors, as well as methods for using such to detect target agents.

BACKGROUND

Driven by their impact on human health, the detection and quantification of metal ions and organic molecules in biological and environmental systems has attracted intense attention recently (Nolan and Lippard, *Chem. Rev.* 2008, 108, 3443-3480; Que et al., *Chem. Rev.* 2008, 108, 1517-1549). Although instrumental analysis is the routine method of probing these systems, the cost and complicated operation of the required instruments limit their usefulness in carrying out the on-site and real-time detection that is crucial for these systems. To overcome these limitations, a number of highly sensitive and selective sensors have been developed that are portable and offer rapid quantification (Burdette et al., *J. Am. Chem. Soc.* 2001, 123, 7831-7841; Chang, et al., *Proc. Nat. Acad. Sci. U.S.A.* 2004, 101, 1129-1134; Chen, P.; He, C. *J. Am. Chem. Soc.* 2004, 126, 728-729; Yoon et al., *J. Am. Chem. Soc.* 2005, 127, 16030-16031; Wu et al., *Anal. Chem.* 2007, 79, 2933-2939; Zhang et al., *J. Am. Chem. Soc.* 2007, 129, 15448-15449; Chen and He *Curr. Opin. Chem. Biol.* 2008, 12, 214-221; Xue et al., *J. Am. Chem. Soc.* 2008, 130, 3244; Wong et al., *J. Am. Chem. Soc.* 2009, 131, 7142-7152; Xue et al., *J. Am. Chem. Soc.* 2009, 131, 11668; Xu et al., *Angew. Chem., Int. Ed.* 2009, 48, 6849-6852; Wu et al., *J. Am. Chem. Soc.* 2009, 131, 12325-12332). While these results are promising, a more general platform must be developed so that one strategy can be used to select a sensor for any of a wide range of analytes.

One general sensor platform is based on functional nucleic acids (FNAs). These functional molecules (such as DNA or RNA molecules) have been identified through a combinatorial method known as in vitro selection (Breaker et al., *Chem. Biol.* 1994, 1, 223-229; Robertson and Joyce, *Nature* 1990, 344:467) or Systematic Evolution of Ligands by Exponential Enrichment (SELEX) (Ellington et al., *Nature* 1990, 346, 818-822; Tuerk and Gold, *Science* 1990, 249, 505) from random nucleic acid libraries containing $10^{14}$ or more sequences. The catalytic nucleic acids (also called DNAzymes, RNAzymes, deoxyribozymes, ribozymes, RNA enzymes or DNA enzymes), aptazymes, and aptamers selected through these methods are reported to exhibit catalytic activity and binding affinity, respectively in the presence of a diverse number of targets, which range from metal ions and small organic molecules to macromolecules, proteins, nucleic acids, and even viruses and cells (Cuenoud et al., *Nature* 1995, 375, 611-614; Carmi et al., *Chem. Biol.* 1996, 3, 1039-1046; Santoro et al., *J. Am. Chem. Soc.* 2000, 122, 2433-2439; Li et al., *Nucleic Acids Res.* 2000, 28, 481-488; Li and Lu, *J. Am. Chem. Soc.* 2000, 122, 10466-10467; Bruesehoff et al., *Comb. Chem. High Throughput Screening* 2002, 5, 327-335; Mei et al., *J. Am. Chem. Soc.* 2003, 125, 412-420; Wang and Silverman, *J. Am. Chem. Soc.* 2003, 125, 6880-6881; Lee et al., *Nucleic Acids Res.* 2004, 32, D95-D100; Navani and Li. *Curr. Opin. Chem. Biol.* 2006, 10, 272-281; Liu et al., *Proc. Nat. Acad. Sci. U.S.A.* 2007, 104, 2056-2061; Song et al., *TrAC, Trends Anal. Chem.* 2008, 27, 108-117; Liu et al., *Chem. Rev.* 2009, 109, 1948-1998; Robertson and Joyce, *Nature* 1990, 344:467; Breaker and Joyce, *Chem. Biol.* 1994, 1:223; Tuerk and Gold, *Science* 1990, 249:505; Ellington et al., *Nature* 1990, 346:818; Huizenga and Szostak, *Biochemistry* 1995, 34:656; Nutiu and Li, *J. Am. Chem. Soc.* 2003, 125:4771; Santoro et al., *J. Am. Chem. Soc.* 2000, 122, 2433; Li et al., *Acc. Chem. Res.* 2010, 43:631). Unlike other molecules used for sensor design, functional nucleic acids have predictable secondary structures that can be easily functionalized them with fluorophores, chromophores or electrochemical tags, making it possible to transform the specific interactions between functional nucleic acids and their targets into detectable signals (Navani and Li, *Curr. Opin. Chem. Biol.* 2006, 10, 272-28; Song et al., *TrAC, Trends Anal. Chem.* 2008, 27, 108-117; Liu et al., *Chem. Rev.* 2009, 109, 1948-1998; Rajendran and Ellington, *Comb. Chem. High Throughput Screening* 2002, 5, 263-270; Lu, *Chem. Eur. J.* 2002, 8, 4588-4596; Willner and Zayats, *Angew. Chem., Int. Ed.* 2007, 46, 6408-6418; Willner et al., *Chem. Soc. Rev.* 2008, 37, 1153-1165; Li and Lu, *Functional;* Springer: New York, 2009; Xiao et al., *Angew. Chem., Int. Ed.* 2005, 44, 5456-5459; Xiao et al., *J. Am. Chem. Soc.* 2005, 127, 17990-17991; Baker et al., *J. Am. Chem. Soc.* 2006, 128, 3138-3139; Zayats et al., *J. Am. Chem. Soc.* 2006, 128, 13666-13667; Shlyahovsky et al., *J. Am. Chem. Soc.* 2007, 129, 3814; Zuo et al., *J. Am. Chem. Soc.* 2007, 129, 1042-104; He, S. J.; Li, D.; Zhu et al., *Chem. Com.,* Zhang, et al., *Small* 2008, 4, 1196-1200; Schlosser and Li, *Chem. Biol.* 2009, 16, 311-322; Swensen et al., *J. Am. Chem. Soc.* 2009, 131, 4262-4266; Zuo et al., *J. Am. Chem. Soc.* 2009, 131, 6944; Freeman et al., *Angew. Chem., Int. Ed.* 2009, 48, 7818-7821; Freeman et al., *J. Am. Chem. Soc.* 2009, 131, 5028). Therefore, numerous functional DNA sensors, such as fluorescent (Shlyahovsky et al., *J. Am. Chem. Soc.* 2007, 129, 3814; Freeman et al., *Angew. Chem., Int. Ed.* 2009, 48, 7818-7821; Freeman et al., *J. Am. Chem. Soc.* 2009, 131, 5028; Nutiu, R.; Li, Y. *Chem. Eur. J.* 2004, 10, 1868-1876; Cho et al., *Top. Fluoresc. Spectrosc.* 2005, 10, 127-155; Cao et al., *Curr. Proteomics* 2005, 2, 31-40; Liu and Lu, *Methods Mol. Biol.* 2006, 335, 275-288), colorimetric (Liu and Lu, *J. Am. Chem. Soc.* 2003, 125, 6642-6643; Pavlov et al., *J. Am. Chem. Soc.* 2004, 126, 11768-11769; Huang et al., *Anal. Chem.* 2005, 77, 5735-5741; Liu and Lu, *Angew. Chem., Int. Ed.* 2006, 45, 90-94; Lee et al., *Angew. Chem., Int. Ed.* 2007, 46, 4093-4096; Lee et al., *J. Am. Chem. Soc.* 2008, 130, 14217-14226; Wang, Z et al., *Adv. Mater.* 2008, 20, 3263-3267; Zhao et al., *Small* 2008, 4, 810-816), and electrochemical (Willner, I.; Zayats, M. *Angew. Chem., Int. Ed.* 2007, 46, 6408-6418; Zayats et al., *J. Am. Chem. Soc.* 2006, 128, 13666-13667; Xiao et al., *J. Am. Chem. Soc.* 2007, 129, 262-263) sensors based on this platform, have been developed. Among them, fluorescent sensors are particularly interesting because of their high sensitivity, simple instrumentation, and reproducible quantification.

Most fluorescent functional DNA sensors require covalent coupling of a fluorophore or a quencher to either the end, or the internal site or the 3'- or 5'-end of a DNA strand. The interaction between a functional DNA and its target induces the separation of the fluorophore and the quencher, causing an observable increase in fluorescence (Nutiu and Li, Chem. Eur. J. 2004, 10, 1868-1876; Cho et al., Top. Fluoresc. Spectrosc. 2005, 10, 127-155; Cao et al., Curr. Proteomics 2005, 2, 31-40). However, DNA labeling can be complicated, expensive, and intrusive. The label might interfere with a functional DNA as it interacts with its targets (Jiang et al., Anal. Chem. 2004, 76, 5230-5235; Wang et al., Anal. Chem. 2005, 77, 3542-3546). In addition, the label can make it difficult to introduce a labeled DNA into a biological system.

To overcome these limitations, label-free fluorescent sensors based on functional DNA have been developed using intercalating dyes (Joseph et al., Biospectroscopy 1996, 2, 173-183; Li, B.; Wei, H.; Dong, S. Chem. Commun. 2007, 73-75; Wang, Y.; Liu, B. Analyst 2008, 133, 1593-1598), malachite green (Babendure et al., J. Am. Chem. Soc. 2003, 125, 14716-14717; Stojanovic et al., J. Am. Chem. Soc. 2004, 126, 9266-9270), and abasic sites (Xu et al., Chem. Commun. 2009, 6445-6447; Xu et al., Chem. Eur. J. 2009, 15, 10375-10378; Xiang et al., J. Am. Chem. Soc. 2009, 131, 15352-15357).

SUMMARY

Provided herein is a general method for designing label-free fluorescent functional nucleic acid sensors, for example using unmodified nucleic acids containing an abasic site (e.g., dSpacer) or a vacant site that strongly binds an extrinsic fluorophore (such as 2-amino-5,6,7-trimethyl-1,8-naphthyridine; ATMND), and application of this approach to the rational design of fluorescent sensors. To demonstrate the generality of this approach, targets detectable by DNAzymes ($Pb^{2+}$ and $UO_2^{2+}$), targets detectable by aptamers (adenosine, theophylline, and $Hg^{2+}$), and targets detectable by aptazymes (adenosine) are exemplified herein. Based on this teaching, one skilled in the art will appreciate that other functional nucleic acid molecules can be similarly modified, such as ribozymes and RNA aptamers. These sensors exhibit high sensitivity and selectivity toward their targets.

In some examples, such sensors include a catalytic nucleic acid molecule (e.g., DNAzyme or ribozyme) specific for a target agent comprising an enzyme nucleic acid strand and a substrate nucleic acid strand. The enzyme nucleic acid strand includes a 3'-end and a 5'-end and an active site specific for a target agent. The substrate nucleic acid strand includes a 3'-end and a 5'-end. In addition, the substrate nucleic acid strand includes nucleotides at the 5'-end of the substrate nucleic acid strand that permit formation of a loop at the 5'-end of the substrate nucleic acid strand. The substrate nucleic acid strand hybridizes with the enzyme nucleic acid strand, thereby forming a vacant site between the 3'-end of the enzyme nucleic acid strand and the 5'-end of the substrate nucleic acid strand, wherein the vacant site is opposite to a cytosine present in the substrate nucleic acid strand.

In yet other examples, such sensors include an aptamer specific for a target agent having a 3'-end and a 5'-end; a first nucleic acid molecule having a 3'-end and a 5'-end, wherein the 5'-end of the aptamer is attached to the 3'-end of the first nucleic acid molecule, wherein the 3'-end of the first nucleic acid has the nucleotide sequence NCN, wherein N is any nucleotide, and wherein the 5'-end of the first nucleic acid molecule forms a loop; and a second nucleic acid molecule having a 3'-end and a 5'-end, wherein the second nucleic acid molecule is hybridized to the 5'-end of the aptamer, thereby forming a vacant site between the 5'-end of the first nucleic acid molecule and the 3'-end of the second nucleic acid molecule, wherein the vacant site is opposite to the cytosine of the NCN sequence of the first nucleic acid molecule.

Also provided is a general method for designing label-free fluorescent catalytic nucleic acid molecule (e.g., DNAzyme or ribozyme) and aptamer sensors that exhibit a tunable dynamic range through the introduction of an abasic site (e.g., dSpacer) into the functional nucleic acid molecule duplexes, and application of this approach to the rational design of fluorescent sensors. Based on this teaching, one skilled in the art will appreciate that other functional nucleic acid molecules can be similarly modified, such as ribozymes and RNA aptamers. To demonstrate the generality of this approach, a DNAzyme capable of detecting $Pb^{2+}$ and an aptamer capable of detecting adenosine are exemplified herein. These sensors exhibit high sensitivity and selectivity toward their targets. In some examples, such sensors include a catalytic nucleic acid molecule (e.g., DNAzyme or ribozyme) specific for a target agent comprising an enzyme nucleic acid strand and a substrate nucleic acid strand. The enzyme nucleic acid strand includes a 5'-end and a 3'-end and an active site specific for a target agent. The substrate nucleic acid strand includes a 3'-end and a 5'-end and a cytosine 2 to 6 nucleotides from the 5'-end of the substrate nucleic acid strand. A nucleotide 2 to 6 nucleotides from the 3'-end of the enzyme nucleic acid strand is replaced by an abasic site. The substrate nucleic acid strand hybridizes with the enzyme nucleic acid strand, resulting in the abasic site being opposite to the cytosine 2 to 6 nucleotides from the 5'-end of the substrate nucleic acid strand. In yet other examples, the sensor includes an aptamer specific for a target agent having a 3'-end and a 5'-end; a first nucleic acid molecule having at least four nucleotides attached to the 3'-end of the aptamer; and a second nucleic acid molecule having a 5'-end and a 3'-end and an abasic site, wherein second nucleic acid molecule has complementarity to the aptamer and to the first nucleic acid molecule, wherein the second nucleic acid molecule is hybridized to the aptamer and the first nucleic acid molecule the abasic site is opposite to a cytosine in the aptamer or first nucleic acid molecule.

Also provided is a general method for designing label-free fluorescent aptamer sensors based on the regulation of malachite green (MG) fluorescence, and application of this approach to the rational design of fluorescent sensors. To demonstrate the generality of this approach, an aptamer that can detect adenosine is exemplified herein. In one example, the sensor includes an aptamer specific for a target agent; a malachite green RNA aptamer, wherein the malachite green RNA aptamer is linked to the aptamer specific for the target agent; and a bridging nucleic acid strand, wherein the bridging strand is complementary to consecutive nucleotides present in the aptamer specific for the target and the MG RNA aptamer. The sensor can also include MG in solution with the nucleic acid, such that MG can bind to the MG aptamer strand of the sensor in the presence of the target agent binding to the aptamer specific for the target agent. Upon hybridization of the bridging nucleic acid strand to the aptamer specific for the target and the MG RNA aptamer, a stable complex is formed preventing the MG aptamer strand from binding MG present in the solution if there is no target agent is present.

Also provided is a general method for designing label-free catalytic and molecular beacons (CAMBs) that include an abasic site or a vacant site, and application of this approach to the rational design of label-free sensors. Based on this teaching, one skilled in the art will appreciate that other functional nucleic acid molecules can be similarly modified, such as ribozymes and RNA aptamers. To demonstrate the generality of this approach, FNA sensors using dSpacer-containing molecular beacons (MBs) as DNA substrates for detecting $Pb^{2+}$ and adenosine with high selectivity and sensitivity are exemplified herein. In some examples, such sensors include a catalytic nucleic acid molecule (e.g., DNAzyme, ribozyme, or aptazyme) specific for a target agent comprising an enzyme nucleic acid strand and a substrate nucleic acid strand. The enzyme nucleic acid strand includes a 5'-end and a 3'-end and an active site specific for a target agent. The substrate nucleic acid strand includes a 3'-end and a 5'-end and a cytosine 2 to 6 nucleotides from the 3'-end (or 5'-end) of the substrate nucleic acid strand. A nucleotide 2 to 6 nucleotides from the other end of the substrate nucleic acid strand (5'-end if the cytosine is 2 to 6 nucleotides from the 3'-end or the 3'-end if the cytosine is 2 to 6 nucleotides from the 5'-end) is replaced by an abasic site. The substrate nucleic acid strand hybridizes with the enzyme nucleic acid strand, resulting in the substrate nucleic acid strand forming a molecular beacon comprising a stem region, wherein the stem region includes the abasic site, wherein the abasic site is opposite to the cytosine 2 to 6 nucleotides from the 3'-end (or 5'-end) of the substrate nucleic acid strand.

The disclosure also provides solids supports, such as a bead or a membrane, that include one or more of the disclosed sensors.

Provided herein are kits that include one or more of the disclosed sensors, such as a kit that includes one or more sensors disclsoed herein and other materials, such as one or more of a buffer, a chart for correlating detected fluorescence and amount of target agent present, or a test agent.

Also provided herien are methods of using the disclosed sensors to detect a target agent. In one example the method includes contacting one or more sensors provided herein with a sample under conditions sufficient to allow the target agent in the sample to bind to the sensor resulting in cleavage of the sensor or a conformational change of the sensor; and detecting fluorescence, wherein detection of fluorescence indicates the presence of the target agent in the sample, and an absence of detected fluorescence indicates the absence of the target agent in the sample. For example, the sensors can be used to detect a target agent, such as a heavy metal, microbe, cytokine, hormone, cell, recreational drug, or toxin.

The foregoing and other objects and features of the disclosure will become more apparent from the following detailed description, which proceeds with reference to the accompanying figures.

BRIEF DESCRIPTION OF THE DRAWINGS

FIGS. 1A-1D are schematic drawings showing fluorescence enhancement response of the functional DNA sensors specific to (A) $Pb^{2+}$ (SEQ ID NOS: 1 and 2), (B) $UO_2^{2+}$ (SEQ ID NOS: 12 and 13), (C) adenosine (SEQ ID NOS: 5 and 9), and (D) $Hg^{2+}$ (SEQ ID NOS: 14 and 15) using unmodified DNA via a vacant site approach.

FIG. 1E is a graph showing the fluorescence titration of 0.75 µM ATMND with different amounts of $17S_{va}/17E_{va}$ duplex containing a vacant site in buffer A. The binding constant $K_a$ is calculated to be more than $10^6$ $M^{-1}$ according to the 1:1 binding mode, and the fluorescence intensity for each data point was found to be stable at least in one week (within 10% derivation).

FIGS. 7A and B are graphs showing the (a) tuning the dynamic range of adenosine detection for ATMND/$AdAP_{va}$/$AdL1_{va}$~AdL3va and a (b) figure with normalized fluorescence change. Condition: 10 mM HEPES pH 7.0, 100 mM NaCl and 1 mM EDTA at 5° C. $\lambda_{ex}/\lambda_{em}$=358/405 nm.

FIGS. 9A-D provide a schematic illustration of label-free fluorescent detection of (A) Pb$^{2+}$ (SEQ ID NOS: 16 and 18) and (B) and adenosine (SEQ ID NOS: 19 and 20), and the fluorescence emission spectra of ATMND in the absence and presence of 17E$_{ab}$-17S(C) and APP-L1$_{ab}$ (D) for Pb$^{2+}$ and adenosine detection, respectively. The fluorescent spectra in (C) were collected in buffer A (25 mM HEPES pH 7.0 and 100 mM NaCl). 1: ATMND (1 μM); 2: ATMND (1 μM), 17E$_{ab}$ (2.14 μM) and 17S (1.02 μM); 3: ATMND (1 μM), 17E$_{ab}$ (2.14 μM), 17S (1.02 μM) and Pb$^{2+}$ (1 μM) after 15 min reaction; 4: ATMND (1 μM), 17E$_{ab}$ (2.14 μM), 17S (1.02 μM), Pb$^{2+}$ (1 μM) and EDTA (1 mM) after 15 min reaction. The fluorescent spectra in (D) were collected in buffer B (10 mM HEPES pH 7.0, 100 mM NaCl, 1 mM EDTA). 1: ATMND (500 nM); 2: ATMND (500 nM), AAP (918 nM) and L1$_{ab}$ (1.17 μM); 3: ATMND (500 nM), AAP (918 nM), S1 (1.17 μM) and adenosine (100 μM). The excitation wavelength was 358 nm. All spectra were recorded at 5° C.

FIG. 9E is a digital image showing the activity assay of the 8-17 DNAzyme and its abasic-site containing variants using denatured PAGE (20% acrylic amide). The 24 base pair (bp) substrate 17S (1 μM) was fluorescein-labeled at 3'-end. The assay was carried out in the presence of 2 μM DNAzymes and 1 μM Pb$^{2+}$ in 25 mM HEPES pH 7.0, 100 mM NaCl, at 5° C. for 10 minutes. 1: no DNAzyme; 2,3: 17E$_{ab}$; 4,5: 17E$_G$-G; 6: Mutant 17E$_{ab}$; 7,8: 17E$_{ab}$ with 2 μM ATMND; 9,10: 17E$_G$. Sequences: 17E$_G$-G (17E$_G$ with G base removed from 3'-end): 5'-ACAGACATCTCTTCTCCGAGCCGGTC-GAAATAGGGA-3' (SEQ ID NO: 36) Mutant 17E$_{ab}$ (17E$_{ab}$ with T replaced by underlined C): 5'-ACAGACATCTCTTC CCCGAGCCGGTCGAAATAG X GAG-3' (SEQ ID NO: 37).

FIG. 9F is a graph showing the effect of mutation in abasic-site containing 17E$_{ab}$ on the kinetics of fluorescence enhancement by Pb$^{2+}$-catalyzed cleavage of 17S. Condition: 1 μM ATMND, 1 μM 17S, 2 μM DNAzyme, 0 or 200 nM Pb$^{2+}$, 25 mM HEPES pH 7.0, 100 mM NaCl, at 5° C. $\lambda_{ex}/\lambda_{em}$=358/405 nm.

Sequences: Mutant 17E$_{ab}$ (17E$_{ab}$ with T replaced by underlined C):

(SEQ ID NO: 38)
5'-ACAGACATCTCTTC CCCGAGCCGGTCGAAATAG X GAG-3'

FIG. 9G is a graph showing the kinetics of fluorescence enhancement by Pb$^{2+}$-catalyzed cleavage at lower Pb$^{2+}$ concentration range. $\lambda_{ex}/\lambda_{em}$=358/405 nm. Conditions: ATMND, 2.14 μM 17E$_{ab}$, 1.02 μM 17S in 25 mM HEPES pH 7.0, 100 mM NaCl at 5° C. The decrease of fluorescence during the first 2 minutes is because the Pb$^{2+}$ stock solution added at 0 minute is at room temperature and 2 minutes is required for the equilibrium of temperature.

Figure 10B:
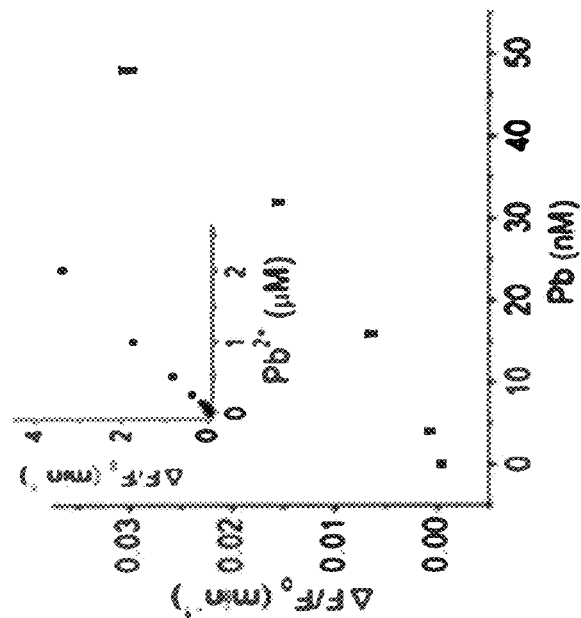
Figure 10A:
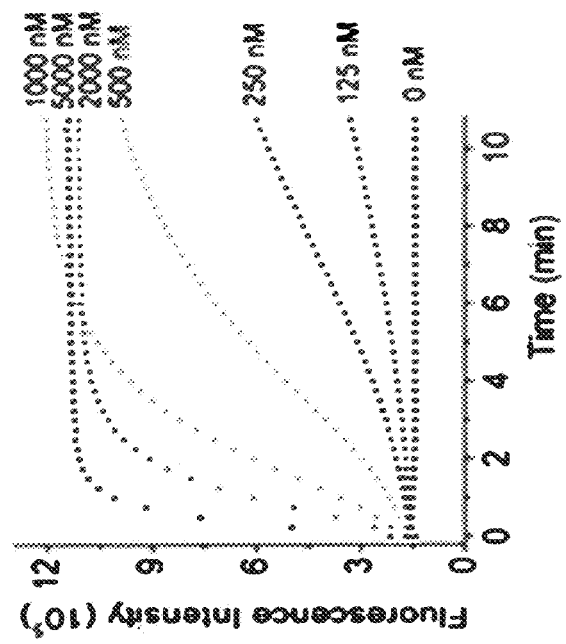

FIGS. 10A and B are graphs showing the (A) kinetics of fluorescence enhancement by Pb$^{2+}$-catalyzed cleavage, and (B) relationship between fluorescence enhancement rate and Pb$^{2+}$ concentrations. Fluorescence enhancement rate was calculated within 3~5 min after Pb$^{2+}$ addition. $\lambda_{ex}/\lambda_{em}$=358/405 nm. Condition: 1 μM ATMND, 2.14 μM 17E$_{ab}$, 1.02 μM 17S in 25 mM HEPES pH 7.0, 100 mM NaCl at 5° C.

Figure 11:
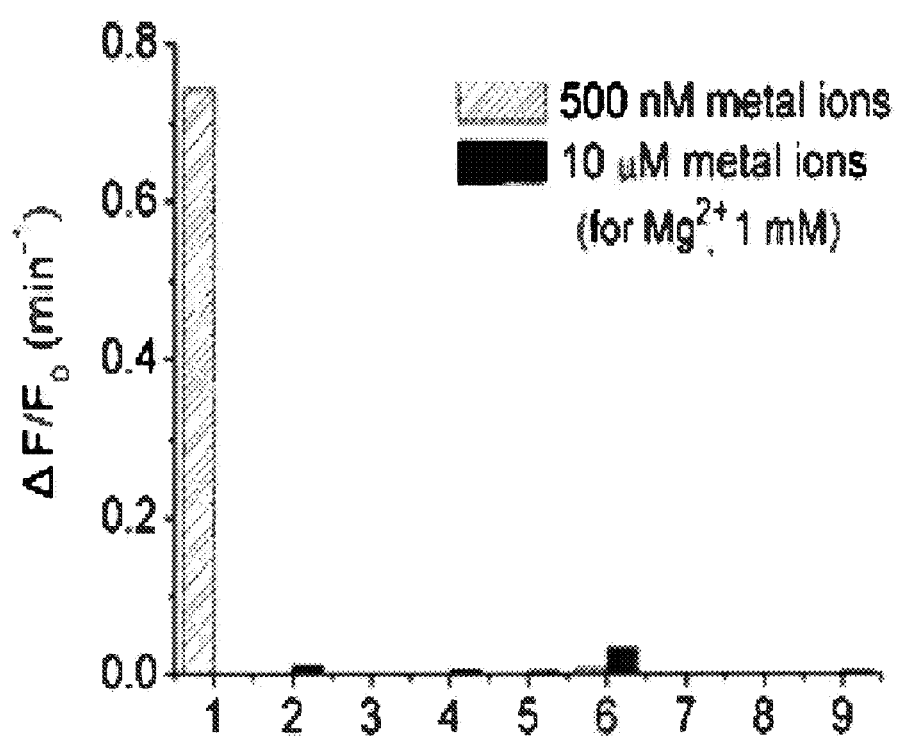

FIG. 11 is a bar graph showing the selectivity of ATMND-17E$_{ab}$-17S system for Pb$^{2+}$ detection over other divalent metal ions. 1: 500 nM Pb; 2: Mg$^{2+}$; 3: Mn$^{2+}$; 4: Fe$^{2+}$; 5: Co$^{2+}$; 6: Zn$^{2+}$; 7: Ni$^{2+}$; 8: Hg$^{2+}$; 9: Cd$^{2+}$.

Figure 12A:
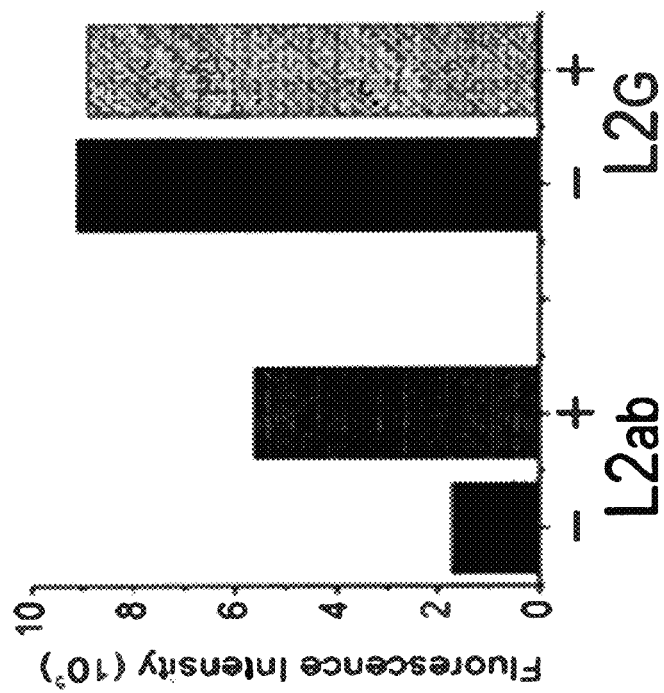

FIGS. 12A and B are bar graphs showing the effect of abasic site on the fluorescence response of (A) DNAzyme to Pb$^{2+}$ and (B) aptamer to adenosine in this label-free method. For (A), in the absence (−) and presence (+) of 1 μM Pb$^{2+}$; for (B), in the absence (−) and presence (+) of 1 mM adenosine.

FIG. 13A is a graph showing the fluorescence intensity of ATMND-AAP-L1$_{ab}$ in the presence of different concentrations of adenosine, uridine and cytidine. Inset: adenosine in 0~25 μM range. $\lambda_{ex}/\lambda_{em}$=358/405 nm. Condition: 500 nM ATMND, 918 nM AAP, 1.17 μM L1$_{ab}$ in 10 mM HEPES pH 7.0, 100 mM NaCl, 1 mM EDTA at 5° C.

FIG. 13B is a graph showing the effect of mutations in adenosine aptamer AAP on the fluorescence enhancement ratio upon binding with different concentrations of adenosine. Condition: 500 nM ATMND, 1 μM APP or APP mutants, 1.25 μM L1$_{ab}$, 0, 50 or 100 μM adenosine, 10 mM HEPES pH 7.0, 100 mM NaCl, 1 mM EDTA, at 5° C. $\lambda_{ex}/\lambda_{em}$=358/405 nm.

Sequences (Mutation sites compared to APP are underlined, where in APP is A base):

APP Mut1:
(SEQ ID NO: 25)
5'-TGTCGTTGACCTGGGGGAGTATTGCGGAGG GAGGT-3';

APP Mut2:
(SEQ ID NO: 39)
5'-TGTCGTTGACCTGGGGG CGTATTGCGGAGGAAGGT-3';

APP Mut3:
(SEQ ID NO: 40)
5'-TGTCGTTGACCTGGGGGAGTATTGCGGAGG CAGGT-3';

APP Mut4:
(SEQ ID NO: 41)
5'-TGTCGTTGACCTGGGGGAGTATTGCGGAGG TAGGT-3';

APP Mut5:
(SEQ ID NO: 42)
5'-TGTCGTTGACCTGGGGG TGTATTGCGGAGGAAGGT-3'.

Figure 14:
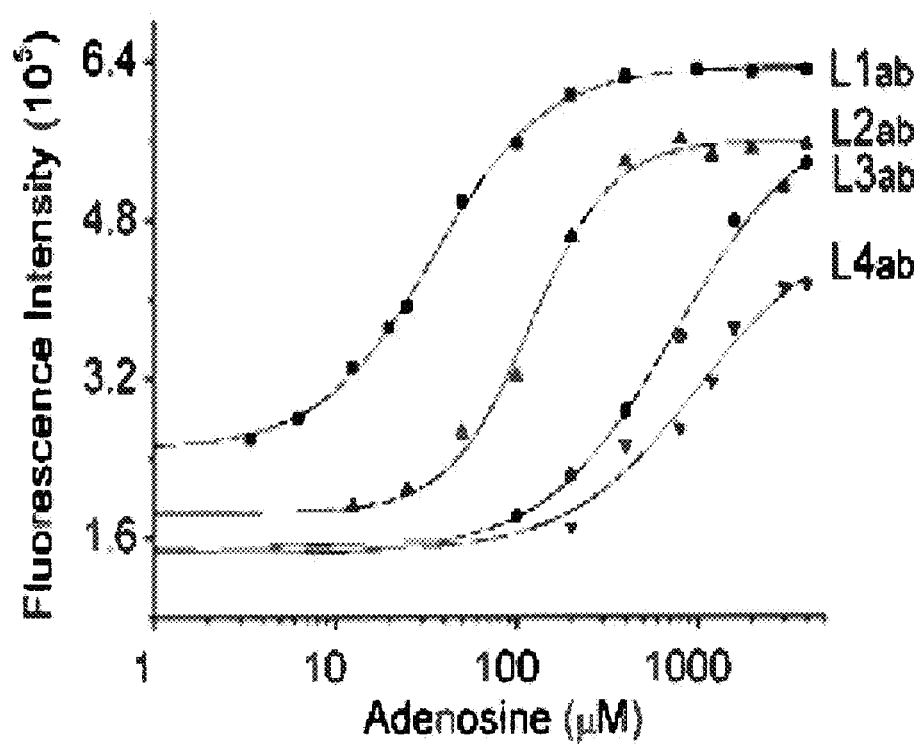

FIG. 14 is a graph showing the fine-tuning of the dynamic range of adenosine detection using different lengths of abasic site-containing ssDNA.

Figure 15:
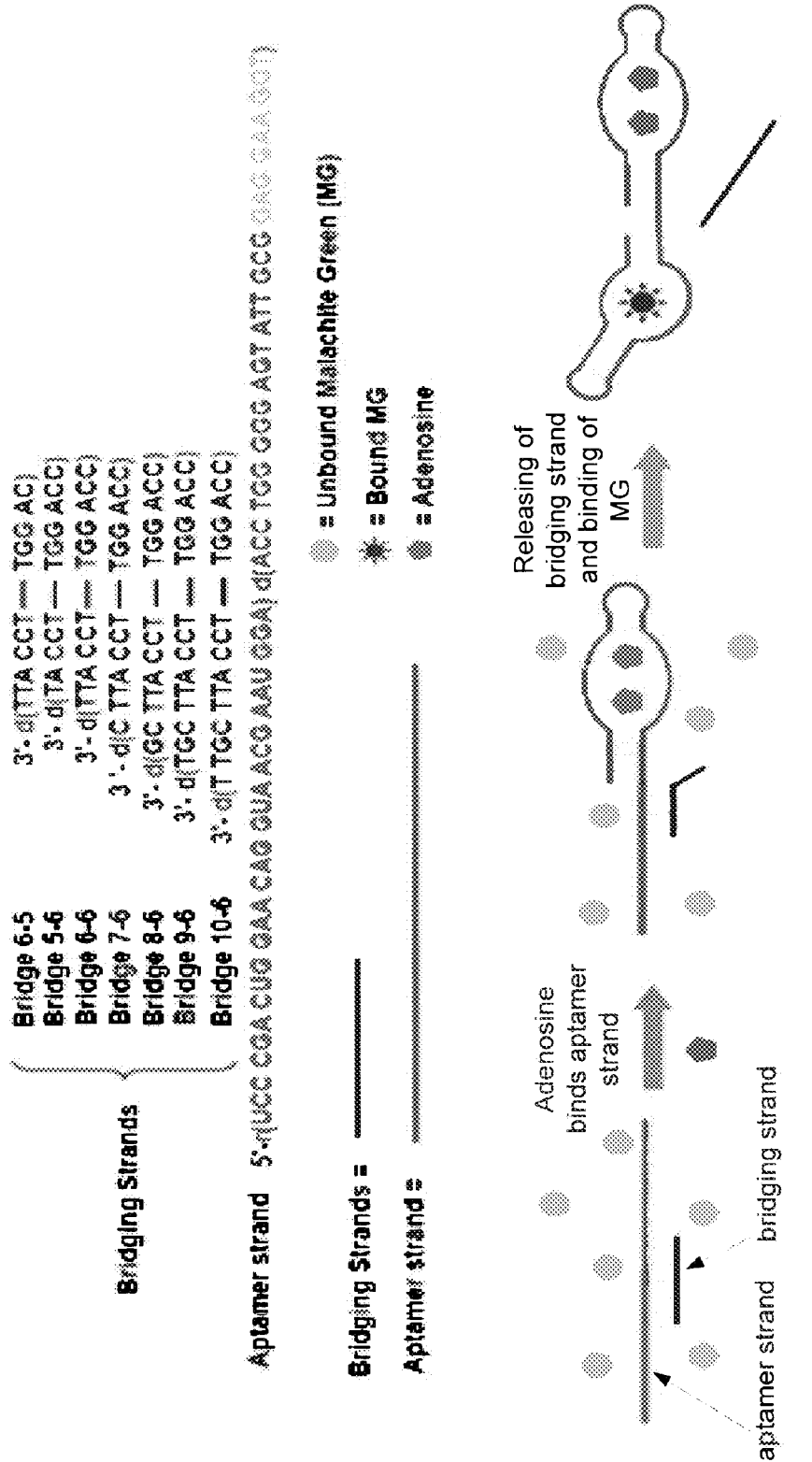

FIG. 15 is a schematic showing the regulation of the fluorescence of malachite green (MG) by adenosine. Without adenosine, the affinity of the aptamer strand (SEQ ID NOS:

26 and 27) is inhibited by the bridging strand (SEQ ID NOS: 28-34). With adenosine, the bridging strand separates from the aptamer strand, which then binds malachite green, leading to an enhancement of fluorescence.

FIGS. 16A and B are graphs showing the (A) fluorescence of 1 µM MG with (top trace) and without (bottom trace) the 1 µM aptamer strand. 20 mM Tris (pH 7.4), 145 mM NaCl and 5 mM $MgCl_2$ were used as the buffer and (B) performance of the sensor with varied potassium concentration in the buffer. 1 µM aptamer strand, bridge 6-5 and MG were used as the sensor. Besides KCl and NaCl, 5 mM $MgCl_2$ and 20 mM Tris (pH 7.4) were present in buffer, too. 5 mM adenosine was added at t=10 s and fluorescence versus time was recorded and plotted.

FIG. 17 is a graph showing sensor performance with different sequences of the bridging strands. 1 µM aptamer strand, bridging strand and MG were used as the sensor. 20 mM Tris (pH 7.4), 140 mM KCl, 5 mM NaCl and 5 mM $MgCl_2$ were used as buffer. 5 mM adenosine was added at t=25 s and fluorescence versus time was recorded and plotted. Bridge 9-6 (SEQ ID NO: 33) has the highest fluorescence increase.

FIGS. 18A and B are graphs showing the optimization of the ratio of the aptamer and bridge 9-6 strand and MG. (A) The nucleic strands were kept 1 µM and MG concentration varied; (B) the aptamer strands and MG were kept 1 µM and 0.6 µM respectively and the concentration of bridge 9-6 varied.

Figure 19:
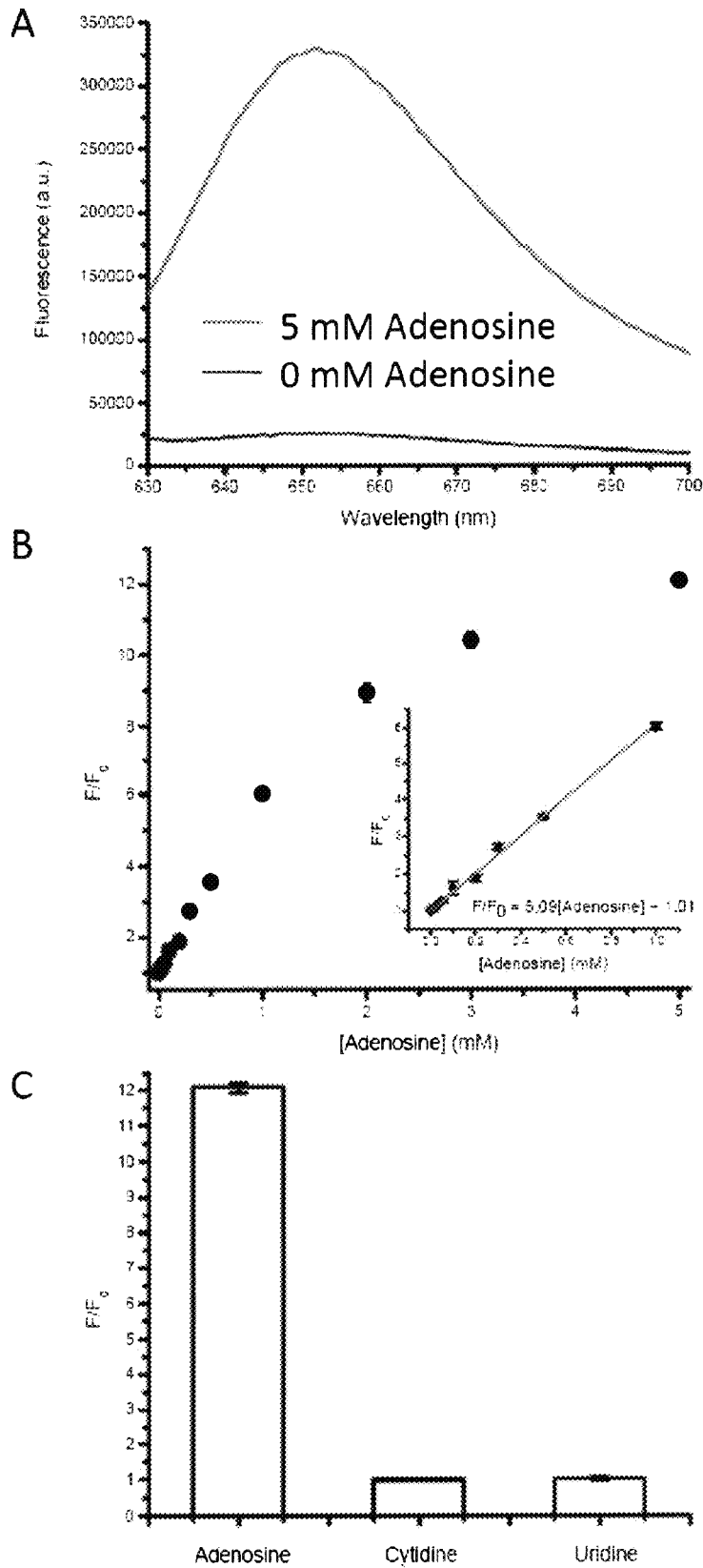

FIGS. 19A-C are graphs showing (A) the fluorescence enhancement of the optimized sensor upon the addition of adenosine; (B) the saturated fluorescence of malachite green with various concentrations of adenosine. The inset shows the fluorescence response at low concentrations of adenosine and the line shows a linear fitting of the data; (C) selectivity of the sensor towards other nucleosides. Cytidine and uridine did not increase the fluorescence of MG.

FIGS. 20A-D are schematic drawings showing generic sequences of structures that are specific to (A) $Pb^{2+}$ (SEQ ID NOS: 43-44), (B) $UO_2^{2+}$ (SEQ ID NOS: 45-46), (C) adenosine (SEQ ID NOS: 47-48), and (D) $Hg^{2+}$ (SEQ ID NOS: 49-50), using unmodified DNA via a vacant site approach.

FIGS. 21A-B are schematic drawings showing generic sequences of structures that are specific to (A) $Pb^{2+}$ (SEQ ID NOS: 51-52) and (B) adenosine (SEQ ID NOS: 53-54) using an abasic site approach.

Figure 21C:
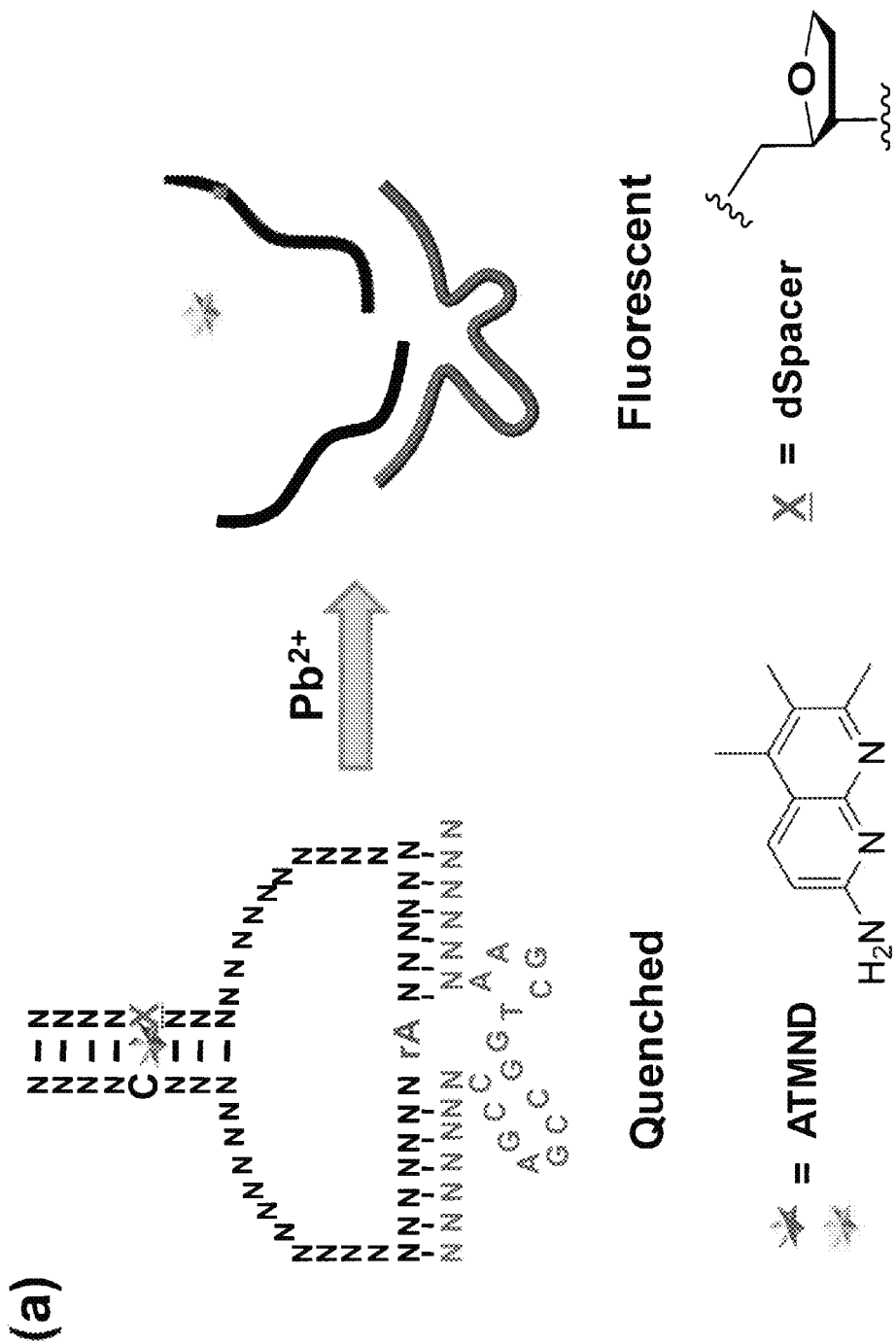
Figure 21D:
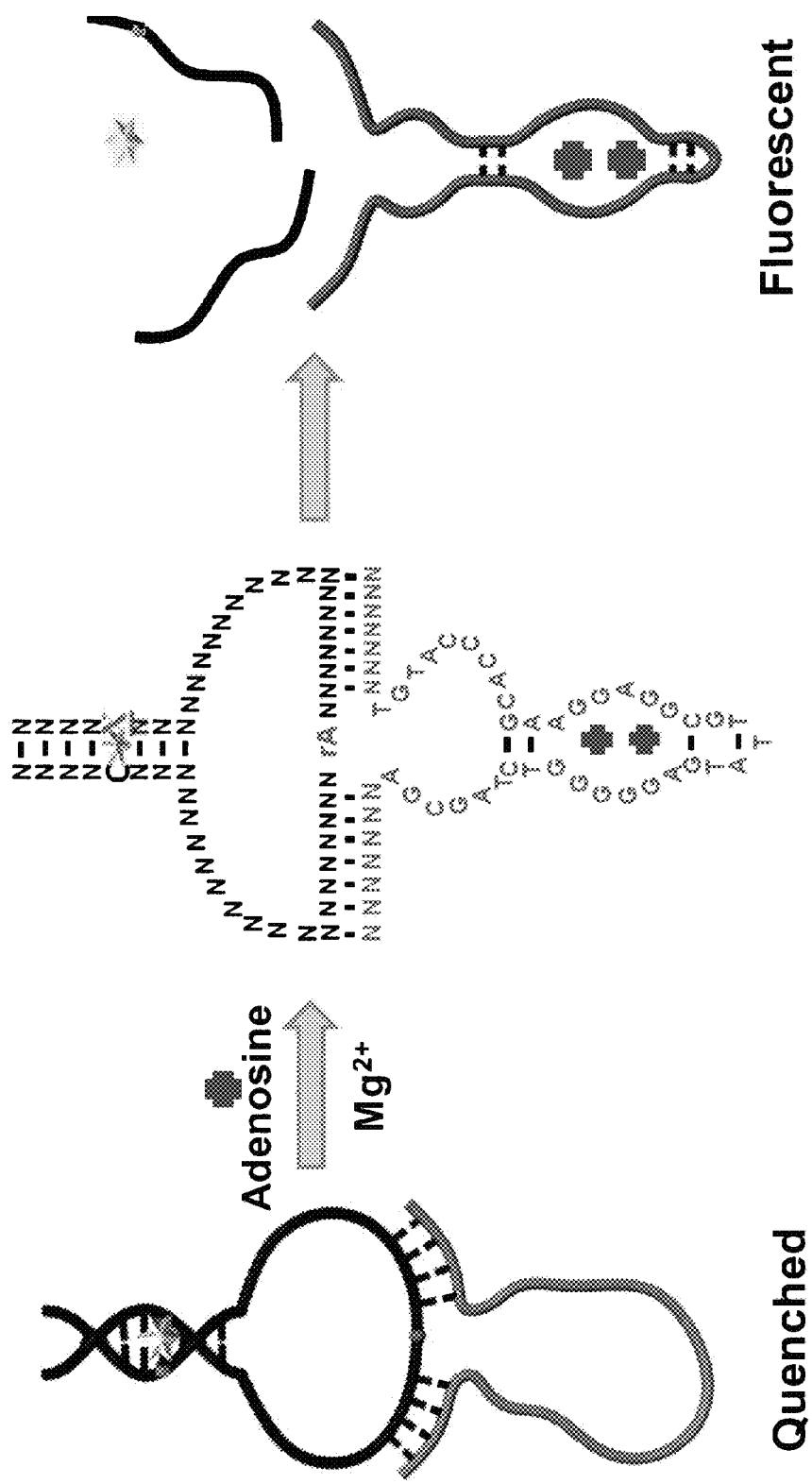

FIGS. 21C-D are schematic drawings showing generic sequences of structures that are specific to (A) $Pb^{2+}$ (SEQ ID NOS: 94-95) and (B) adenosine (SEQ ID NOS: 96-97) using a CAMB approach.

FIG. 22 shows exemplary DNAzyme sequences for mercury (SEQ ID NOS: 55-56), lead (SEQ ID NOS: 57-58), or copper (SEQ ID NOS: 59-60) that can be modified to include a vacant or abasic site using the methods provided herein.

FIG. 23 is a schematic drawing showing exemplary label-free sensor sequences for the detection of theophylline using an aptamer approach (SEQ ID NOS: 68 and 69 show the unmodified aptamers, SEQ ID NOS: 35 and 70 show the modifications to incorporate an abasic site). Underlined strand (SEQ ID NOS: 69 and 35) are the DNA strand partially complementary to the aptamer RNA strand (SEQ ID NOS: 68 and 70, respectively) above it.

Figure 24:
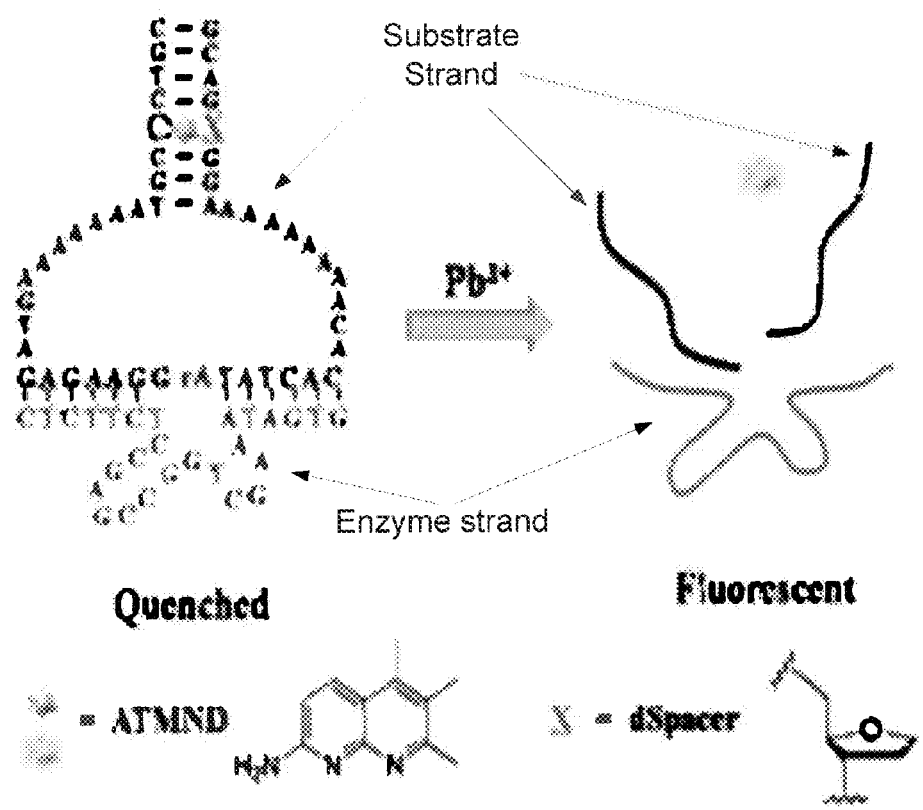

FIG. 24 is a schematic illustration of fluorescent detection of $Pb^{2+}$ by the label-free CAMB sensor. SEQ ID NOS: 73 is the enzyme strand, and SEQ ID NO: 78 is the substrate strand.

Figure 25:
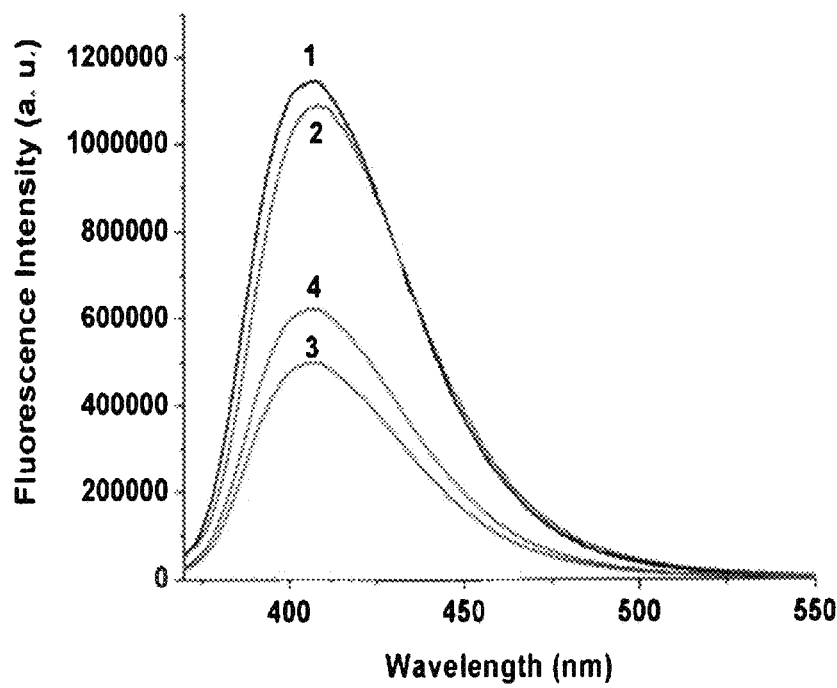

FIG. 25 is a graph showing fluorescence emission spectra of ATMND in the absence and presence of 17E (6+6)-MB 1 for $Pb^{2+}$ detection, which were collected in buffer A (25 mM HEPES at pH 7.0 and 200 mM NaCl): 1, ATMND (0.5 µM); 2, ATMND (0.5 µM), 17E (6+6) (1.0 µM) and control MB3 (1.0 µM); 3, ATMND (0.5 µM), 17E (6+6) (1.0 µM) and MB1 (1.0 µM); 4, ATMND (1 µM), 17E (6+6) (1.0 µM), MB1 (1.0 µM) and $Pb^{2+}$ (1,1M) after 15 min reaction. The excitation wavelength was 358 nm. All spectra were recorded at 5° C.

Figure 26:
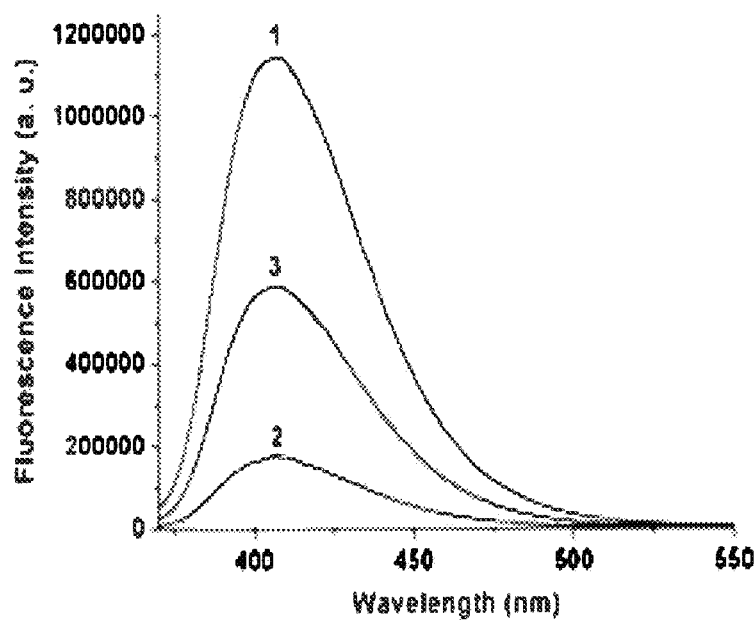

FIG. 26 is a graph showing the fluorescence emission spectra of ATMND in the absence and presence of 17E (6+6)—MB2 for $Pb^{2+}$ detection, which were collected in buffer A (25 mM HEPES at pH 7.0 and 200 mM NaCl): 1, ATMND (0.5 µM); 2, ATMND (0.5 µM), 17E (6+6) (1.0 µM) and MB2 (1.0 µM); 3, ATMND (0.5 µM), 17E (6+6) (1.0 µM), MB2 (1.0 µM) and $Pb^{2+}$ (1.0 µM) after 15 min reaction. The excitation wavelength was 358 nm. All spectra were recorded at 5° C.

Figure 27:
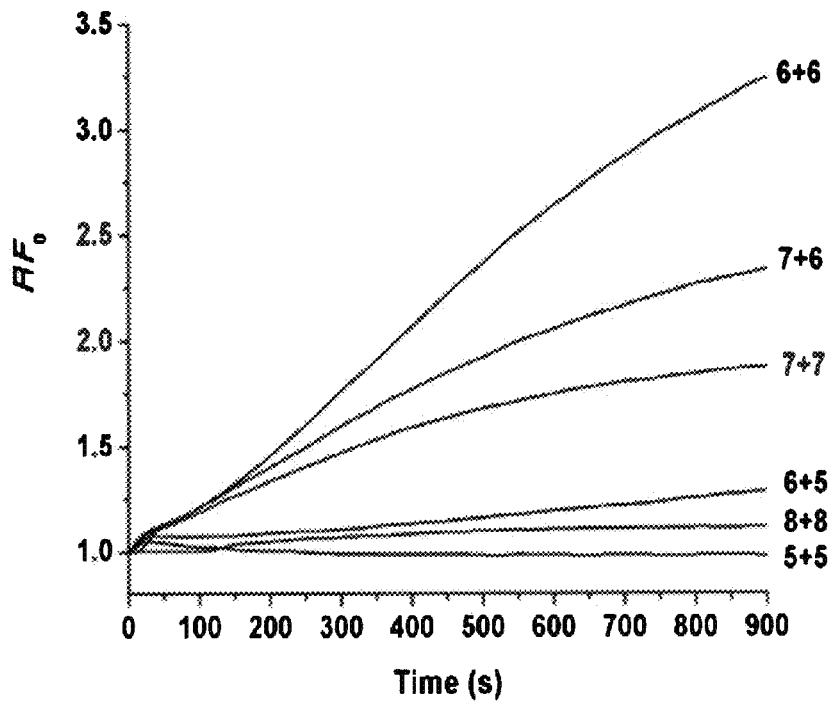

FIG. 27 is a graph showing time-dependent fluorescence enhancement of DNAzyme strands with different arm lengths and MB2 as a substrate strand in the presence of 1 µM $Pb^{2+}$. $\lambda_{ex}/\lambda_{em}$=358/405 nm. Condition: 0.5 µM ATMND, 1 µM 17E DNAzyme, 1 µM MB2 in buffer A (25 mM HEPES pH 7.0, 200 mM NaCl) at 5° C.

Figure 28:
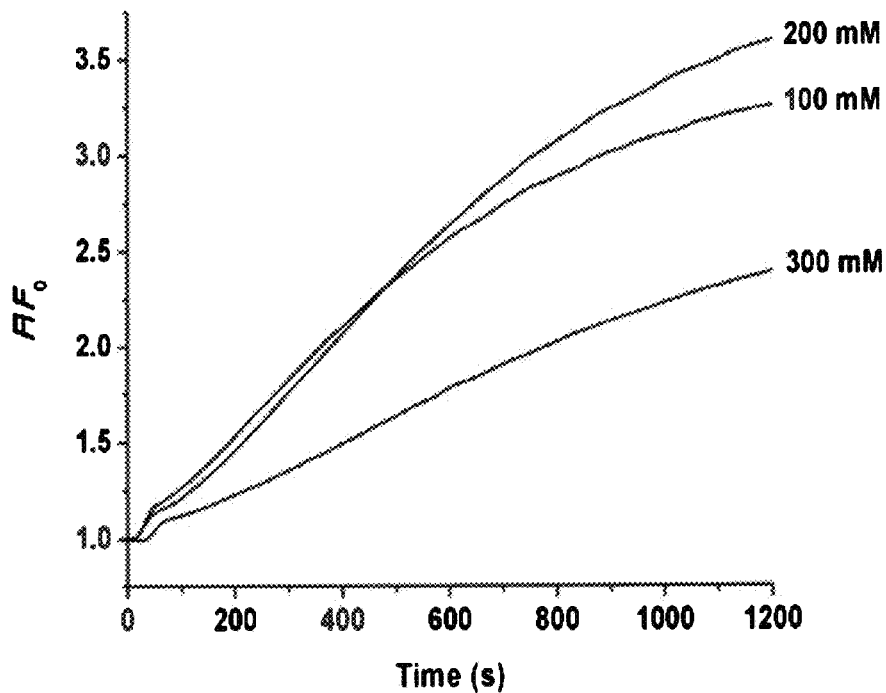

FIG. 28 is a graph showing time-dependent fluorescence enhancement of 17E (6+6)-MB2 system with different concentrations of NaCl in the presence of 1 µM $Pb^{2+}$. $\lambda_{ex}/\lambda_{em}$=358/405 nm. Condition: 0.5 µM ATMND, 1 µM 17E (6+6) DNAzyme, 1 µM MB2 in 25 mM HEPES pH 7.0, at 5° C.

Figures 29A, 29B:
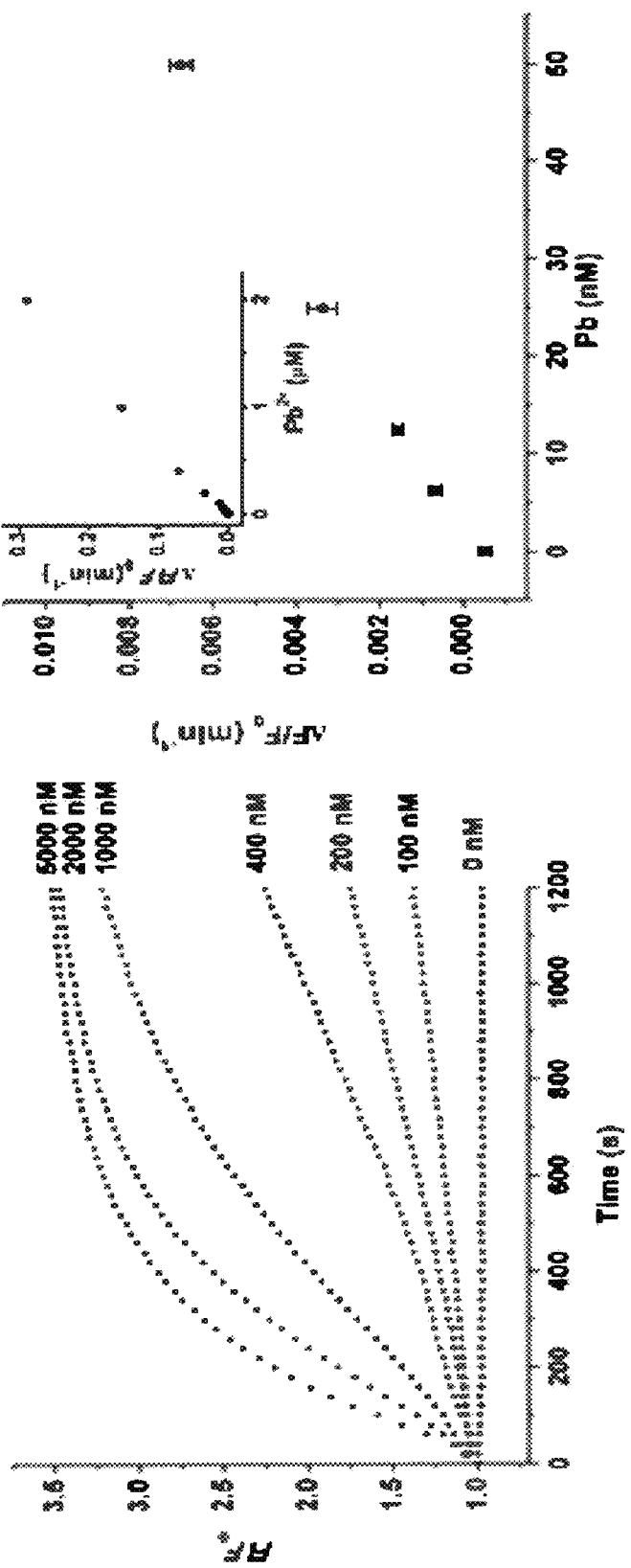

FIG. 29A is a graph showing the kinetics of fluorescence enhancement by $Pb^{2+}$-induced catalytic reaction.

FIG. 29B is a graph showing the relationship between the fluorescence enhancement rate and $Pb^{2+}$ concentration. Fluorescence enhancement rate was calculated within 5-8 min after $Pb^{2+}$ addition. Excitation and emission are at $\lambda_{ex}/\lambda_{em}$=358/405 nm. Condition: 0.5 µM ATMND, 1 µM 17E (6+6), 1 µM MB2 in 25 mM HEPES pH 7.0, 200 mM NaCl at 5° C.

Figure 30:
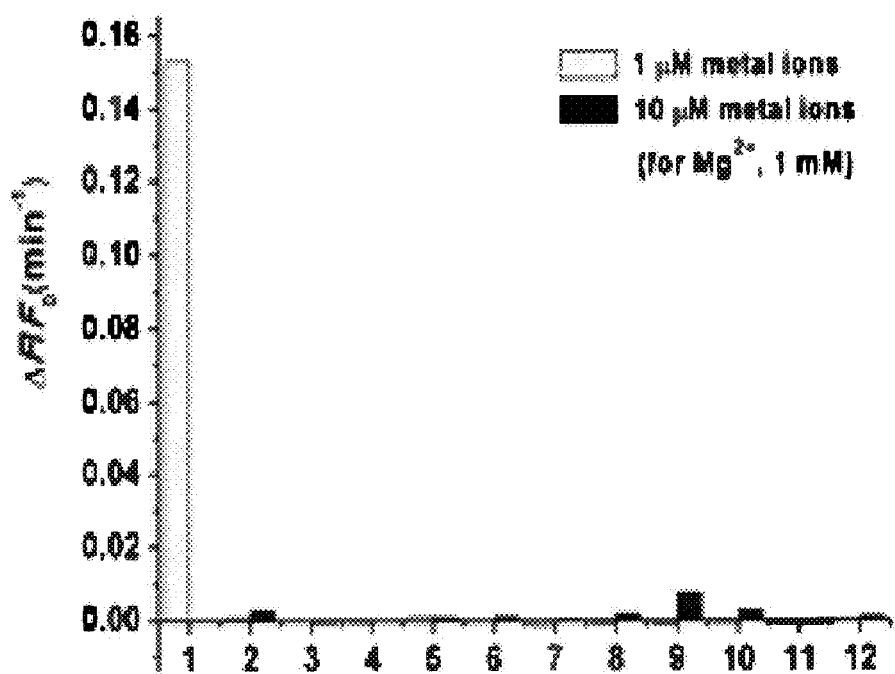

FIG. 30 is a bar graph showing the selectivity of the label-free CAMB sensor for $Pb^{2+}$ detection over other divalent metal ions: 1, 1 µM $Pb^{2+}$; 2, $Mg^{2+}$; 3, $Ca^{2+}$; 4, $Sr^{2+}$; 5, $Ba^{2+}$; 6, $Mn^{2+}$; 7, $Fe^{2+}$; 8, $Co^{2+}$; 9, $Zn^{2+}$; 10, $Ni^{2+}$; 11, $Hg^{2+}$; 12, $Cd^{2+}$.

Figure 31:
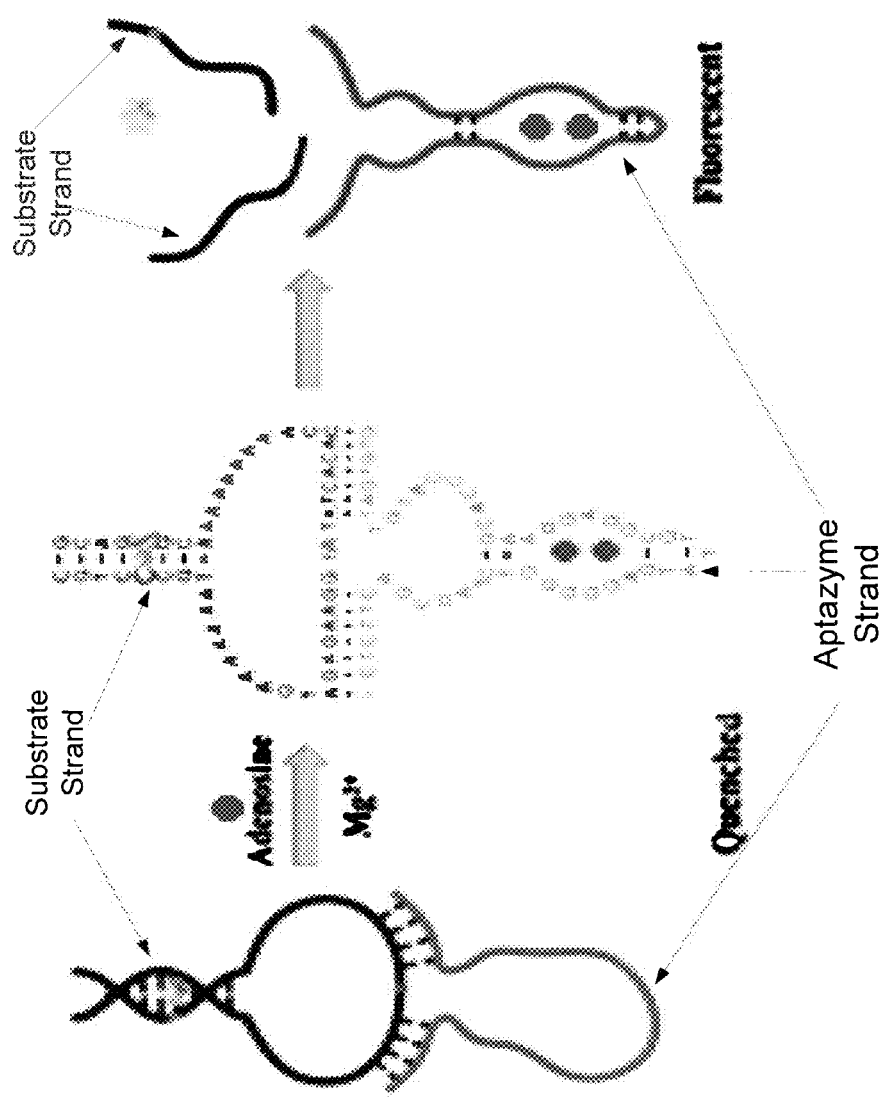

FIG. 31 is a schematic illustration of fluorescent detection of adenosine by an aptazyme based on 10-23 DNAzyme using the label-free CAMB sensor. The aptazyme sequence is shown in SEQ ID NO: 81 (bottom) and the substrate strand in SEQ ID NO: 78 (top).

Figure 32:
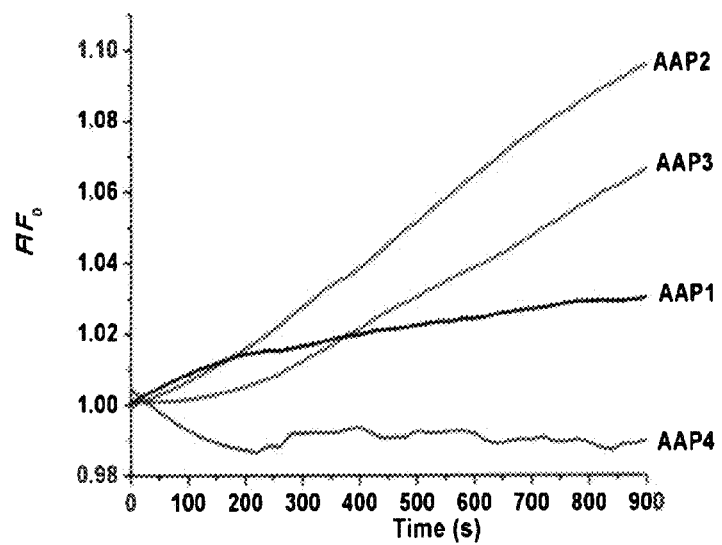

FIG. 32 is a graph showing the time-dependent fluorescence enhancement of aptazyme with different arm lengths and binding lengths and MB2 as a substrate DNA (SEQ ID NO: 78) in the presence of 500 µM adenosine. $\lambda_{ex}/\lambda_{em}$=358/405 nm. Condition: 0.5 µM ATMND, 1 µM aptazyme, 1 µM MB2 in buffer B (25 mM HEPES pH 7.0, 5 mM $MgCl_2$, and 100 mM NaCl) at 5° C.

Figure 33:
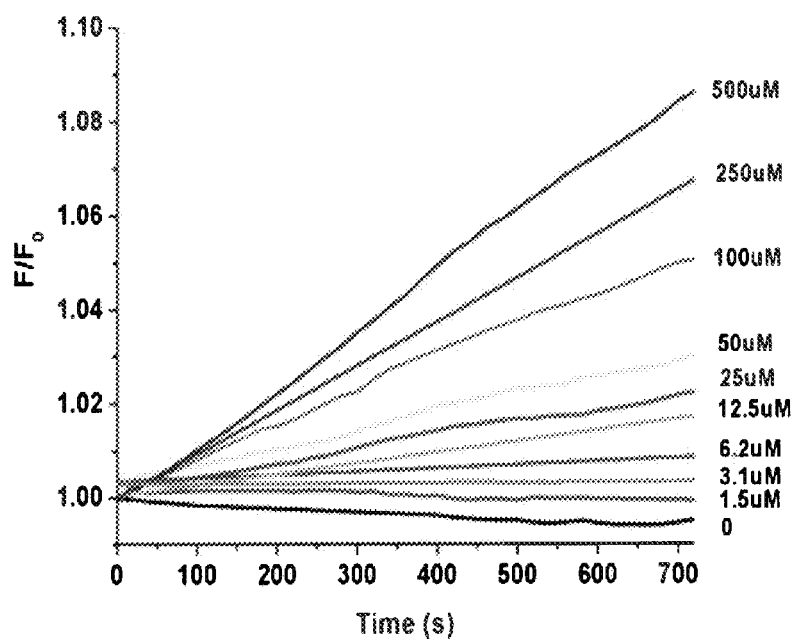

FIG. 33 is a graph showing the kinetics of fluorescence enhancement of the label-free CAMB sensing system in the presence of different concentrations of adenosine. $\lambda_{ex}/\lambda_{em}$=358/405 nm. Condition: 0.5 µM ATMND, 1 µM AAP2, 1 µM MB2 in buffer B (25 mM HEPES pH 7.2, 5 mM $Mg^{2+}$, and 100 mM NaCl) at 5° C.

Figure 34:
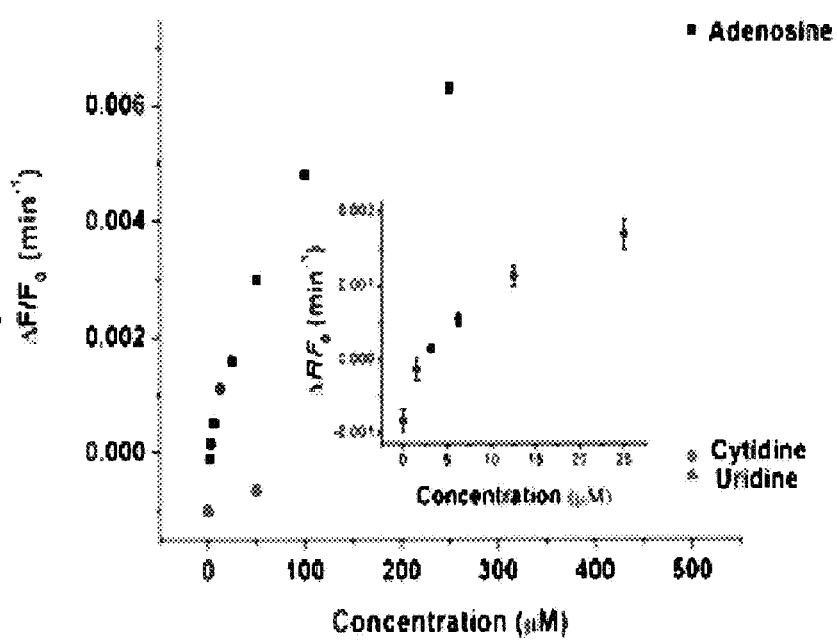

FIG. 34 is a graph showing the relationship between the rate of fluorescence enhancement and the concentration of adenosine, uridine and cytidine. Fluorescence enhancement rates were calculated within 5-8 min after nucleotide addition. Inset: results of adenosine detection in the range of 0-25 µM. Excitation and emission are at: $\lambda_{ex}/\lambda_{em}$=358/405 nm. Condition: 0.5 µM ATMND, 1 µM APP2, and 1 µM MB2 in 25 mM HEPES at pH 7.2, 5 mM $MgCl_2$, 100 mM NaCl at 5° C.

Figure 35:
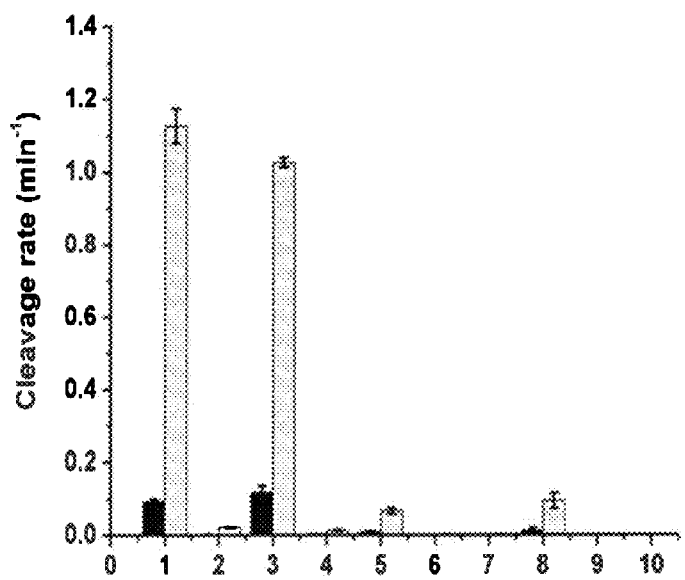

FIG. 35 is a graph showing the cleavage rate of 8-17 DNAzyme and its mutants (SEQ ID NOS: 84-92) of single turnover (dense) and multiple turnover (black) reactions in the presence of 100 μM $Pb^{2+}$. 1, 8-17; 2, M1; 3, M2; 4, M3; 5, M4; 6, M5; 7, M6; 8, M7; 9, M8; 10, M9.

Figure 36A:
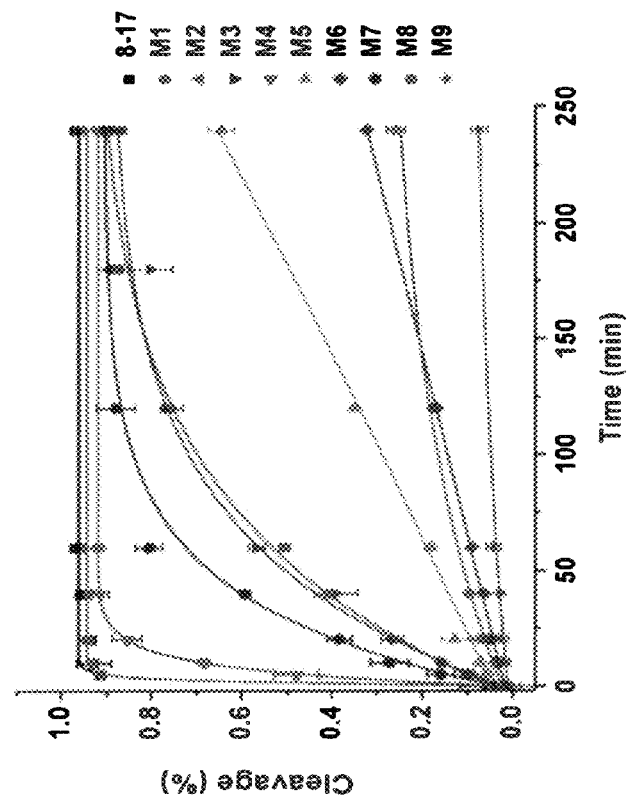
Figure 36B:
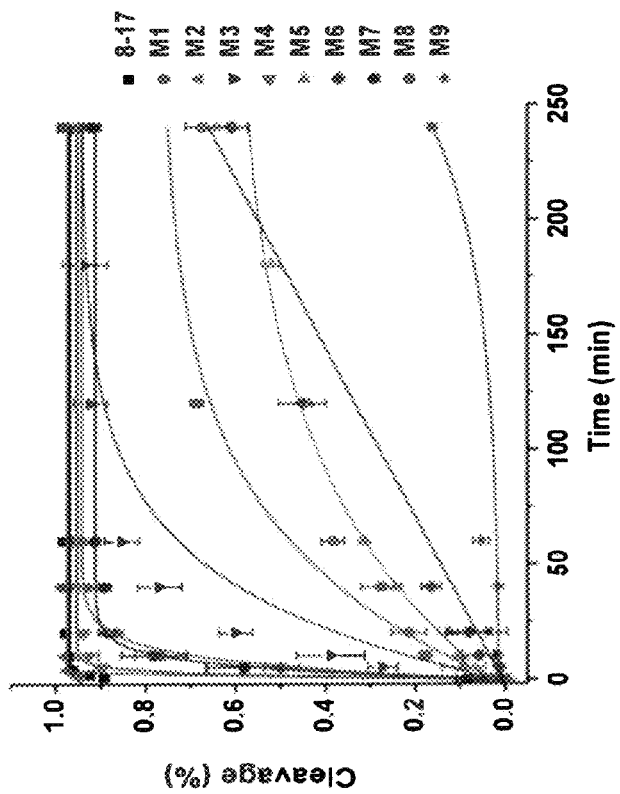

FIGS. 36A and B are graphs showing evaluation of DNAzyme activity by PAGE assays in the presence of 100 μM $Pb^{2+}$. Condition: (A) single turnover reaction with 0.5 μM ATMND, 0.2 μM DNAzyme, 1 μM MB2; (B) multiple turnover reaction with 0.5 μM ATMND, 2 μM DNAzyme, 1 μM MB2 in buffer A (25 mM HEPES pH 7.0, 200 mM NaCl) at 5° C.

SEQUENCE LISTING

The nucleic acid sequences listed herein are shown using standard letter abbreviations for nucleotide bases, as defined in 37 C.F.R. 1.822. Only one strand of each nucleic acid sequence is shown, but the complementary strand is understood as included by any reference to the displayed strand. The sequence listing is submitted as an ASCII text file, named "7950-85870-02_ST25.txt," created on Oct. 5, 2011, 27.3 KB, which is incorporated by reference herein.

SEQ ID NO: 1 is an enzyme nucleic acid strand of a sensor comprising a vacant site and a DNAzyme specific for lead.

SEQ ID NO: 2 is a substrate nucleic acid strand of a sensor comprising a vacant site and a DNAzyme specific for lead.

SEQ ID NO: 3 is a mutated substrate nucleic acid strand of a sensor for lead that does not include a vacant site.

SEQ ID NO: 4 is a mutated enzyme nucleic acid strand of a sensor comprising an inactive lead DNAzyme.

SEQ ID NO: 5 is an aptamer sequence specific for adenosine.

SEQ ID NOS: 6 and 7 are inactive adenosine aptamers.

SEQ ID NOS: 8-11 are exemplary ssDNAs that can hybridize to the adenosine aptamer of SEQ ID NO: 5.

SEQ ID NO: 12 is an enzyme nucleic acid strand of a sensor comprising a DNAzyme specific for $UO_2^{2+}$.

SEQ ID NO: 13 is a substrate nucleic acid strand of a sensor comprising a DNAzyme specific for $UO_2^{2+}$.

SEQ ID NO: 14 is an aptamer sequence specific for mercury. SEQ ID NO: 15 is an exemplary ssDNA that can hybridize to the mercury aptamer of SEQ ID NO: 14.

SEQ ID NO: 16 is an enzyme nucleic acid strand of a sensor comprising an abasic site and a DNAzyme specific for lead.

SEQ ID NO: 17 is a mutated enzyme nucleic acid strand for an inactive lead DNAzyme.

SEQ ID NO: 18 is a substrate nucleic acid strand of a sensor comprising a DNAzyme specific for lead.

SEQ ID NO: 19 is an aptamer sequence specific for adenosine.

SEQ ID NOS: 20-23 are exemplary ssDNAs that can hybridize to the adenosine aptamer of SEQ ID NO: 19 and have an abasic site.

SEQ ID NO: 24 is an exemplary ssDNA similar to SEQ ID NO: 20 and can hybridize to the adenosine aptamer of SEQ ID NO: 19 but has a G base, instead of an abasic site.

SEQ ID NO: 25 is a mutant adenosine aptamer sequence (mutation of SEQ ID NO: 19).

SEQ ID NOS: 26 and 27 are nucleic acid sequences that make up the aptamer strand for adenosine. SEQ ID NO: 26 is the adenosine DNA aptamer sequence portion and SEQ ID NO: 27 is the MG RNA aptamer sequence. SEQ ID NO: 27 is the 5'-portion of the sequence, and SEQ ID NO: 26 is at the 3'-end.

SEQ ID NOS: 28-34 are exemplary bridging strands that can hybridize to the aptamer of SEQ ID NOS: 26 and 27 (these sequences bind the 3'-end of SEQ ID NO: 27 and the 5'-end of SEQ ID NO: 26).

SEQ ID NO: 35: is an exemplary ssDNA that can hybridize to the theophylline aptamer of SEQ ID NO: 70.

SEQ ID NOS: 36-38 are mutated enzyme nucleic acid strands for an inactive lead DNAzyme (mutations of SEQ ID NO: 16).

SEQ ID NOS: 39-42 are mutant adenosine aptamer sequence (mutations of SEQ ID NO: 19).

SEQ ID NO: 43 is a generic enzyme nucleic acid strand of a sensor comprising a vacant site and a DNAzyme specific for lead.

SEQ ID NO: 44 is a generic substrate nucleic acid strand of a sensor comprising a vacant site and a DNAzyme specific for lead.

SEQ ID NO: 45 is a generic enzyme nucleic acid strand of a sensor comprising a vacant site and a DNAzyme specific for uranium.

SEQ ID NO: 46 is a generic substrate nucleic acid strand of a sensor comprising a vacant site and a DNAzyme specific for uranium.

SEQ ID NO: 47 is a generic aptamer sequence specific for adenosine.

SEQ ID NO: 48 is an exemplary generic ssDNA that can hybridize to the adenosine aptamer of SEQ ID NO: 47.

SEQ ID NO: 49 is a generic aptamer sequence specific for mercury.

SEQ ID NO: 50 is an exemplary generic ssDNA that can hybridize to the mercury aptamer of SEQ ID NO: 49. 5'-n AAA nnn-3'

SEQ ID NO: 51 is an exemplary generic enzyme nucleic acid strand of a sensor comprising an abasic site and a DNAzyme specific for lead.

SEQ ID NO: 52 is an exemplary generic substrate nucleic acid strand of a sensor comprising a DNAzyme specific for lead.

SEQ ID NO: 53 is an exemplary generic aptamer sequence specific for adenosine.

SEQ ID NO: 54 an exemplary generic ssDNA that can hybridize to the adenosine aptamer of SEQ ID NO: 53.

SEQ ID NO: 55 is an exemplary generic enzyme nucleic acid strand of a sensor comprising DNAzyme specific for mercury.

SEQ ID NO: 56 is an exemplary generic substrate nucleic acid strand of a sensor comprising a DNAzyme specific for mercury.

SEQ ID NO: 57 is an exemplary generic enzyme nucleic acid strand of a sensor comprising DNAzyme specific for lead.

SEQ ID NO: 58 is an exemplary generic substrate nucleic acid strand of a sensor comprising a DNAzyme specific for lead. 5'-nnn nnn nrnG nnn nnn-3'

SEQ ID NO: 59 is an exemplary generic enzyme nucleic acid strand of a sensor comprising DNAzyme specific for copper.

SEQ ID NO: 60 is an exemplary generic substrate nucleic acid strand of a sensor comprising a DNAzyme specific for copper.

SEQ ID NOS: 61 and 27 are nucleic acid sequences that make up the aptamer strand for arginine. SEQ ID NO: 27 is the MG RNA aptamer sequence portion and SEQ ID NO: 61 is the L-arginine aptamer sequence portion. SEQ ID NO: 27 is the 5'-portion of the aptamer sequence, and SEQ ID NO: 61 is at the 3'-end.

SEQ ID NOS: 62-67 are exemplary bridging strands that can hybridize to the aptamer of SEQ ID NOS: 27 and 61 (these sequences bind the 3'-end of SEQ ID NO: 27 and the 5'-end of SEQ ID NO: 61).

SEQ ID NO: 68 is an exemplary aptamer sequence specific for theophylline.

SEQ ID NO: 69 is an exemplary generic ssDNA that can hybridize to the theophylline aptamer of SEQ ID NO: 68. 5'-AT TCG CCC ATA GAG TGA-3'

SEQ ID NO: 70 is an exemplary aptamer sequence specific for theophylline.

SEQ ID NOS: 71-76 are exemplary enzyme nucleic acid strands of a sensor comprising a DNAzyme specific for lead.

SEQ ID NOS: 77-78 are substrate nucleic acid strands of a sensor comprising an abasic site and a DNAzyme specific for lead.

SEQ ID NO: 79 is a substrate nucleic acid strand of lacking an abasic site.

SEQ ID NOS: 80-83 are exemplary aptazyme sequences for adenosine.

SEQ ID NOS: 84-92 are mutant sequences of an 8-17 DNAzyme specific for lead.

SEQ ID NO: 93 is a substrate for DNA for gel electrophoresis.

SEQ ID NO: 94 is an exemplary generic substrate nucleic acid strand of a CAMB sensor comprising a DNAzyme specific for lead.

SEQ ID NO: 95 is an exemplary generic enzyme nucleic acid strand of a CAMB sensor comprising a DNAzyme specific for lead.

SEQ ID NO: 96 is an exemplary generic substrate nucleic acid strand of a CAMB sensor comprising an aptazyme sequence specific for adenosine.

SEQ ID NO: 97 an exemplary generic enzyme nucleic acid strand of a CAMB sensor comprising an aptazyme specific for adenosine.

DETAILED DESCRIPTION

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B."

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Sambrook et al., *Molecular Cloning: A Laboratory Manual*, 2nd ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999.

All publications, patent applications, patents, and other references mentioned herein are incorporated by reference in their entirety for all purposes, to the extent permissible by applicable rules and/or law.

In order to facilitate review of the various embodiments of the disclosure, the following explanations of specific terms are provided:

3' end: The end of a nucleic acid molecule that does not have a nucleotide bound to it 3' of the terminal residue.

5' end: The end of a nucleic acid sequence where the 5' position of the terminal residue is not bound by a nucleotide.

Aptamer: Nucleic acid molecules (such as DNA or RNA) that bind a specific target agent with high affinity and specificity. Aptamers are known in the art and have been obtained through a combinatorial selection process called systematic evolution of ligands by exponential enrichment (SELEX) (see for example Ellington et al., *Nature* 1990, 346, 818-822; Tuerk and Gold *Science* 1990, 249, 505-510; Liu et al., *Chem. Rev.* 2009, 109, 1948-1998; Shamah et al., *Acc. Chem. Res.* 2008, 41, 130-138; Famulok, et al., *Chem. Rev.* 2007, 107, 3715-3743; Manimala et al., *Recent Dev. Nucleic Acids Res.* 2004, 1, 207-231; Famulok et al., *Acc. Chem. Res.* 2000, 33, 591-599; Hesselberth, et al., *Rev. Mol. Biotech.* 2000, 74, 15-25; Wilson et al., *Annu. Rev. Biochem.* 1999, 68, 611-647; Morris et al., *Proc. Natl. Acad. Sci. U.S.A.* 1998, 95, 2902-2907). In such a process, DNA or RNA molecules that are capable of binding a target molecule of interest are selected from a nucleic acid library consisting of $10^{14}$-$10^{15}$ different sequences through iterative steps of selection, amplification and mutation. Aptamers that are specific to a wide range of targets from small organic molecules such as adenosine, to proteins such as thrombin, and even viruses and cells have been identified (Liu et al., *Chem. Rev.* 2009, 109, 1948-1998; Lee et al., *Nucleic Acids Res.* 2004, 32, D95-D100; Navani and Li, *Curr. Opin. Chem. Biol.* 2006, 10, 272-281; Song et al., TrAC, *Trends Anal. Chem.* 2008, 27, 108-117). The affinity of the aptamers towards their targets can rival that of antibodies, with dissociation constants in as low as the picomolar range (Morris et al., *Proc. Natl. Acad. Sci. U.S.A.* 1998, 95, 2902-2907; Green et al., *Biochemistry* 1996, 35, 14413-14424).

Binding: An association between two substances or molecules, such as the hybridization of one nucleic acid molecule to another (or itself), the association of a fluorophore with a nucleic acid molecule, or the interaction of a sensor disclosed herein and a target agent. An oligonucleotide molecule binds or stably binds to another nucleic acid molecule if there are a sufficient number of complementary base pairs between the oligonucleotide molecule and the target nucleic acid to permit detection of that binding.

Binding can be detected by any procedure known to one skilled in the art. In one example, binding of a target to a sensor disclosed herein is detected by observing a change in fluorescence.

One molecule is said to "specifically bind" to another molecule when a particular agent (such as a sensor disclosed herein) can specifically interact with a particular analyte, for example to specifically bind to a particular target agent. The binding is a non-random binding reaction, for example between an oligonucleotide (such as a functional nucleic acid) and a target agent. In particular examples, two compounds are said to specifically bind when the binding constant for complex formation between the components exceeds about $10^4$ L/mol, for example, exceeds about $10^6$ L/mol, exceeds about 10⁸ L/mol, or exceeds about 10¹⁰ L/mol. The binding constant for two components can be determined using methods that are well known in the art.

Complementary. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions. In particular examples disclosed herein, the complementary sequence is complementary at a labeled nucleotide, and at each nucleotide immediately flanking the labeled nucleotide.

Detect: To determine if a particular agent is present or absent, and in some example further includes quantification of the agent if detected.

DNAzymes: Functional DNA molecules that display catalytic activity toward a specific target. Also referred to as catalytic DNAs or deoxyribozymes.

Numerous DNAzymes have been isolated to display high specificity toward various metal ions such as $Pb^{2+}$ (Breaker, and Joyce, *Chem. Biol.* 1994, 1, 223-9; Li and Lu, *J. Am. Chem. Soc.* 2000, 122, 10466-7), $Cu^{2+}$ (Carmi et al., *Chem. Biol.* 1996, 3, 1039-1046; Cuenoud et al., *Nature* 1995, 375, 611-614), $Zn^{2+}$ (Santoro et al., *J. Am. Chem. Soc.* 2000, 122, 2433-243; Li et al., *Nucleic Acids Res.* 2000, 28, 481-488), $Co^{2+}$ (Mei et al., *J. Am. Chem. Soc.* 2003, 125, 412-420; Bruesehoff et al., *Comb. Chem. High Throughput Screening* 2002, 5, 327-335), $Mn^{2+}$ (Wang et al., *J. Am. Chem. Soc.* 2003, 125, 6880-6881), and $UO_2^{2+}$ (Liu et al., *Proc. Nat. Acad. Sci. U.S.A.* 2007, 104, 2056-2061).

Fluorophore: A chemical compound, which when excited by exposure to a particular wavelength of light, emits light (fluoresces), for example at a different wavelength of light. Exemplary fluorophores include, but are not limited to: 2-amino-5,6,7-trimethyl-1,8-naphthyridine (ATMND), 3,5-diamino-6-chloro-2-pyrazine carbonitrile (DCPC), fluorescein, rhodamine, malachite green (MG) and dyes belonging to the Alexa Fluor family, as well as derivatives thereof.

A particular type of fluorophore is one whose fluorescence is quenched in the presence of cytosine. In one example, fluorescence is quenched by at least 25% in the presence of cytosine, such as at least 50%, at least 75%, at least 80%, or at least 90%, as compared to an amount of fluorescence in the absence of cytosine (wherein both are in the presence of the appropriate excitation wavelength of light).

Functional nucleic acids (FNAs): Nucleic acid molecules (such as DNA or RNA molecules) that can be used as enzymes (for catalysis) or receptors (for ligand binding), or both. FNAs include ribozyme and DNAzymes (e.g., see Robertson and Joyce, *Nature* 1990, 344:467; Breaker and Joyce, *Chem. Biol.* 1994, 1, 223), aptamers (e.g., see Tuerk and Gold, *Science* 1990, 249, 505) and aptazymes (e.g., see Breaker, *Curr. Opin. Biotechnol.* 2002, 13, 31). Additional examples are provided herein and are known in the art.

Hybridization: Hybridization of a nucleic acid occurs when two nucleic acid molecules undergo an amount of hydrogen bonding to each other. The stringency of hybridization can vary according to the environmental conditions surrounding the nucleic acids, the nature of the hybridization method, and the composition and length of the nucleic acids used. Calculations regarding hybridization conditions required for attaining particular degrees of stringency are discussed in Sambrook et al., *Molecular Cloning: A Laboratory Manual* (Cold Spring Harbor Laboratory Press, Cold Spring Harbor, N.Y., 2001); and Tijssen, *Laboratory Techniques in Biochemistry and Molecular Biology—Hybridization with Nucleic Acid Probes* Part I, Chapter 2 (Elsevier, New York, 1993). The $T_m$ is the temperature at which 50% of a given strand of nucleic acid is hybridized to its complementary strand.

Immobilized: Bound to a surface, such as a solid support. In one embodiment, the solid surface is in the form of a bead or membrane. The surface can include immobilized disclosed sensors that can specifically bind to a target agent. Methods of immobilizing agents, such as nucleic acid molecules, to solid supports are known in the art.

Malachite green (MG): An organic dye with the following structure:

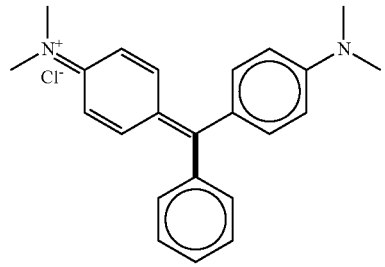

MG has almost no fluorescence when in solution by itself with a quantum yield of about $7.9 \times 10^{-5}$. It becomes fluorescent upon binding to its RNA aptamer.

Nucleic acid molecule: A deoxyribonucleotide or ribonucleotide polymer, which can include analogues of natural nucleotides that hybridize to nucleic acid molecules in a manner similar to naturally occurring nucleotides. A nucleic acid molecule can be single stranded (ss) DNA or RNA molecule or a double stranded (ds) nucleic acid molecule.

Quenching of fluorescence: A reduction of fluorescence. For example, quenching of a fluorophore's fluorescence on a sensor occurs when a quencher molecule (such as cytosine) is present in sufficient proximity to the fluorophore that it reduces the fluorescence signal from the fluorophore.

Sensor: Any device or chemical substance that can be used to detect the presence of a target, such as a target analyte/agent.

Sequence identity: The identity between two or more nucleic acid sequences, or two or more amino acid sequences, is expressed in terms of the identity between the sequences. Sequence identity can be measured in terms of percentage identity; the higher the percentage, the more identical the sequences are. Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations. The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (such as C:\seq1.txt); -j is set to a file containing the second nucleic acid sequence to be compared (such as C:\seq2.txt); -p is set to blastn; -o is set to any desired file name (such as C:\output.txt); -q is set to −1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q −1 -r 2.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

Signal: An indicator, such as a detectable physical quantity from which information can be obtained. In one example, a label emits a signal capable of detection, such as a fluorescent signal.

Target Agent: Any substance whose detection is desired, including, but not limited to, a chemical compound, metal, pathogen, toxin, or protein (such as a cytokine or hormone or antigen), as well as particular cells (such as a cancer cell).

Overview of the Disclosure

This disclosure demonstrates a general vacant site and abasic site approach that makes it possible to design label-free fluorescent sensors based on functional nucleic acid molecules (FNAs) such as catalytic nucleic acids (e.g., DNAzymes, and ribozymes), aptazymes, and aptamers. In some examples it was accomplished by extending a functional nucleic acid molecule (such as a catalytic nucleic acid, e.g., DNAzyme) or an aptamer) with a loop to form a vacant site in the nucleic acid (e.g., DNA) duplex for the controllable binding of a fluorophore, resulting in functional nucleic acid sensors for $Pb^{2+}$, $UO_2^{2+}$, $Hg^{2+}$, and adenosine. These sensors are highly selective to their targets over other similar metal ions or nucleotides, and are very sensitive, with detection limits of 3 nM, 8 nM, 30 nM, and 6 μM for $UO_2^{2+}$, $Pb^{2+}$, $Hg^{2+}$, and adenosine, respectively. Control experiments with FNAs free of vacant site or of mutated inactive sequences reveal that the vacant site and the activity of the FNA (e.g., DNAzyme or aptamer) are crucial for the sensors to exhibit a fluorescence enhancement response in the presence of their targets. The vacant site approach provided herein facilitates the design of other label-free fluorescent sensors for a wide range of analytes.

In other examples, an abasic site (e.g., dSpacer) was introduced into duplex regions of FNAs (e.g., DNAzymes and aptamers), including the 8-17 DNAzyme and adenosine aptamer, for label-free fluorescent detection of $Pb^{2+}$ and adenosine, respectively. The abasic site binds an extrinsic fluorescent compound (e.g., 2-amino-5,6,7-trimethyl-1,8-naphthyridine (ATMND)) and quenches its fluorescence. Addition of the target (such as $Pb^{2+}$) enables the DNAzyme (or other FNA) to cleave its substrate and release ATMND from DNA duplex, recovering the fluorescence of ATMND. For the aptamer, the presence of the target (such as adenosine) induces structural switching of the aptamer, resulting in the release of ATMND from the DNA duplex and a subsequent fluorescence enhancement. Under optimized conditions, this label-free method exhibited detection limits of 4 nM for $Pb^{2+}$ and 3.4 μM for adenosine, which are even lower than those of the corresponding labeled-DNAzyme and aptamer sensors. These low detection limits have been obtained without compromising any of the selectivity of the sensors. The dynamic range of the adenosine sensor was tuned by varying the number of hybridized base-pairs in the aptamer duplex. Thus, this abasic site approach can be applied for label-free detection and quantification of a broad range of analytes using other DNAzymes and aptamers.

In yet other examples, an abasic site (e.g., dSpacer) was introduced into a substrate strand of an FNA (e.g., DNAzyme and aptazyme) which formed a molecular beacon (MB), including the 8-17 DNAzyme and adenosine aptazyme, for label-free fluorescent detection of $Pb^{2+}$ and adenosine, respectively. Such methods can be used for designing label-free catalytic and molecular beacons (CAMBs) that include an abasic site, and application of this approach to the rational design of label-free sensors. The abasic site binds an extrinsic fluorescent compound (e.g., 2-amino-5,6,7-trimethyl-1,8-naphthyridine (ATMND)) and quenches its fluorescence. Addition of the target (such as $Pb^{2+}$) enables the DNAzyme (or other FNA) to cleave its substrate and release ATMND from MB portion, recovering the fluorescence of ATMND. For the aptazyme, the presence of the target (such as adenosine) induces structural switching of the aptazyme, and activated the DNAzyme's activity, resulting in the release of ATMND from the MB portion and a subsequent fluorescence enhancement. Under optimized conditions, this label-free method exhibited detection limits of 3.8 nM for $Pb^{2+}$ and 1.4 μM for adenosine, which are even lower than those of the corresponding labeled-DNAzyme and aptamer sensors. These low detection limits have been obtained without compromising any of the selectivity of the sensors. The dynamic range of the sensors was tuned by varying the number of hybridized base-pairs in the duplex formed between the enzyme strand and the substrate strand of the FNA. Thus, this label-free CAMB approach can be applied for label-free detection and quantification of a broad range of analytes using other DNAzymes, aptamers and aptazymes.

Thus, for both the abasic site and vacant site approach, the active sequence of the functional molecule (e.g., DNAzyme, aptazyme, or aptamer) is preserved, and the abasic (e.g., dSpacer) or vacant site is situated such that it is opposite to one C in the nucleic acid molecule duplex. This C can be distant from the active sequence of the functional molecule (e.g., DNAzyme or aptamer) to avoid the possible influence of activity, and also, the DNA duplex part where the C-dspacer or C-vacant-site dehybridizes when target interacts with the functional molecule (e.g., DNAzyme or aptamer).

The disclosure also provides label-free fluorescent aptamer sensors based on the regulation of malachite green (MG) fluorescence. In a particular example, an adenosine sensor is disclosed that has comparable sensitivity and selectivity to other labeled adenosine aptamer-based sensors. The sensor includes free MG, an aptamer strand (for example containing an adenosine aptamer) linked to an MG aptamer, and a bridging strand that partially hybridizes to the aptamer strand. Such hybridization prevents MG from binding to MG aptamer, resulting in low fluorescence of MG in the absence of the target, such as adenosine. Presence of the target agent, such as adenosine, causes the aptamer strand to bind the target, weakening the hybridization of the aptamer strand with the bridging strand, making it possible for MG to bind to the aptamer strand and exhibits high fluorescence intensity. Since this design is based purely on nucleic acid hybridization, it can be generally applied to other aptamers, DNAzymes and ribozymes for the label-free detection of a broad range of analytes.

Sensors

The disclosure provides label-free nucleic acid-based sensors that can be used to detect the presence of a target agent. The sensors can include DNA molecules, RNA molecules or both, for example the sensor can include nucleotides, ribonucleotides, or both. The disclosed sensors include a functional nucleic acid molecule, such as a catalytic nucleic acid (e.g., DNAzyme, ribozyme, or aptazyme) or aptamer, and can further include a vacant site or abasic site that can bind to a fluorophore. Upon interaction of the functional nucleic acid molecule with its target, the conformation of the sensor changes or it undergoes catalytic cleavage such that a fluorescent signal is generated, which can be detected. In particular examples, the sensors include no more than 1000 bases (nucleotides or ribonucleotides), such as or, such as 10-1000, 20-1000, 30-1000, 40-1000, 50-1000, 20-500, 20-200, 20-100, 50-100, 20-80, or 40-80 nucleotides or ribonucleotides.

Label-Free Fluorescent Sensors Using a Vacant Site

The disclosure provides label-free FNA sensors using unmodified nucleic acids containing a vacant site, and methods of making such sensors. In one example, such sensors include a catalytic nucleic acid (e.g., DNAzyme or ribozyme) specific for a target agent, which includes both an enzyme nucleic acid strand and a substrate nucleic acid strand. In particular examples, both strands are composed of DNA. However, one will recognize that the stands can be a combination of RNA and DNA, or just RNA. The enzyme nucleic acid strand includes a 5'- end and a 3'-end and an active site specific for a target agent. The substrate nucleic acid strand includes a 5'-end and a 3'-end, as well as nucleotides at the 5'-end of the substrate nucleic acid strand that permit formation of a loop at the 5'-end of the substrate nucleic acid strand. The substrate nucleic acid strand has sufficient complementarity to the enzyme nucleic acid strand such that it hybridizes with the enzyme nucleic acid strand, for example under high stringency conditions. In some examples the substrate nucleic acid strand has at least 80%, at least 90%, at least 95%, at least 97% or at least 98% complementarity to the enzyme nucleic acid strand. In some examples, least one pair of nucleotides are mismatched upon hybridization of the substrate nucleic acid strand with the enzyme nucleic acid strand, such as 1, 2, 3, 4, or 5 mismatches. Such hybridization between the enzyme nucleic acid strand and the substrate nucleic acid strand forms a duplex molecule containing a vacant site (e.g., there is no nucleotide present at that position, that is, the whole nucleotide is absent) between the 3'-end of the enzyme nucleic acid strand and the 5'-end of the substrate nucleic acid strand, wherein the vacant site is opposite to a cytosine present in the substrate nucleic acid strand. In the absence of the target agent, fluorescence of a fluorophore bound or non-covalently attached to the vacant site is quenched, and wherein in the presence of the target agent, catalytic cleavage of substrate nucleic acid strand perturbs the vacant site and releases the fluorophore bound to the vacant site resulting in increased fluorescence. In one example, the fluorophore is 2-amino-5, 6,7-trimethyl-1,8-naphthyridin (ATMND). This change in fluorescence permits detection of test agents that are specific for the catalytic nucleic acid used.

Figure 20A:
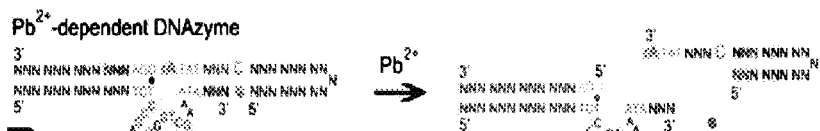
Figure 20B:
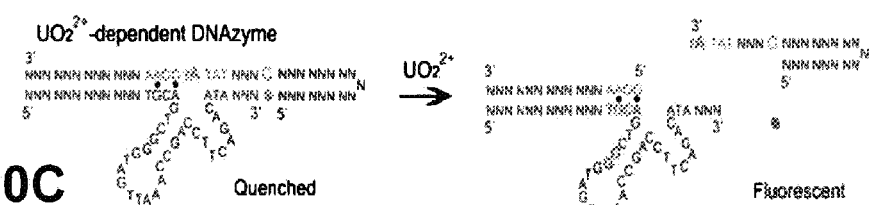

A general overview of this method is shown in FIGS. 20A and 20B. As shown in FIGS. 20A and 20B, with the knowledge of a DNAzyme sequence for a target agent of interest, a sensor of the present disclosure can be generated. The sensor includes DNAzyme specific for a target agent (such as lead or uranium). The DNAzyme includes both an enzyme nucleic acid strand (e.g., SEQ ID NO: 43 or 45) and a substrate nucleic acid strand (e.g., SEQ ID NO: 44 or 46). The sequence of the cleavage site (in the substrate nucleic acid strand, for example nucleotides AGG rA TAT in FIG. 20A nucleotides 23-28 of SEQ ID NO: 43) and the active site in the enzyme nucleic acid strand (for example nucleotides TCTCCGAGC-CGGTCGAAATA in FIG. 20A; nucleotides 13-32 of SEQ ID NO: 43) is unaltered. The "N" in the FIGS. 20A and B indicates that the nucleotide at that position can be any one of A, G, T, and C, as long as the secondary structure (loops, duplex regions, etc.) of the DNA duplex is maintained. Also, the number of N at each place can be varied (for example, NNN can be changed to NNNNNN, as long as the secondary structure is maintained). The nucleotides marked as A, G, T and C are not altered to maintain the activity of DNAzyme and the binding of the fluorophore (opposite to C in the substrate nucleic acid strand).

In particular examples the vacant site is flanked by guanines present on a 3'-nucleotide of the enzyme nucleic acid strand and a 5'-nucleotide of the substrate nucleic acid strand.

The loop formed at the 5'-end of the substrate nucleic acid strand can be composed of at least 3 nucleotides, as long as the loop is stable in the absence of the target agent, and the cytosine in the substrate nucleic acid strand is opposite to the vacant site. In some examples, the loop is formed by at least 5, at least 6, at least 7, at least 9, at least 11, at least 13, at least 15, at least 17 or at least 19 nucleotides, such as 3 to 9 or 6 to 17 nucleotides. Any nucleotide sequence can be used to form the loop, as long as there is sufficient complementarity to form the loop as long as the loop is stable in the absence of the target agent, and the cytosine in the substrate nucleic acid strand is opposite to the vacant site.

Although particular sensors are disclosed herein, the disclosure is not limited to the use of those exact sequences. One skilled in the art will appreciate that variations can be made to these sequences, while retaining the desired characteristics of the sensors. In one example, the enzyme nucleic acid strand comprises at least 80%, at least 90%, at least 95%, or at least 98% sequence identity to SEQ ID NO: 1, the substrate nucleic acid molecule comprises at least 80%, at least 90%, at least 95%, or at least 98% sequence identity to SEQ ID NO: 2, and the target agent is lead. In another example, the enzyme nucleic acid strand comprises at least 80%, at least 90%, at least 95%, or at least 98% sequence identity to SEQ ID NO: 12, the substrate nucleic acid molecule comprises at least 80%, at least 90%, at least 95%, or at least 98% sequence identity to SEQ ID NO: 13, and the target agent is uranium.

FIG. 22 shows DNAzyme sequences specific for $Mg^{2+}$, lead, or $Cu^{2+}$, which can be modified using the methods disclosed herein to generate a label-free sensor of the disclosure. For example, FIG. 22 shows the generic sequences for enzyme strands that include the particular active site sequence specific for the target, and the partial generic substrate strands that include a cleavage site that can be used in combination with the enzyme strands. The substrate strands can be extended at their 5'-end to form a loop as described herein.

In one example, such sensors include an aptamer specific for a target agent comprising a 5'-end and a 3'-end, a first nucleic acid molecule having a 5'-end and a 3'-end, wherein the 5'-end of the aptamer is attached to the 3'-end of the first nucleic acid molecule. The 3'-end of the first nucleic acid can include the nucleotide sequence NCN, wherein N is any nucleotide, and the 5'-end of the first nucleic acid molecule forms a loop. The sensor also includes a second nucleic acid molecule having a 5'-end and a 3'-end. The second nucleic acid molecule is hybridized to the 5'-end of the aptamer, thereby forming a duplex nucleic acid molecule that includes a vacant site (e.g., no nucleotide present at that position) between the 5'-end of the first nucleic acid molecule and the 3'-end of the second nucleic acid molecule. The vacant site is opposite to the cytosine of the NCN sequence of the first nucleic acid molecule. The second nucleic acid molecule has sufficient complementarity to the 5'-end of the aptamer (such as nucleotides 2 to 7 at the 5'-end) such that it hybridizes with the aptamer, for example under high stringency conditions. In some examples, at least a portion of the 5'-end of the aptamer (such as at least 3, at least 4, at least 5 or at least 6 nucleotides in the first third of the aptamer sequence) has at least 80%, at least 90%, at least 95%, at least 97% or at least 98% complementarity to the second nucleic acid molecule. In some examples, least one pair of nucleotides are mismatched upon hybridization of the second nucleic acid molecule with the aptamer, such as 1, 2, 3, 4, or 5 mismatches. In the absence of the target agent, fluorescence of a fluorophore bound or noncovalently attached to the vacant site is quenched, and wherein in the presence of the target agent, a conformational change in the aptamer perturbs the vacant site and release the fluorophore bound to the vacant site resulting in increased fluorescence. This change in fluorescence permits detection of test agents that are specific for the aptamer used.

Figure 20C:
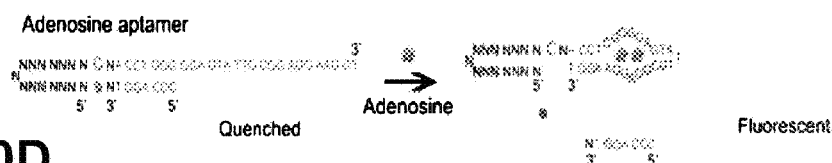
Figure 20D:
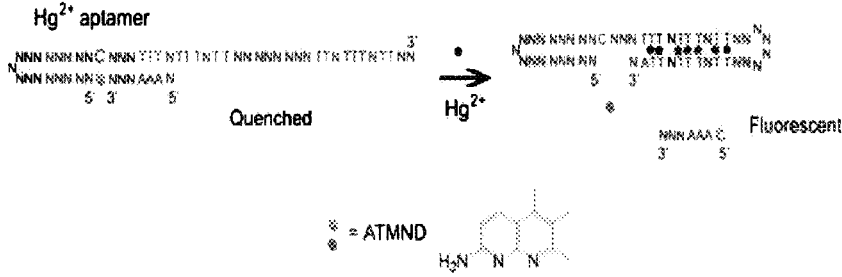

A general overview of this method is shown in FIGS. 20C and 20D. As shown in FIGS. 20C and 20D, with the knowledge of an aptamer sequence for a target agent of interest, a sensor of the present disclosure can be generated. The sensor includes an aptamer specific for a target agent (such as adenosine or mercury). The sensor includes the aptamer sequence, which has attached thereto at its 5'-end the 3'-end of a first nucleic acid the sequence NCN, such as CCC, wherein the middle C is opposite to a vacant site in the sensor. The other portion of the first nucleic acid molecule forms a loop. A second nucleic acid molecule (for examples SEQ ID NO: 48 in FIG. 20C, and SEQ ID NO: 50 in FIG. 20D) hybridizes with the aptamer. The "N" in FIGS. 20C and D indicates that the nucleotide at that position can be any one of A, G, T, and C, as long as the secondary structure (loops, duplex regions, etc.) of the nucleic acid duplex (e.g., DNA duplex) is maintained. Also, the number of N at each place can be varied (for example, NNN can be changed to NNNNNN, as long as the secondary structure is maintained). The nucleotides marked as A, G, T and C are not altered to maintain the activity of aptamer and the binding of the fluorophore (opposite to C in the substrate nucleic acid strand).

In particular examples the vacant site is flanked by guanines present on a 3'-nucleotide of the second nucleic acid molecule and a 5'-nucleotide of the first nucleic acid molecule.

The loop formed at the 5'-end of the first nucleic acid molecule can be composed of at least 3 nucleotides, as long as the loop is stable in the absence of the target agent, and the cytosine in the first nucleic acid molecule is opposite to the vacant site. In some examples, the loop is formed by at least 5, at least 6, at least 7, at least 9, at least 11, at least 13, at least 15, at least 17 or at least 19 nucleotides, such as 3 to 9, 7 to 17, or 6 to 17 nucleotides. Any nucleotide sequence can be used to form the loop, as long as there is sufficient complementarity to form the loop as long as the loop is stable in the absence of the target agent, and the cytosine in the substrate nucleic acid strand is opposite to the vacant site.

Although particular sensors are disclosed herein, the disclosure is not limited to the use of those exact sequences. One skilled in the art will appreciate that variations can be made to these sequences, while retaining the desired characteristics of the sensors. In one example, the aptamer comprises at least 80%, at least 90%, at least 95%, or at least 98% sequence identity to nucleotides 18 to 44 of SEQ ID NO: 5, the first nucleic acid molecule comprises at least 80%, at least 90%, at least 95%, or at least 98% sequence identity to nucleotides 1-17 of SEQ ID NO: 5, the second nucleic acid molecule comprises at least 80%, at least 90%, at least 95%, or at least 98% sequence identity to SEQ ID NO: 9, and the target agent is adenosine. In another example, the aptamer comprises at least 80%, at least 90%, at least 95%, or at least 98% sequence identity to nucleotides 18 to 50 of SEQ ID NO: 14, the first nucleic acid molecule comprises at least 80%, at least 90%, at least 95%, or at least 98% sequence identity to nucleotides 1-17 of SEQ ID NO: 14, the second nucleic acid molecule comprises at least 80%, at least 90%, at least 95%, or at least 98% sequence identity to SEQ ID NO: 15, and the target agent is mercury.

Label-Free Fluorescent Sensors Using an Abasic Site

The disclosure provides label-free fluorescent functional DNA sensors containing an abasic site (e.g., only the phosphodiester backbone of the nucleotide present, the base is absent), and methods of making such sensors. In one example, such sensors include a catalytic nucleic acid (e.g., DNAzyme or RNAzyme) specific for a target agent, wherein the catalytic nucleic acid has an enzyme nucleic acid strand and a substrate nucleic acid strand. The enzyme nucleic acid strand comprises a 5'-end and a 3'-end and an active site specific for a target agent. A nucleotide 2 to 6 nucleotides from the 3'-end of the enzyme nucleic acid strand (such as a nucleotide 2, 3, 4, 5, or 6 nucleotides from the 3'-end of the enzyme nucleic acid strand) is replaced by an abasic site (such as a dSpacer, Spacer C3, Spacer C6 or Spacer C12). In particular examples the abasic site is flanked by guanines present on the enzyme nucleic acid strand. The substrate nucleic acid strand has a 3'-end and a 5'-end, and a cytosine 2 to 6 nucleotides from the 5'-end of the substrate nucleic acid strand. In particular examples, the substrate nucleic acid strand includes a cleavage site (such as a cleavage site that includes an RNA nucleotide linkage, for example adenine ribonucleotide (rA)) such that upon hybridization of the substrate nucleic acid strand to the enzyme nucleic acid strand, the catalytic site is opposite to the active site of the enzyme strand. The substrate nucleic acid strand has sufficient complementarity to the enzyme nucleic acid strand such that it hybridizes with the enzyme nucleic acid strand, for example under high stringency conditions. In some examples the substrate nucleic acid strand has at least 80%, at least 90%, at least 95%, at least 95%, or at least 98% complementarity to the enzyme nucleic acid strand. In some examples, least one pair of nucleotides are mismatched upon hybridization of the substrate nucleic acid molecule with the enzyme nucleic acid strand, such as 1, 2, 3, 4, or 5 mismatches. Such hybridization results in the abasic site in the enzyme nucleic acid strand being opposite to the cytosine 2 to 6 nucleotides from the 5'-end of the substrate nucleic acid strand. In the absence of the target agent, fluorescence of a fluorophore bound to the abasic site is quenched, and wherein in the presence of the target agent, catalytic cleavage of substrate nucleic acid strand perturbs the vacant site and releases the fluorophore bound to the abasic site resulting in increased fluorescence. This change in fluorescence permits detection of test agents that are specific for the catalytic nucleic acid (e.g., DNAzyme or RNAzyme) used.

A general overview of this method is shown in FIG. 21A. As shown in FIG. 21A, with the knowledge of a DNAzyme sequence for a target agent of interest, a sensor of the present disclosure can be generated. The sensor includes DNAzyme specific for a target agent (such as lead). The DNAzyme includes both an enzyme nucleic acid strand (e.g., SEQ ID NO: 51) and a substrate nucleic acid strand (e.g., SEQ ID NO: 52). The sequence of the cleavage site (in the substrate nucleic acid strand, for example nucleotides TAT rA GGA in FIG. 21A; nucleotides 6-12 of SEQ ID NO: 52) and the active site in the enzyme nucleic acid strand (for example nucleotides TCTCCGAGCCGGTCGAAATA in FIG. 21A; nucleotides 13-32 of SEQ ID NO: 51) is unaltered. The "N" in the FIG. 21A indicates that the nucleotide at that position can be any one of A, G, T, and C, as long as the secondary structure (loops, duplex regions, etc.) of the DNA duplex is maintained. Also, the number of N at each place can be varied (for example, NNN can be changed to NNNNNN, as long as the secondary structure is maintained). The nucleotides marked as A, G, T and C are not altered to maintain the activity of DNAzyme and the binding of the fluorophore (opposite to C in the substrate nucleic acid strand).

Although particular sensors are disclosed herein, the disclosure is not limited to the use of those exact sequences. One skilled in the art will appreciate that variations can be made to these sequences, while retaining the desired characteristics of the sensors. In one example, the enzyme nucleic acid strand comprises at least 80%, at least 90%, at least 95%, or at least 98% sequence identity to SEQ ID NO: 16, the substrate nucleic acid molecule comprises at least 80%, at least 90%, at least 95%, or at least 98% sequence identity to SEQ ID NO: 18, and the target agent is lead.

In one example, such sensors include an aptamer specific for a target agent comprising a 3'-end and a 5'-end, a first nucleic acid molecule comprising at least four nucleotides (such as at least 6 nucleotides, for example 4, 5, 6, 7, 8, 9, or 10 nucleotides) attached to the 3'-end of the aptamer, and a second nucleic acid molecule comprising a 5'-end and a 3'-end and an abasic site. The second nucleic acid molecule has complementarity to the aptamer and to the first nucleic acid molecule, wherein the second nucleic acid molecule is hybridized to the aptamer and to the first nucleic acid molecule, resulting in the abasic site being opposite to a cytosine in the aptamer or first nucleic acid molecule. The second nucleic acid molecule has sufficient complementarity to the 3'-end of the aptamer (such as nucleotides 1 to 7 at the 3'-end) and the portion of the first nucleic acid attached to the aptamer sequence (such as complementarity to at least 75%, at least 80%, at least 90% or at least 95% of the nucleotides of the first nucleic acid sequence, for example 3, 4, 5, 6, 7, 8, 9, or 10 of the nucleotides of the first nucleic acid sequence) such that it hybridizes with the aptamer, for example under high stringency conditions. In the absence of the target agent, fluorescence of a fluorophore bound to the vacant site is quenched, and wherein in the presence of the target agent, a conformational change in the aptamer perturbs the abasic site and release the fluorophore bound to the abasic site resulting in increased fluorescence. This change in fluorescence permits detection of test agents that are specific for the aptamer used.

A general overview of this method is shown in FIG. 21B. As shown in FIG. 21B, with the knowledge of an aptamer sequence for a target agent of interest, a sensor of the present disclosure can be generated. The sensor includes an aptamer specific for a target agent (such as adenosine). The sensor includes the aptamer sequence, which has attached thereto at its 3'-end the first nucleic acid the sequence, wherein a C in the aptamer sequence or the first nucleic acid sequence is opposite to an abasic site in the sensor. A second nucleic acid molecule (for example the bottom strand in the top image of FIG. 21B) hybridizes with the aptamer and the first nucleic acid molecule. The "N" in FIG. 21B indicates that the nucleotide at that position can be any one of A, G, T, and C, as long as the secondary structure (loops, duplex regions, etc.) of the DNA duplex is maintained. Also, the number of N at each place can be varied (for example, NNN can be changed to NNNNNN, as long as the secondary structure is maintained). The nucleotides marked as A, G, T and C are not altered to maintain the activity of aptamer and the binding of the fluorophore (opposite to C in the substrate nucleic acid strand).

In particular examples the aptamer site is flanked by at least one guanine present in the second nucleic acid molecule.

Although particular sensors are disclosed herein, the disclosure is not limited to the use of those exact sequences. One skilled in the art will appreciate that variations can be made to these sequences, while retaining the desired characteristics of the sensors. In one example, the aptamer comprises at least 80%, at least 90%, at least 95%, or at least 98% sequence identity to nucleotides 9-35 of SEQ ID NO: 19, the first nucleic acid molecule comprises at least 80%, at least 90%, at least 95%, or at least 98% sequence identity to nucleotides 1-8 of SEQ ID NO: 19, and the second nucleic acid molecule comprises at least 80%, at least 90%, at least 95%, or at least 98% sequence identity to SEQ ID NO: 20, and the target agent is adenosine.

FIG. 23 shows how a theophylline aptamer can be modified (e.g., by introduction of an abasic site) to generate a label-free sensor of the present disclosure.

Label-Free Catalytic and Molecular Beacons

The disclosure provides label-free catalytic and molecular beacons (CAMBs) that include an abasic site or a vacant site, and methods of using this approach to the rational design of label-free sensors. Although specific examples are provided for detecting lead with a DNAzyme and adenosine with an aptazyme, based on the teachings herein, one skilled in the art will appreciate that other functional nucleic acid molecules can be similarly modified, such as ribozymes and RNA aptamers, to detect the target of interest. An aptazyme is a combination of aptamer and DNAzyme, and the binding of the target to the aptamer part can activate or inhibit the enzymatic activity of the DNAzyme portion.

In one example, such sensors include a catalytic nucleic acid molecule (e.g., DNAzyme, aptazyme or ribozyme) specific for a target agent, wherein the catalytic nucleic acid has an enzyme nucleic acid strand and a substrate nucleic acid strand. The enzyme nucleic acid strand includes a 5'-end and a 3'-end and an active site specific for a target agent (such as a heavy metal or other molecule). The substrate nucleic acid strand includes a 3'-end and a 5'-end, as well as the abasic site and a cleavage site. The substrate nucleic acid strand includes a cytosine 2 to 6 nucleotides from one end (such as 2, 3, 4, 5, or 6 nucleotides from the 3'-end or 5'-end of the substrate nucleic acid strand), and a nucleotide 2 to 6 nucleotides (such as a 2, 3, 4, 5, or 6 nucleotides from the 3'-end or 5'-end of the substrate nucleic acid strand) from the other end of the substrate nucleic acid strand (5'-end if the cytosine is 2 to 6 nucleotides from the 3'-end or the 3'-end if the cytosine is 2 to 6 nucleotides from the 5'-end) is replaced by an abasic site (such as a dSpacer, Spacer C3, Spacer C6 or Spacer C12). In particular examples the abasic site is flanked by guanines present on the substrate nucleic acid strand. For example, the substrate nucleic acid strand can include a cytosine 2 to 6 nucleotides from the 3'-end (or 5'-end), and a nucleotide 2 to 6 nucleotides from the other end of the substrate nucleic acid strand is replaced by an abasic site (5'-end if the cytosine is 2 to 6 nucleotides from the 3'-end or the 3'-end if the cytosine is 2 to 6 nucleotides from the 5'-end). In some examples, the sensor includes a fluorophore bound to the abasic site.

The substrate nucleic acid strand has sufficient complementarity to the enzyme nucleic acid strand such that it hybridizes with a least a portion the enzyme nucleic acid strand, for example under high stringency conditions. In some examples the substrate nucleic acid strand has at least 80%, at least 90%, at least 95%, at least 97%, at least 98%, at least 99%, or 100% complementarity to the region of the enzyme nucleic acid strand that flanks the active site (referred to as the "arms"). In some examples, least one pair of nucleotides are mismatched upon hybridization of the substrate nucleic acid strand with the enzyme nucleic acid strand, such as 1, 2, 3, 4, or 5 mismatches. The substrate nucleic acid strand can also include a cleavage site (such as one that includes an RNA nucleotide linkage, for example adenine ribonucleotide (rA)), such that when the substrate nucleic acid strand hybridizes to the enzyme nucleic acid strand, the cleavage site is flanked by nucleotides of the substrate nucleic which hybridize to the "arms" of the enzyme nucleic acid strand, such as 6 to 10 nucleotides (such as 6, 7, 8, 9 or 10 nucleotides) on the 5'-end and 6 to 10 nucleotides (such as 6, 7, 8, 9 or 10 nucleotides) on the 3'-end of the enzyme nucleic acid strand. Such hybridization forms a molecular beacon of the substrate strand that includes a stem region. In particular examples the stem region is 5 to 9 base pairs in length, such as 5, 6, 7, 8, or 9 base pairs in length. The stem region includes an abasic site opposite to the cytosine 2 to 6 nucleotides from the 3'-end (or 5'-end) of the substrate nucleic acid strand. In the absence of the target agent, fluorescence of a fluorophore bound to the abasic site is quenched, and wherein in the presence of the target agent, catalytic cleavage of substrate nucleic acid strand perturbs the vacant site and releases the fluorophore bound to the abasic site resulting in increased fluorescence. This change in fluorescence permits detection of test agents that are specific for the catalytic nucleic acid (e.g., DNAzyme, aptazyme, or RNAzyme) used.

A general overview of this method for DNAzymes is shown in FIG. 21C. As shown in FIG. 21C, with the knowledge of a DNAzyme sequence for a target agent of interest, a label-free CAMB sensor of the present disclosure can be generated. The sensor includes DNAzyme specific for a target agent (such as lead or other heavy metal). The DNAzyme includes both an enzyme nucleic acid strand (e.g., SEQ ID NO: 73) and a substrate nucleic acid strand (e.g., SEQ ID NO: 78). The sequence of the cleavage site (in the substrate nucleic acid strand) and the active site in the enzyme nucleic acid strand (for example nucleotides aagc tggccgagcc in FIG. 21C; nucleotides 7-20 of SEQ ID NO: 95) is unaltered. The "N" in the FIG. 21C indicates that the nucleotide at that position can be any one of A, G, T, and C, as long as the secondary structure (loops, duplex regions, etc.) of the DNA duplex is maintained. Also, the number of N at each place can be varied (for example, NNN can be changed to NNNNNN, as long as the secondary structure is maintained). The nucleotides marked as A, G, T and C are not altered to maintain the activity of DNAzyme and the binding of the fluorophore (opposite to C in the substrate nucleic acid strand).

A general overview of this method for aptazymes is shown in FIG. 21D. As shown in FIG. 21D, with the knowledge of an aptazyme sequence for a target agent of interest, a label-free CAMB sensor of the present disclosure can be generated. The sensor includes an aptazyme specific for a target agent (such as adenosine). The aptazyme includes both an enzyme nucleic acid strand (e.g., SEQ ID NO: 81) and a substrate nucleic acid strand (e.g., SEQ ID NO: 78). The sequence of the cleavage site (in the substrate nucleic acid strand) and the active site in the enzyme nucleic acid strand (for example nucleotides tgt acccacgaag gaggcgttat gagggggtct agc in FIG. 21D; nucleotides 8-45 of SEQ ID NO: 97) is unaltered. The "N" in the FIG. 21D indicates that the nucleotide at that position can be any one of A, G, T, and C, as long as the secondary structure (loops, duplex regions, etc.) of the DNA duplex is maintained. Also, the number of N at each place can be varied (for example, NNN can be changed to NNNNNN, as long as the secondary structure is maintained). The nucleotides marked as A, G, T and C are not altered to maintain the activity of DNAzyme and the binding of the fluorophore (opposite to C in the substrate nucleic acid strand).

Although particular sensors are disclosed herein, the disclosure is not limited to the use of those exact sequences. One skilled in the art will appreciate that variations can be made to these sequences, while retaining the desired characteristics of the sensors. In one example, the enzyme nucleic acid strand comprises at least 80%, at least 90%, at least 95%, or at least 98% sequence identity to SEQ ID NO: 73, 74 or 75, the substrate nucleic acid molecule comprises at least 80%, at least 90%, at least 95%, or at least 98% sequence identity to SEQ ID NO: 77 or 78, and the target agent is lead. In one example, the enzyme nucleic acid strand comprises at least 80%, at least 90%, at least 95%, or at least 98% sequence identity to SEQ ID NO: 80, 81 or 82, and the substrate nucleic acid molecule comprises at least 80%, at least 90%, at least 95%, or at least 98% sequence identity to SEQ ID NO: 77 or 78, and the target agent is adenosine.

Fluorophores

The sensors discussed above that include a vacant site or an abasic site can further include a fluorophore attached (e.g., through non-covalent binding) to the vacant site or abasic site. In particular examples, the fluorophore is quenched in the presence of cytosine. Exemplary fluorophores that can be used in the disclosed sensors include but are not limited to: 2-amino-5,6,7-trimethyl-1,8-naphthyridine (ATMND), 3,5-diamino-6-chloro-2-pyrazine carbonitrile (DCPC), fluorescein, rhodamine, malachite green (MG) and dyes belonging to the Alexa Fluor family, and their derivatives.

Label-Free Fluorescent Aptamer Sensors Based on the Regulation of Malachite Green (MG) Fluorescence The disclosure also provides label-free fluorescent aptamer sensors based on the regulation of MG fluorescence. In a particular example, the sensor includes an aptamer specific for a target agent and a malachite green RNA aptamer, wherein the malachite green RNA aptamer is linked to the aptamer specific for the target agent. The sensor also includes a bridging nucleic acid strand, wherein the bridging strand is complementary to a region that includes consecutive nucleotides present in the aptamer specific for the target and the MG RNA aptamer. For example, the bridge includes nucleotides that are complementary to the region where the MG RNA aptamer is linked to the aptamer specific for the target agent. The number of nucleotides optimal for a particular sensor can be determined using the methods provided in the examples below. In some examples, the bridge includes at least 6 nucleotides, for example at least 7, 8, 9, 10, 11, 12, 13, 14, 15, 16, 17, 18, 19 or 20 nucleotides. The number of nucleotides complementary to the MG RNA aptamer and to the aptamer specific for the target agent does not need to be identical. In some examples, a bridge sequence is selected by determining the fold of the fluorescence increase in the presence of the target, wherein bridge sequence having a greater increase in fluorescence than other bridge sequences is selected (for example see FIG. 17 and Example 14).

Upon hybridization of the bridging nucleic acid strand to the aptamer specific for the target and the MG RNA aptamer forms a stable complex to prevent the MG aptamer strand from binding MG if there is no target agent is present. In the absence of the target agent, fluorescence from MG is decreased due to an inability of MG to bind to MG RNA aptamer, and wherein in the presence of the target agent, a conformational change in the aptamer specific for the target releases the bridging strand resulting in increased MG fluorescence.

Although particular sensors are disclosed herein, the disclosure is not limited to the use of those exact sequences. One skilled in the art will appreciate that variations can be made to these sequences, while retaining the desired characteristics of the sensors. In one example, the wherein the aptamer specific for the target comprises at least 80%, at least 90%, at least 95%, or at least 98% sequence identity to SEQ ID NO: 26, the MG RNA aptamer comprises at least 80%, at least 90%, at least 95%, or at least 98% sequence identity to SEQ ID NO: 27, the bridging strand comprises at least 80%, at least 90%, at least 95%, or at least 98% sequence identity to SEQ ID NO: 33, and the target agent is adenosine.

Functional Nucleic Acids

Besides proteins, nucleic acids have also been found to have catalytic activities in recent years. The catalytic active nucleic acids can be catalytic DNA/RNA, also known as DNAzymes/RNAzymes, deoxyribozymes/ribozymes, and DNA enzymes/RNA enzymes. Catalytic active nucleic acids can also contain modified nucleic acids. Nucleic acids may be selected to bind to a wide range of analytes with high affinity and specificities. These binding nucleic acids are known as aptamers. Such functional nucleic acid molecules can be modified using the methods provided herein to generate label-free sensors.

DNAzymes, ribozymes, and aptamer sequences for particular target agents are known in the art. Aptamers are nucleic acids (such as DNA or RNA) that bind to a specific target, such as a target agent provided herein. For example, the adenosine aptamer binds adenosine as its corresponding target. In yet another example, the molecule that specifically binds to the target agent is a DNAzyme or catalytic DNA or DNA enzymes. DNAzymes are DNA molecules that have enzymatic activities. They are similar to ribozymes, but consist of DNA instead of RNA. Therefore DNAzymes are also called deoxyribozymes, catalytic DNA, or DNA enzymes. Like ribozymes, DNAzymes require a co-factor, such as a metal ion, to have catalytic activity. Thus, DNAzymes can also be used to detect target agent metal ions. A ribozyme is an RNA molecule with catalytic activity, for example RNA splicing activity. When ribozymes function, they often require a cofactor, such as metal ions (e.g., $Mg^{2+}$) for their enzymatic activity. Such a cofactor can be the target agent detected based on ribozyme activity. Thus, as cofactors support ribozyme activity and ribozyme activity can be an indicator of the presence of the cofactor, or target agent. Aptazymes are the combination of aptamer and DNAzymes or ribozymes. Aptazymes work when the target agent binds to the aptamer which either triggers DNAzyme/ribozyme activities or inhibits DNAzyme/ribozyme activities.

In vitro selection methods (for example Systematic Evolution of Ligands by EXponential enrichment (SELEX)) can be used to obtain aptamers and DNAzymes for a wide range of target molecules with exceptionally high affinity, having dissociation constants as high as in the picomolar range (Brody and Gold, *J. Biotechnol.* 74: 5-13, 2000; Jayasena, *Clin. Chem.*, 45:1628-1650, 1999; Wilson and Szostak, *Anna. Rev. Biochem.* 68: 611-647, 1999). For example, aptamers and DNAzymes have been developed to recognize metal ions such as Zn(II) (Ciesiolka et al., *RNA* 1: 538-550, 1995) and Ni(II) (Hofmann et al., *RNA*, 3:1289-1300, 1997); nucleotides such as adenosine triphosphate (ATP) (Huizenga and Szostak, *Biochemistry*, 34:656-665, 1995); and guanine (Kiga et al., *Nucleic Acids Res.*, 26:1755-60, 1998); co-factors such as NAD (Kiga et al., *Nucleic Acids Res.*, 26:1755-60, 1998) and flavin (Lauhon and Szostak, *J. Am. Chem. Soc.*, 117:1246-57, 1995); antibiotics such as viomycin (Wallis et al., *Chem. Biol.* 4: 357-366, 1997) and streptomycin (Wallace and Schroeder, *RNA* 4:112-123, 1998); proteins such as HIV reverse transcriptase (Chaloin et al., *Nucleic Acids Res.*, 30:4001-8, 2002) and hepatitis C virus RNA-dependent RNA polymerase (Biroccio et al., *J. Virol.* 76:3688-96, 2002); toxins such as cholera whole toxin and staphylococcal enterotoxin B (Bruno and Kiel, *BioTechniques*, 32: pp. 178-180 and 182-183, 2002); and bacterial spores such as the anthrax (Bruno and Kiel, *Biosensors & Bioelectronics*, 14:457-464, 1999).

Methods of identifying a functional DNA that is specific for a particular target agent are routine in the art and have been described in several patents (all herein incorporated by reference). For example U.S. Pat. Nos. 7,192,708; 7,332,283; 7,485,419; 7,534,560; and 7,612,185, and US Patent Publication Nos. 20070037171 and 20060094026, describe methods of identifying functional DNA molecules that can bind to particular ions, such as lead and cobalt. In addition, specific examples are provided. Although some of the examples describe functional DNA molecules with fluorophores, such labels are not required for the sensors described herein.

Solid Supports

In some examples one or more of the disclosed sensors are attached to a solid support. In some examples, suitable characteristics of the material that can be used to form the solid support surface include: being amenable to surface activation such that upon activation, the surface of the support is capable of covalently attaching a molecule (such as a nucleic acid molecule) that can bind to the target agent with high specificity; being chemically inert such that at the areas on the support not occupied by the molecule can bind to the target agent with high specificity are not amenable to non-specific binding, or when non-specific binding occurs, such materials can be readily removed from the surface without removing the molecule can bind to the target agent with high specificity.

In one example the solid support is a particle, such as a bead. Such particles can be composed of metal (e.g., gold, silver, platinum), metal compound particles (e.g., zinc oxide, zinc sulfide, copper sulfide, cadmium sulfide), non-metal compound (e.g., silica or a polymer), as well as magnetic particles (e.g., iron oxide, manganese oxide). The size of the bead is not critical; exemplary sizes include 5 nm to 5000 nm in diameter. In one example such particles are about 1 µm in diameter.

In another example, the solid support is a bulk material, such as a paper, membrane, porous material, water immiscible gel, water immiscible ionic liquid, water immiscible polymer (such as an organic polymer), and the like. For example, the solid support can comprises a membrane, such as a semi-porous membrane that allows some materials to pass while others are trapped. In one example the membrane comprises nitrocellulose.

In one example, the solid support is composed of an organic polymer. Suitable materials for the solid support include, but are not limited to: polypropylene, polyethylene, polybutylene, polyisobutylene, polybutadiene, polyisoprene, polyvinylpyrrolidine, polytetrafluoroethylene, polyvinylidene difluoroide, polyfluoroethylene-propylene, polyethylenevinyl alcohol, polymethylpentene, polycholorotrifluoroethylene, polysulformes, hydroxylated biaxially oriented polypropylene, aminated biaxially oriented polypropylene, thiolated biaxially oriented polypropylene, etyleneacrylic acid, thylene methacrylic acid, and blends of copolymers thereof).

In yet other examples, the solid support is a material containing, such as a coating containing, any one or more of or a mixture of the ingredients provided herein.

A wide variety of solid supports can be employed in accordance with the present disclosure. The solid support can be any format to which the molecule specific for the target agent can be affixed, such as microtiter plates, test tubes, inorganic sheets, dipsticks, and the like. One example includes a linear array of molecules specific for the target agent, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range.

In one example the format is a bead, such as a silica or glass bead. In another example the format is a nitrocellulose membrane. In another example the format is filter paper. In yet another example the format is a glass slide. In one example, the solid support is a polypropylene thread. One or more polypropylene threads can be affixed to a plastic dipstick-type device; polypropylene membranes can be affixed to glass slides.

In one example, one or more sensors disclosed herein can be part of a lateral flow device. A lateral flow device can be used to determine the presence and/or amount of one or more target agents in a fluid sample. A lateral flow device is an analytical device having a test strip, through which flows a test sample fluid that is suspected of (or known to) containing a target agent. Lateral flow devices are useful to simplify and automate user sample interface and processing. One example of a lateral flow device is a pregnancy strip. Based on the principles of a pregnancy strip, lateral flow devices that incorporate the disclosed sensors can be developed. In some examples, by using such as lateral flow devices, samples can be directly contacted with or applied to the lateral flow device, and no further liquid transfer or mixing is required. Such devices can be used to detect target agents, for example qualitatively or quantitatively.

Target Agents

The disclosed sensors can be designed to detect any target agent of interest. As described above, by selecting an appropriate molecule that permits detection of the target agent, allows one to develop a sensor that can be used to detect a particular target agent. Exemplary target agents are provided below; however one skilled in the art will appreciate that other target agents can be detected with the disclosed sensors using the disclosed methods.

Metals

In one example the target agent is a metal (e.g., elements, compounds, alloys that have high electrical conductivity or cations), such as a heavy metal. Metals occupy the bulk of the periodic table, while non-metallic elements can only be found on the right-hand-side of the Periodic Table of the Elements. A diagonal line drawn from boron (B) to polonium (Po) separates the metals from the nonmetals. Most elements on this line are metalloids, sometimes called semiconductors. Elements to the lower left of this division line are called metals, while elements to the upper right of the division line are called non-metals.

Heavy metals include any metallic chemical element that has a relatively high density. In one example, the metal is a cation that is toxic, highly toxic or poisonous at low concentrations. Examples of metals that can be detected with the disclosed sensors include mercury (Hg), cadmium (Cd), arsenic (As), chromium (Cr), thallium (Tl), and lead (Pb).

In one example the metal detected is uranium ($UO_2^{2+}$).

Pathogens/Microbes

Any pathogen or microbe can be detected using the sensors and methods provided herein. Exemplary pathogens include, but are not limited to, viruses, bacteria, fungi, nematodes, and protozoa. A non-limiting list of pathogens that can be detected using the sensors provided herein are provided below.

For example, viruses include positive-strand RNA viruses and negative-strand RNA viruses. Exemplary positive-strand RNA viruses include, but are not limited to: Picornaviruses (such as Aphthoviridae [for example foot-and-mouth-disease virus (FMDV)]), Cardioviridae; Enteroviridae (such as Coxsackie viruses, Echoviruses, Enteroviruses, and Polioviruses); Rhinoviridae (Rhinoviruses)); Hepatoviridae (Hepatitis A viruses); Togaviruses (examples of which include rubella; alphaviruses (such as Western equine encephalitis virus, Eastern equine encephalitis virus, and Venezuelan equine encephalitis virus)); Flaviviruses (examples of which include Dengue virus, West Nile virus, and Japanese encephalitis virus); Calciviridae (which includes Norovirus and Sapovirus); and Coronaviruses (examples of which include SARS coronaviruses, such as the Urbani strain).

Exemplary negative-strand RNA viruses include, but are not limited to: Orthomyxyoviruses (such as the influenza virus), Rhabdoviruses (such as Rabies virus), and Paramyxoviruses (examples of which include measles virus, respiratory syncytial virus, and parainfluenza viruses).

Viruses also include DNA viruses. DNA viruses include, but are not limited to: Herpesviruses (such as Varicella-zoster virus, for example the Oka strain; cytomegalovirus; and Herpes simplex virus (HSV) types 1 and 2), Adenoviruses (such as Adenovirus type 1 and Adenovirus type 41), Poxviruses (such as Vaccinia virus), and Parvoviruses (such as Parvovirus B19).

Another group of viruses includes Retroviruses. Examples of retroviruses include, but are not limited to: human immunodeficiency virus type 1 (HIV-1), such as subtype C; HIV-2; equine infectious anemia virus; feline immunodeficiency virus (FIV); feline leukemia viruses (FeLV); simian immunodeficiency virus (SIV); and avian sarcoma virus.

In one example, the sensor can distinguish between an infectious versus a non-infectious virus.

Pathogens also include bacteria. Bacteria can be classified as gram-negative or gram-positive. Exemplary gram-negative bacteria include, but are not limited to: *Escherichia coli* (e.g., K-12 and O157:H7), *Shigella dysenteriae*, and *Vibrio cholerae*. Exemplary gram-positive bacteria include, but are not limited to: *Bacillus anthracis, Staphylococcus aureus*, pneumococcus, gonococcus, and streptococcal meningitis.

Protozoa, nemotodes, and fungi are also types of pathogens. Exemplary protozoa include, but are not limited to, *Plasmodium, Leishmania, Acanthamoeba, Giardia, Entamoeba, Cryptosporidium, Isospora, Balantidium, Trichomonas, Trypanosoma, Naegleria*, and *Toxoplasma*. Exemplary fungi include, but are not limited to, *Coccidiodes immitis* and *Blastomyces dermatitidis*.

In one example, bacterial spores are detected. For example, the genus of *Bacillus* and *Clostridium* bacteria produce spores that can be detected. Thus, *C. botulinum, C. perfringens, B. cereus*, and *B. anthracis* spores can be detected (for example detecting anthrax spores). One will also recognize that spores from green plants can also be detected using the methods and sensors provided herein.

Proteins

The disclosed sensors also permit detection of a variety of proteins, such as cytokines, antibodies, hormones, as well as toxins.

In one example the protein is a cytokine. Cytokines are small proteins secreted by immune cells that have effects on other cells. Examples include interleukins (IL) and interferons (IFN), and chemokines, such as IL-1, IL-2, IL-4, IL-6, IL-8, IL-10, IFN-γ, IFN-β, transforming growth factor (TGF-β), and tumor necrosis factor (TNF)-α.

In one example the protein is a hormone. A hormone is a chemical messenger that transports a signal from one cell to another. Examples include plant and animal hormones, such as endocrine hormones or exocrine hormones. Particular examples include follicle stimulating hormone (FSH), human chorionic gonadotropin (hCG), thyroid stimulating hormone (TSH), growth hormone, progesterone, and the like.

In yet another example the protein is a toxin. Toxins are poisonous substances produced by cells or organisms, such as plants, animals, microorganisms (including, but not limited to, bacteria, viruses, fungi, rickettsiae or protozoa). Particular examples include botulinum toxin, ricin, diphtheria toxin, Shiga toxin, Cholera toxin, and anthrax toxin. In another example, the toxin is an environmental toxin.

Recreational and Other Drugs

The disclosed sensors also permit detection of a variety of drugs, such as pharmaceutical or recreational drugs. For example, the presence of caffeine, cocaine, opiates and opioids (such as oxycodone), cannabis (for example by detecting tetrahydrocannabinol (THC)), heroin, methamphetamines, crack, ethanol, or tobacco (for example by detecting nicotine), can be detected using the disclosed sensors.

Cells

The disclosed sensors also permit detection of a variety of cells, such as tumor or cancer cells, as well as other diseased cells. In on example, the sensor can distinguish between a tumor cell and a normal cell of the same cell type, such as a normal breast cell from a cancerous breast cell. Tumors are abnormal growths which can be either malignant or benign, solid or liquid (for example, hematogenous).

Examples of hematological tumors include, but are not limited to: leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin'lymphoma (including low-, intermediate-, and high-grade), multiple myeloma, Waldenstrom's macroglobulinemia, heavy chain disease, myelodysplastic syndrome, mantle cell lymphoma and myelodysplasia.

Examples of solid tumors, such as sarcomas and carcinomas, include, but are not limited to: fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Thus, in some examples the sensors provided herein permit detection of such tumor cells, such as a cancer cell.

Kits

The disclosure also provides kits that include one or more of the sensors disclosed herein. Such kits can include other components, such as a buffer, a chart for correlating detected fluorescence and amount of target agent present, a target agent, or combinations thereof. For example, the kit can include a vial containing one or more of the sensors disclosed herein and a separate vial containing the buffer.

In some examples the kit includes standard solutions in separate containers containing known amounts of target agents for calibration.

Methods of Detecting Target Agents

Methods of using the sensors disclosed herein to detect a target agent are provided herein. In one example, the method includes contacting one or more sensors with a sample under conditions sufficient to allow the target agent that may be present in the sample to bind to the sensor (which may be immobilized to a solid support) resulting in cleavage of the sensor or a conformational change of the sensor.

In some examples, binding of a target agent in the sample to the sensor results in cleavage of the sensor or a conformational change of the sensor, thereby resulting in an increase in fluorescence. The resulting fluorescence can be detected, wherein detection of fluorescence indicates the presence of the target agent in the sample, and an absence of detected fluorescence indicates the absence of the target agent in the sample. For example, a detection of an at least 10% (such as at least 20%, at least 50%, at least 75%, at least 80%, at least 90%, at least 100% or more) increase in fluorescence (for example relative to the absence of the target agent), indicates that the target agent is present in the sample. In contrast, detection of for example no more than a 1% (such as no more than 0.5% or 0.1%) increase in fluorescence (for example relative to the absence of the target agent), indicates that the target agent is not present in the sample.

The method can further include quantifying the target agent, wherein a level of fluorescence detected indicates an amount of target agent present.

In some embodiments, once a sample is analyzed, an indication of that analysis can be displayed and/or conveyed to a user. For example, the results of the test can be provided to a user (such as a clinician or other health care worker, laboratory personnel, or patient) in a perceivable output that provides information about the results of the test. In some embodiments, the output is a paper output (for example, a written or printed output), a display on a screen, a graphical output (for example, a graph, chart, voltammetric trace, or other diagram), or an audible output.

In other embodiments, the output is a diagnosis, such as whether the test sample analyzed contains the target agent tested for. In additional embodiments, the output is a graphical representation, for example, a graph that indicates the value (such as amount or relative amount) of the likelihood that the sample contains the target agent tested for. In some examples, the output is a number on a screen/digital display indicating the probability that the sample contains the target agent tested for. In some examples, the output is text, indicating the likelihood that the sample contains the target agent tested for along with the corresponding implications to the patient. Sensitivity, specificity, and confidence intervals may also be a part of the output. These outputs can be in the form of graphs or tabulated numbers. The output can be a color-coded image with different colors indicating different probabilities that the sample contains the target agent tested for. In some embodiments, the output is communicated to the user, for example by providing an output via physical, audible, or electronic means (for example by mail, telephone, facsimile transmission, email, or communication to an electronic medical record).

In some embodiments, the output is accompanied by guidelines for interpreting the data, for example, numerical or other limits that indicate whether the test sample contains the target agent tested for. The indicia in the output can, for example, include normal or abnormal ranges or a cutoff, which the recipient of the output may then use to interpret the results, for example, to arrive at a diagnosis, prognosis, or treatment plan. In other embodiments, the output can provide a recommended therapeutic regimen. In some embodiments, the test may include determination of other clinical information (such as determining the amount of one or more additional biomarkers in the biological sample).

Samples

Any biological or environmental specimen that may contain (or is known to contain or is suspected of containing) a target agent can be used. In some examples the method includes obtaining a sample, for example obtaining a patient, environmental, or food sample. Once a sample has been obtained, the sample can be used directly, concentrated (for example by centrifugation or filtration), diluted (for example in water, saline or other appropriate solution), purified, or combinations thereof. In some examples, proteins or nucleic acids or pathogens are purified from the sample, and the purified preparation analyzed using the methods provided herein.

Biological samples are usually obtained from a subject and can include genomic DNA, RNA (including mRNA), protein, or combinations thereof. Examples include a tissue or tumor biopsy, fine needle aspirate, bronchoalveolar lavage, pleural fluid, sputum, surgical specimen, lymph node, peripheral blood (such as serum or plasma), urine, buccal swab, and autopsy material. Techniques for acquisition of such samples are well known in the art (for example see Schluger et al. *J. Exp. Med.* 176:1327-33, 1992, for the collection of serum samples). Serum or other blood fractions can be prepared in the conventional manner.

Environmental samples include those obtained from an environmental media, such as water, air, soil, dust, wood, or food.

In one example the sample is a plant sample.

In some examples, a sample is obtained by swabbing a surface.

In other examples, a sample includes a control sample, such as a sample known to contain or not contain a particular amount of the target agent.

In one example the sample is a food sample, such as a meat, fruit, or vegetable sample. For example, using the methods provided herein, adulterants in food products can be detected, such as a pathogen or toxin or other harmful product.

EXAMPLE 1

Materials and Methods

This example provides the materials and methods used for the results described in Examples 3-6.

The fluorophore 2-amino-5,6,7-trimethyl-1,8-naphthyridine (ATMND; Ryan Scientific Inc., Mt. Pleasant, S.C.) was used as received. Metal ion salts, nucleotides, human serum, and other chemicals for buffers were purchased from Sigma-Aldrich Inc. (St. Louis, Mo.). The drinking water used is filtered tap water from the URIC campus.

The following oligonucleotides were purchased from Integrated DNA Technologies, Inc. (Coralville, Iowa):
$Pb^{2+}$-dependent DNAzyme and substrate (with a single RNA nucleotide linkage rA):

$17E_{va}$
(SEQ ID NO: 1)
5'-ACAGACATCTCTTCTCCGAGCCGGTCGAAATAGTG-3'

$17S_{va}$:
(SEQ ID NO: 2)
5'- GACGATGAAACATCGTCCCACTATrAGGAAGAGATGTCTGT-3'

$17S_{vaG}$:
(SEQ ID NO: 3)
5'-GGACGATGAAACATCGTCCCACTATrAGGAAGAGATGTCTGT-3'

$17E_{vaMut}$:
(SEQ ID NO: 4)
5'-ACAGACATCTCTTCCCCGAGCCGGTCGAAATAGTG-3'

Adenosine aptamer:

$AdAP_{va}$:
(SEQ ID NO: 5)
5'-GATCACAAAGTGATCCCACCTGGGGGAGTATTGCGGAGGAAGGT-3'

$AdAP_{vaM1}$
(SEQ ID NO: 6)
5'-GATCACAAAGTGATCCCACCTGGGGGTGTATTGCGGAGGAAGGT-3'

$AdAP_{vaM2}$
(SEQ ID NO: 7)
5'-GATCACAAAGTGATCCCACCTGGGGGAGTATTGCGGAGGTAGGT-3' ssDNAs for hybridization with adenosine aptamer:

AdL1$_{va}$     5'-CCAGGTG-3'     (SEQ ID NO: 8)

AdL2$_{va}$     5'-CCCAGGTG-3'    (SEQ ID NO: 9)

AdL3$_{va}$     5'-CCCCAGGTG-3'   (SEQ ID NO: 10)

AdL2$_G$        5'-CCCAGGTGG-3'   (SEQ ID NO: 11)

$UO_2^{2+}$-dependent DNAzyme and substrate (with a single RNA nucleotide linkage rA):

39E$_{va}$:
(SEQ ID NO: 12)
5'-CACGTCCATCTCTGCAGTCGGGTAGTTAAACCGACCTTCAGACATAGTG-3'

39S$_{va}$:
(SEQ ID NO: 13)
5'-GACGATGAAACATCGTCCCACTATrAGGAAGAGATGGACGTG-3'

$Hg^{2+}$ aptamer:

HgAP$_{va}$:
(SEQ ID NO: 14)
5'-GACGATGAAACATCGTCCCTGTTTGTTTGTTGGCCCCCCTTCTTTCTTAC-3' ssDNA for hybridization with $Hg^{2+}$ aptamer:

HgL$_{va}$: 5'-CAAACAG-3'    (SEQ ID NO: 15)

Fluorescence Experiments

For a typical $Pb^{2+}$ fluorescent sensing experiment, 480 μL buffer A (25 mM HEPES pH 7.0 and 100 mM NaCl), 5 μL ATMND stock solution (75 μM), 5 μL substrate 17S$_{va}$ (100 μM), and 10 μL DNAzyme 17E$_{va}$ (100 μM) were added sequentially into a 1.5 mL microcentrifuge tube. Upon vortexing, the tube was allowed to stand at room temperature for 2 min. The solution was then transferred to a cuvette and kept under a constant temperature control at 5° C. After 6 min to allow the temperature to reach equilibrium, 5 μL of $Pb^{2+}$ stock solution (0~200 μM) in 1 mM HNO$_3$ was added to the cuvette, which was then vortexed. A time-dependent fluorescent measurement at ex/em=358/405 nm was immediately started.

The procedure for the $UO_2^{2+}$ fluorescent sensing experiment is the same as that of the $Pb^{2+}$ fluorescent sensing experiment, except that the following reagents were used: 470 μL buffer B (50 mM MES pH 5.5 and 300 mM NaCl), 5 μL ATMND stock solution (100 μM), 10 μL substrate 39S$_{va}$ (100 μM), and 15 μL DNAzyme 39E$_{va}$ (100 μM).

In the kinetic study of the above DNAzyme-based sensors, a fluorescence decrease was observed in the first 2 min, especially at low $Pb^{2+}$ or $UO_2^{2+}$ concentrations (FIGS. 1*b* and 3). This decrease is due to the temperature effect of adding $Pb^{2+}$ or $UO_2^{2+}$ stock solution at room temperature to the sensor solution equilibrated at 5° C. As a result, a brief temperature increase occurred at the beginning. Since the fluorescence of the ATMND-DNA complex tends to decrease with increasing temperature (Yoshimoto et al., *J. Am. Chem. Soc.* 2003, 125, 8982-8983), the fluorescence decrease was then observed in the initial 2 min before the temperature equilibrated. Because of this issue, the data between 6~8 min were acquired for quantification to avoid the disturbance from the temperature change. For samples with high concentrations of $Pb^{2+}$ and $UO_2^{2+}$ (more than 250 nM), this temperature effect is negligible because the fluorescence signal increase is much faster. In this case, the initial rate for the first 30 s of fluorescence change was recorded to avoid the effect of substrate DNA depletion on the signal changes.

In a typical adenosine sensing experiment, 480 μL buffer C (10 mM HEPES pH 7.0, 100 mM NaCl and 1 mM EDTA), 5 μL aptamer AdAP$_{va}$ (100 μM), 10 μL ssDNA AdL1$_{va}$~AdL3$_{va}$ (100 μM), and 5 μL ATMND stock solution (50 μM) were added sequentially into a 1.5 mL microcentrifuge tube. After vortexing, the tube was allowed to stand at room temperature for 1 min. A 5 μL of adenosine stock solution (0~1 mM) in buffer C was added to the above mixture, the solution was vortexed, and then it was allowed to stand at room temperature for 1 min. The solution was then transferred to a cuvette and kept under a constant temperature control at 5° C. After 10 min, the fluorescence intensity at ex/em=358/405 nm was recorded. The sample showed a stable intensity signal from 8~30 min.

The procedure for $Hg^{2+}$ fluorescent sensing experiment is the same as that of the adenosine sensing experiment, except that the following reagents were used: 480 μL buffer D (10 mM MOPS pH 7.2, 100 mM NaNO$_3$), 5 μL aptamer HgAP$_{va}$ (30 μM), 5 μL ssDNA HgL$_{va}$ (35 μM), and 5 μL ATMND stock solution (10 μM).

$Pb^{2+}$ Detection in Drinking Water

Concentrated stock solutions of HEPES (500 mM) and NaCl (2 M) was added to drinking water containing different amounts of $Pb^{2+}$ to achieve final concentration of HEPES and NaCl as 25 mM and 75 mM, respectively. Then, 480 μL of the sample, 5 μL ATMND stock solution (75 μM), 5 μL substrate 17S$_{va}$ (100 μM), and 10 μL DNAzyme 17E$_{va}$ (100 μM) were added sequentially into a 1.5 mL microcentrifuge tube. Upon vortexing, the tube was allowed to stand at room temperature for 2 min and then transferred to a cuvette and kept at 5° C. After 25 min, the fluorescence intensity at ex/em=358/405 nm was recorded.

Adenosine Detection in Human Serum

Human serum was diluted five-fold by buffer C to produce a 20% serum sample. The detection of adenosine in this diluted serum sample is the same as that in buffer C as shown above. The concentration of adenosine detected in the diluted serum can be converted to the concentration in the original serum by multiplying the results by five.

EXAMPLE 2

General Design of Vacant Site-Containing Dnazymes and Aptamers

It was hypothesized that a vacant site (Li et al., *Anal. Chim. Acta* 2007, 597, 97-102) could serve as the binding site for a fluorophore in functional DNA sensors (FIG. 1). This site's affinity for fluorophores such as ATMND could be enhanced via hydrogen bonds, π-π stacking, and electrostatic interactions by positioning a cytosine opposite to the vacant site and two flanking guanines in DNA duplex. In the absence of targets, the functional DNA sensors could be designed to stabilize the vacant site to bind ATMND strongly, allowing the duplex DNA to quench the fluorescence of ATMND.

A titration experiment carried out by adding different amounts of DNA-duplex containing a vacant site to ATMND indicated that they bound with high affinity ($K_a > 10^6 M^{-1}$) and the resulting complex was stable in solution for at least one week (FIG. 1E). The presence of a target, on the other hand, can cause either the catalytic cleavage of substrate by a DNAzyme or the structure-switching of an aptamer, resulting in perturbation of the vacant site, which lowers its affinity for ATMND. When ATMND is released, its fluorescence intensity increases. By monitoring this fluorescence change, the concentrations of target analytes can be measured.

To demonstrate the generality of this vacant-site approach to functional DNA sensors, a $Pb^{2+}$-dependent DNAzyme, a $UO_2^{2+}$-dependent DNAzyme, adenosine aptamer, and $Hg^{2+}$-binding DNA with T-T mismatches (which may be considered to be an aptamer for $Hg^{2+}$) were developed as models.

EXAMPLE 3

Performance of the Label-Free Functional DNA Sensors with Unmodified DNA (1) $Pb^{2+}$ sensor based on 8-17 DNAzyme. The design of label-free fluorescent sensor based on $Pb^{2+}$-dependent 8-17 DNAzyme (Li and Lu, *J. Am. Chem. Soc.* 2000, 122, 10466-10467) is shown in FIG. 1A. A loop was added to the 5'-end of the substrate strand (named $17S_{va}$; SEQ ID NO: 2) of the DNAzyme (named $17E_{va}$; SEQ ID NO: 1) to form a vacant site in the $17S_{va}/17E_{va}$ duplex.

Figure 2B:
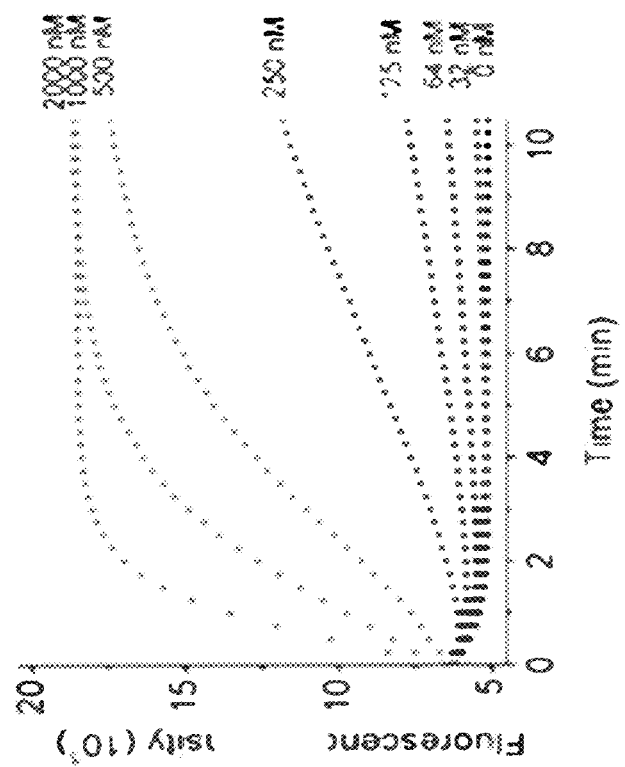
FIGS. 2A and B are graphs showing (a) fluorescence spectra of (1) ATMND, (2) ATMND/$17S_{va}$/$17E_{va}$, (3) ATMND/$17S_{va}$/$17E_{va}$/$Pb^{2+}$, (4) ATMND/$17S_{va}$/$17E_{va}$/$Pb^{2+}$/EDTA and (b) kinetics of fluorescence enhancement of ATMND/$17S_{va}$/$17E_{va}$ in the presence of different amounts of $Pb^{2+}$. Condition: 25 mM HEPES pH 7.0 and 100 mM NaCl at 5° C. $\lambda_{ex}/\lambda_{em}$=358/405 nm.
Figure 2A:
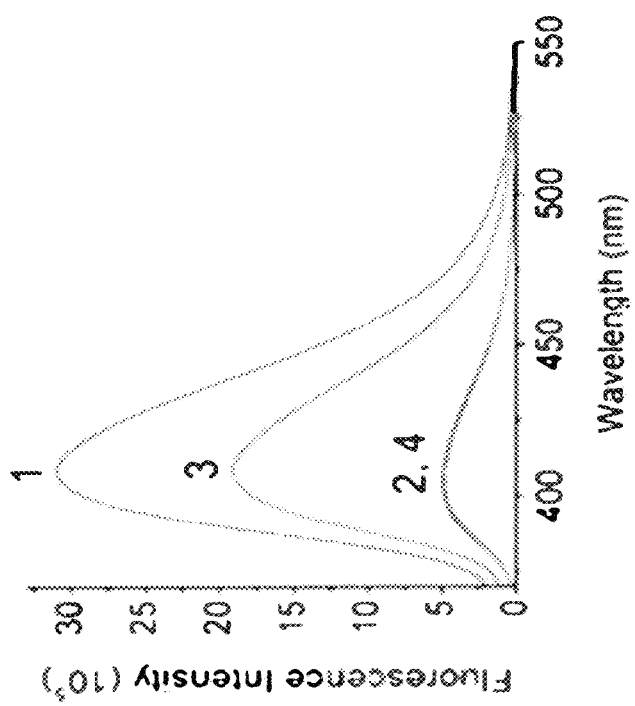

As illustrated in FIG. 2A, the addition of 0.75 μM of ATMND into 1 μM $17S_{va}$ and 2 μM $17E_{va}$ resulted in ~85% quenching of fluorescence signal of ATMND at 405 nm (compare Curves 1 and 2). This result suggested the strong binding of the ATMND to the vacant site as designed. Interestingly, the addition of 1 μM $Pb^{2+}$ to the above system produced 275% increase of fluorescent signal within 6 min, (Curve 3), probably due to the $Pb^{2+}$-induced cleavage of $17S_{va}$ and the release of ATMND from DNA duplex. To confirm the role of $Pb^{2+}$ in the catalytic reaction, the above experiment was repeated in the presence of 1 mM EDTA, a metal ion chelator, and no fluorescent enhancement was observed (Curve 4).

Figure 3A:
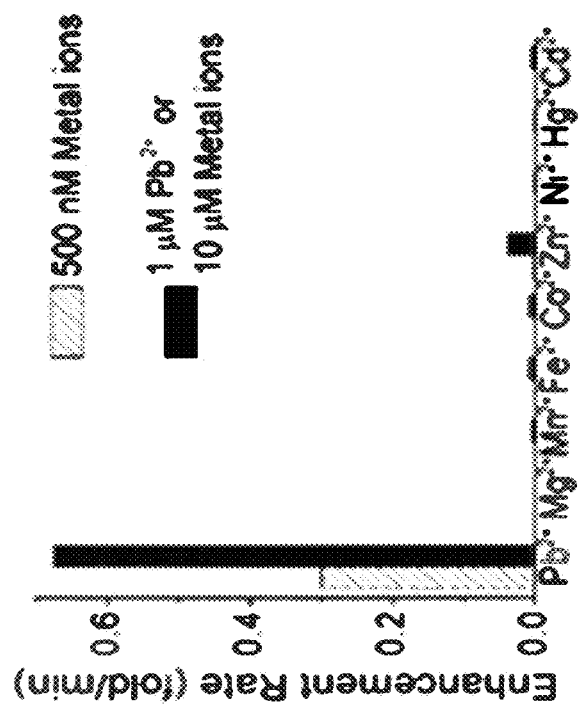
FIGS. 3A and B are graphs showing (a) fluorescence enhancement rate as a function of $Pb^{2+}$ concentration (0~100 nM) for ATMND/$17S_{va}$/$17E_{va}$. Inset: 0~2 µM $Pb^{2+}$ range and (b) selectivity of ATMND/$17S_{va}$/$17E_{va}$ toward $Pb^{2+}$ over other divalent metal ions. Condition: 25 mM HEPES pH 7.0 and 100 mM NaCl at 5° C. $\lambda_{ex}/\lambda_{em}$=358/405 nm
Figure 3B:
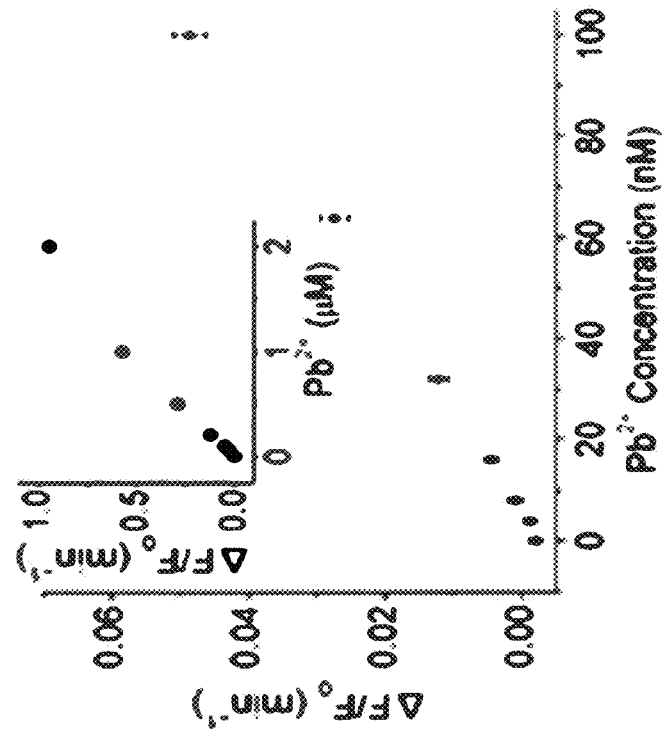

The kinetics of fluorescence enhancement were dependent on the concentration of $Pb^{2+}$ (FIG. 2B), displaying an increasing rate in the presence of higher concentrations of $Pb^{2+}$. Instead of fluorescent intensity, the ratio of fluorescence enhancement rate over the fluorescence of a blank ($\Delta F/F_0$) was recorded, because the ratio is independent of fluorescence intensity and thus much less vulnerable to fluctuations in the background fluorescence. The blank fluorescence ($F_0$) was that of ATMND/$17S_{va}$/$17E_{va}$ free of $Pb^{2+}$. The $\Delta F/F_0$ exhibited an approximately linear relationship with the concentration of $Pb^{2+}$ between 0~2 μM, and a calibration equation of $\Delta F/F_0$ (min$^{-1}$)=$0.494 \times C_{Pb}^{2+}$ (μM)−3.05 was derived from 7 data points within 0~100 nM $Pb^{2+}$ (FIG. 3A). A detection limit of 8 nM was obtained based on $3\sigma_b$/slope ($\sigma_b$, standard deviation of the blank samples) under the optimized condition. This detection limit is well below the maximum contamination level in drinking water (72 nM) defined by the US Environmental Protection Agency (EPA), and is comparable or better than $Pb^{2+}$ sensors reported previously (Li and Lu, *J. Am. Chem. Soc.* 2000, 122, 10466-10467; Liu and Lu, *Methods Mol. Biol.* 2006, 335, 275-288). (Liu et al., *J. Am. Chem. Soc.* 2002, 124, 15208-15216; Brown et al., *Biochemistry* 2003, 42, 7152-7161; Kim et al., *Nat. Chem. Biol.* 2007, 3, 763-768). This detection limit is very similar to those of fluorophore-labeled and dSpacer label-free methods using a $Pb^{2+}$-dependent DNAzyme (Liu and Lu, *Methods Mol. Biol.* 2006, 335, 275-288; Liu and Lu, *Methods Mol. Biol.* 2006, 335, 275-288; Xiang et al., *J. Am. Chem. Soc.* 2009, 131, 15352-15357), indicating that the detection limit is dependent on the functional DNA used and is not affected by the vacant sites incorporated into the DNA. Besides the high sensitivity, this vacant site approach did not sacrifice selectivity, as the selectivity toward $Pb^{2+}$ over other divalent metal ions is similar to that reported before (FIG. 3B).

(2) $UO_2^{2+}$ sensor based on 39E DNAzyme. After demonstrating the label-free $Pb^{2+}$ sensor using 8-17 DNAzyme via the vacant site approach, the ability of this approach to be generally applied to other DNAzyme sensors, such as the $UO_2^{2+}$-dependent 39E DNAzyme (Liu et al., *Proc. Nat. Acad. Sci. U.S.A.* 2007, 104, 2056-2061; Brown et al., *ChemBioChem* 2009, 10, 486-492) was demonstrated. The sensor was designed so that the 5'-end of the substrate (named $39S_{va}$; SEQ ID NO: 13) was extended to form a vacant site in the DNA duplex between the DNAzyme (named $39E_{va}$; SEQ ID NO: 12) and $39S_{va}$ (FIG. 1B).

Figure 4:
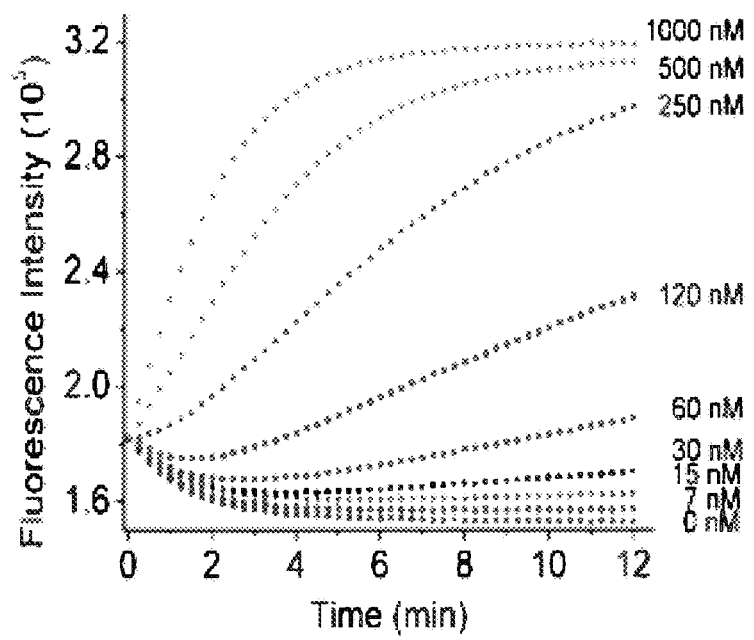
FIG. 4 is a graph showing the kinetics of fluorescence enhancement of ATMND/$39S_{va}$/$39E_{va}$ in the presence of different amounts of $UO_2^{2+}$. Condition: 50 mM MES pH 5.5 and 300 mM NaCl at 5° C. $\lambda_{ex}/\lambda_{em}$=358/405 nm.

Similar to the $Pb^{2+}$ sensor, a $UO_2^{2+}$-dependent fluorescence enhancement (FIG. 4) was observed when different amounts of $UO_2^{2+}$ were added to the solution containing 1 μM ATMND, 2 μM $39S_{va}$ and 3 μM $39E_{va}$. The rate of enhancement over blank increased with the concentration of $UO_2^{2+}$. The increase of fluorescence is attributable to the $UO_2^{2+}$-dependent cleavage of substrate $39S_{va}$ by enzyme $39E_{va}$ that released ATMND from the vacant site and recovered the quenched fluorescence of ATMND.

Figure 5A:
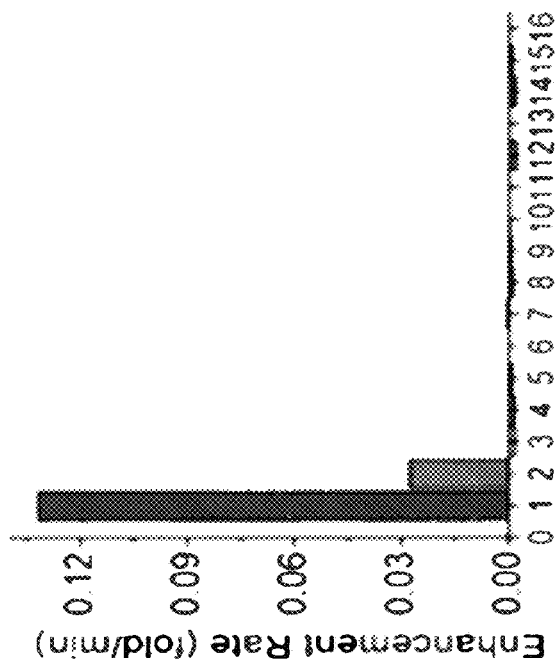
FIGS. 5A and B are graphs showing (a) fluorescence enhancement rate as a function of $UO_2^{2+}$ concentration (0~60 nM) for ATMND/$39S_{va}$/$39E_{va}$. Inset: 0~1 µM $UO_2^{2+}$ range, and (b) selectivity of ATMND/$39S_{va}$/$39E_{va}$ toward $UO_2^{2+}$ over other metal ions. 1~16: 500 nM $UO_2^{2+}$, 125 nM $UO_2^{2+}$, 2 µM $Mg^{2+}$/$Ca^{2+}$/$Sr^{2+}$/$Ba^{2+}$, $Mn^{2+}$, $Fe^{2+}$, $VO^{2+}$, $Th^{4+}$, $Tb^{3+}$, $Eu^{3+}$, $Co^{2+}$, $Ni^{2+}$, $Cu^{2+}$, $Zn^{2+}$, $Pb^{2+}$, $Cd^{2+}$, $Hg^{2+}$. Condition: 50 mM MES pH 5.5 and 300 mM NaCl at 5° C. $\lambda_{ex}/\lambda_{em}$=358/405 nm.
Figure 5B:
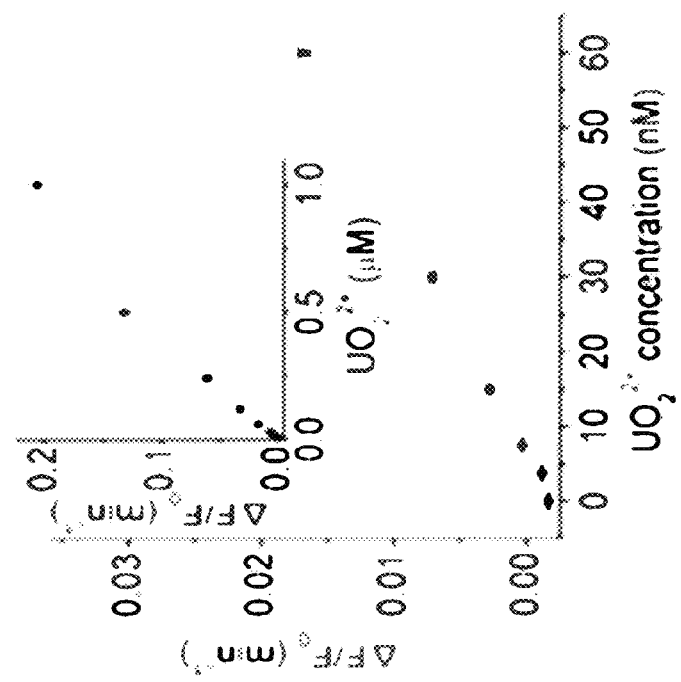

A detection limit (defined as $3\sigma_b$/slope, $\sigma_b$, standard deviation of the blank samples) of 3 nM and an approximately linear range at least within 0~1 μM $UO_2^{2+}$ as $\Delta F/F_0$ (min$^{-1}$)= $0.302 \times C_{UO2}^{2+}$ (μM)−1.9 (calibrated from the data within 0~60 nM range) were obtained under the optimal condition (FIG. 5A). Although this detection limit of 3 nM is higher than the 45 μM detection limit of the original fluorophore-labeled design (Liu et al., *Proc. Nat. Acad. Sci. U.S.A.* 2007, 104, 2056-2061), because of the higher concentration of DNA used to stabilize the vacant-site to enable efficient label-free fluorophore binding, the sensitivity is high enough to monitor uranium in real-world samples such as drinking water, as the detection limit is still above the US Environmental Protection Agency (EPA) maximum contamination level of 126 nM in drinking water). Similar to the original labeled design (Liu et al., *Proc. Nat. Acad. Sci. U.S.A.* 2007, 104: 2056-2061; Brown et al., *ChemBioChem* 2009, 10:486-492), the label-free sensor described herein maintained the excellent selectivity toward $UO_2^{2+}$ over other metal ions (FIG. 5B).

(3) Adenosine sensor based on adenosine aptamer. In addition to the DNAzymes, this vacant site approach to the design of aptamer sensors was demonstrated. The 5'-end sequence of the adenosine aptamer (Liu and Lu, *Angew. Chem., Int. Ed.* 2006, 45, 90-94; Nutiu, R.; Li, Y. *J. Am. Chem. Soc.* 2003, 125, 4771-4778; Liu, J.; Lu, Y. *Advanced Materials* 2006, 18, 1667-1671; Liu, J.; Lee, J. H.; Lu, Y. *Anal. Chem.* 2007, 79, 4120-4125) was extended to form a loop. In doing so, a vacant site could also be formed in the DNA duplex between the adenosine aptamer (named $AdAP_{va}$; SEQ ID NO: 5) and its partially complementary single strand DNA (named $AdL2_{va}$; SEQ ID NO: 9) (FIG. 1C).

Figure 6B:
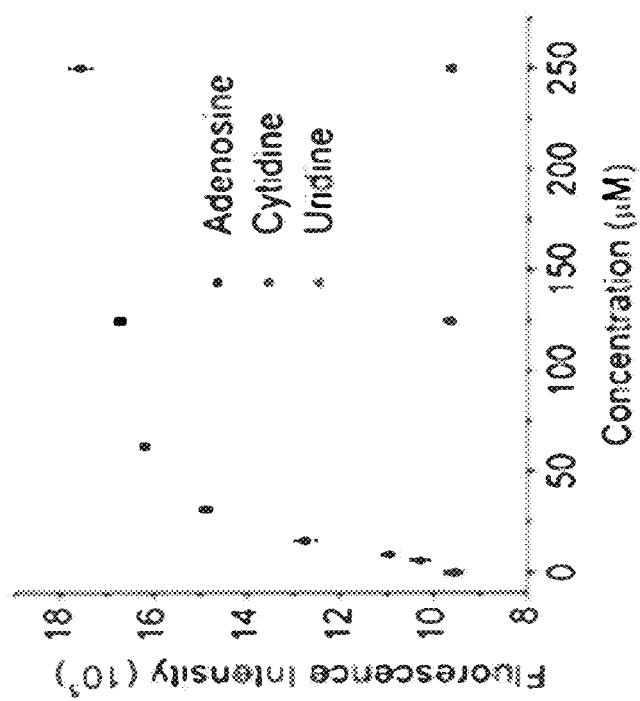
FIGS. 6A and B are graphs showing the (a) fluorescence spectra of (1) ATMND, (2) ATMND/$AdAP_{va}$/$AdL2_{va}$, (3) ATMND/$AdAP_{va}$/$AdL2_{va}$/adenosoine, (4) ATMND/$AdAP_{va}$/$AdL2_{va}$/cytidine and (b) adenosine-dependent fluorescence enhancement of ATMND/$AdAP_{va}$/$AdL1_{va}$. Condition: 10 mM HEPES pH 7.0, 100 mM NaCl and 1 mM EDTA at 5° C. $\lambda_{ex}/\lambda_{em}$=358/405 nm.
Figure 6A:
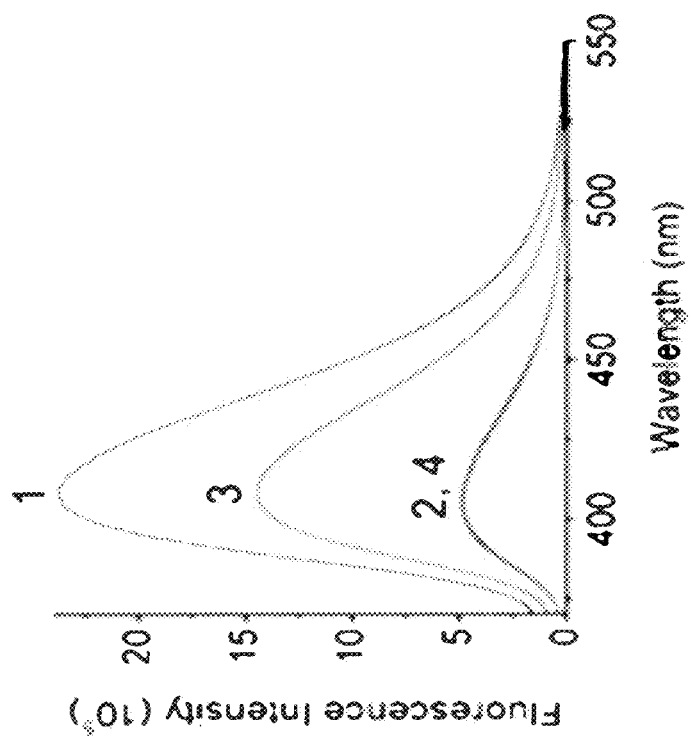

Similar to what was observed in the DNAzyme sensors described above, the addition of 0.5 µM ATMND to a solution containing 1 µM AdAP$_{va}$ (SEQ ID NO: 5) and 2 µM of AdL2$_{va}$ (SEQ ID NO: 9) resulted in ~80% quenching of the ATMND fluorescence (FIG. 6A, Curves 1 and 2). Upon the addition of 200 µM adenosine to the above solution, the fluorescence was increased by 200% (Curve 3), suggesting that the structure-switching (Nutiu, R.; Li, Y. *Chem. Eur. J.* 2004, 10, 1868-1876; Nutiu, R.; Li, Y. *J. Am. Chem. Soc.* 2003, 125, 4771-4778; Nutiu, R.; Li, Y. *Angew. Chem., Int. Ed.* 2005, 44, 1061-1065) of the aptamer caused the release of both AdL2$_{va}$ and ATMND and recovered the fluorescence of ATMND. In contrast, cytidine could not recover any of the fluorescence (Curve 4), indicating the essential role of adenosine as a specific target to the aptamer AdAP$_{va}$.

The fluorescence enhancement of ATMND was indeed dependent on the concentration of adenosine in the solution containing ATMND/AdAP$_{va}$/AdL1$_{va}$ (FIG. 6b). A 100% increase of fluorescence intensity was observed when the first 60 µM adenosine was added, while the fluorescence approached its maximum upon subsequent addition of adenosine up to 250 µM.

A detection limit of 6 µM was obtained by the definition of $3\sigma_b$/slope ($\sigma_b$, standard deviation of the blank samples) when using ATMND/AdAP$_{va}$/AdL1$_{va}$ for adenosine quantification under the optimized condition. This detection limit is similar to that of the original labeled aptamer sensor (Nutiu, R.; Li, Y. *J. Am. Chem. Soc.* 2003, 125, 4771-4778), indicating that the activity of the aptamer was not affected by the incorporation of a vacant site. The selectivity of the aptamer to adenosine over cytidine and uridine was also well preserved in this vacant-site-based sensor, because only adenosine could produce a fluorescence enhancement response among the three nucleotides in FIG. 6B (guanosine was not tested due to a solubility issue that hindered the preparation of a stock solution). More interestingly, by using ssDNAs (AdL1$_{va}$~AdL3$_{va}$; SEQ ID NOS: 8-10) that were complementary to AdAP$_{va}$ with different number of base pairs, the dynamic range of the sensor system could be tuned to 6~60 µM, 12~200 µM, or 32~1000 µM, respectively (FIGS. 7A-B) (Liu and Lu, *J. Am. Chem. Soc.* 2003, 125, 6642-6643; Wang et al., *Adv. Mater.* 2008, 20, 3263-3267; Xiang et al., *J. Am. Chem. Soc.* 2009, 131, 15352-15357; Vallee-Belisle et al., *Proc. Nat. Acad. Sci. U.S.A.* 2009, 106, 13802-13807). This tunable dynamic range makes it possible to apply this sensor system to samples containing different levels of analyte with a sensitive response.

(4) Hg$^{2+}$ sensor based on T-T mismatch. Since the vacant site approach can be applied to both DNAzyme and aptamer sensor design, the approach was expanded to Hg$^{2+}$ sensing based on T-T mismatch. T-T mismatches have been reported to be a very efficient binding site for Hg$^{2+}$ in aqueous solution (Ono et al., *Angew. Chem., Int. Ed.* 2004, 43, 4300-4302; Miyake et al., *J. Am. Chem. Soc.* 2006, 128, 2172-2173; Tanaka et al., *J. Am. Chem. Soc.* 2007, 129, 244-245; Okamoto et al., *Angew. Chem., Int. Ed.* 2009, 48, 1648-1651). It has been the basis of several Hg$^{2+}$ sensors (Ono et al., *Angew. Chem., Int. Ed.* 2004, 43, 4300-4302; Miyake et al., *J. Am. Chem. Soc.* 2006, 128, 2172-2173; Tanaka et al., *J. Am. Chem. Soc.* 2007, 129, 244-245; Wang et al., *Chem. Commun.* 2008, 6005-6007; Okamoto et al., *Angew. Chem., Int. Ed.* 2009, 48, 1648-1651). Here, a loop was linked to the 5'-end of the DNA containing T-T mismatches (named HgAP$_{va}$; SEQ ID NO: 14) to build a vacant site with the single strand DNA (HgL$_{va}$) that was partially complementary to HgAP$_{va}$ (SEQ ID NO: 15) (FIG. 1D).

Figure 8B:
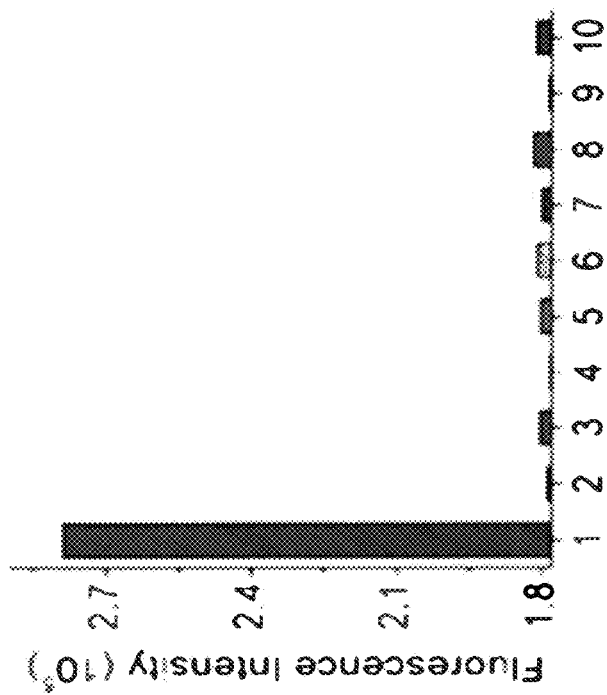
FIGS. 8A and B are graphs showing the (a) $Hg^{2+}$-dependent fluorescence enhancement of ATMND/$HgAP_{va}$/$HgL_{va}$. (b) Selectivity of ATMND/$HgAP_{va}$/$HgL_{va}$ toward $Hg^{2+}$ over other divalent metal ions. 1~10: 1 µM $Hg^{2+}$, 2 µM $Mg^{2+}$, $Ca^{2+}$, $Cu^{2+}$, $Zn^{2+}$, $Mn^{2+}$, $Co^{2+}$, $Cd^{2+}$, $Ni^{2+}$, $Pb^{2+}$. Condition: 10 mM MOPS buffer pH 7.2 and 100 mM $NaNO_3$ at 5° C. $\lambda_{ex}/\lambda_{em}$=358/405 nm.
FIG. 8C are graphs showing the effect of salt concentration on the performance of DNAzyme (left) and aptamer (right) based sensors in this work. Left: red dots, ATMND/$17S_{va}$/$17E_{va}$ in the presence of 200 nM $Pb^{2+}$; blue dots, ATMND/$17S_{va}$/$17E_{va}$ in the absence of $Pb^{2+}$; pink squares: ATMND/$39S_{va}$/$39E_{va}$ in the presence of 100 nM $UO_2^{2+}$; black squares: ATMND/$39S_{va}$/$39E_{va}$ in the absence of $UO_2^{2+}$. Right: black squares, ATMND/$AdAP_{va}$/$AdL1_{va}$ in the presence of 125 µM adenosine; red dots, ATMND/$HgAP_{va}$/$HgL_{va}$ in the presence of 500 nM $Hg^{2+}$. The salt for $Hg^{2+}$ sensor was $NaNO_3$, while others were NaCl. The pH was fixed at the values of buffer A~D, respectively.
FIG. 8D are graphs showing the effect of pH on the performance of DNAzyme (left) and aptamer (right) based sensors in this work. Left: red dots, ATMND/$17S_{va}$/$17E_{va}$ in the presence of 200 nM $Pb^{2+}$; blue dots, ATMND/$17S_{va}$/$17E_{va}$ in the absence of $Pb^{2+}$; pink squares: ATMND/$39S_{va}$/$39E_{va}$ in the presence of 100 nM $UO_2^{2+}$; black squares: ATMND/$39S_{va}$/$39E_{va}$ in the absence of $UO_2^{2+}$. Right: black squares, ATMND/$AdAP_{va}$/$AdL1_{va}$ in the presence of 125 µM adenosine; red dots, ATMND/$HgAP_{va}$/$HgL_{va}$ in the presence of 500 nM $Hg^{2+}$. The pH of 4.75 and 5.5 were adjusted by MES while 7.0 and 7.75 were by HEPES. The pH of 6.25 was checked using both MES and HEPES and the results were similar. Salt concentration was fixed at 100 mM.
FIGS. 8 E and F are graphs showing the effect of vacant site on the response of (e) ATMND/17S$_{va}$(17S$_{vaG}$)/17E$_{va}$ to Pb$^{2+}$, and (f) ATMND/AdAP$_{va}$/AdL2$_{va}$(AdL2$_{vaG}$) to adenosine. (−) and (+): in the absence and presence of (e) 1 μM Pb$^{2+}$ or (r) 200 μM adenosine, respectively.
FIGS. 8G and H are graphs showing (g) response of 17E$_{va}$ and its inactive mutant 17E$_{vaMut}$ to Pb$^{2+}$ in the presence of 17S$_{va}$ and ATMND and. (h) response of AdAP$_{va}$ and its inactive mutants AdAP$_{vaM1}$ and AdAP$_{vaM2}$ to adenosine in the presence of AdL1$_{va}$ and ATMND.
FIG. 8I is a series of bar graphs comparing the sensor responses in buffer and mixture to evaluate the selectivity and immunity to matrix effect. For the four sensors, 1 μM Cd$^{2+}$, Fe$^{2+}$, Ni$^{2+}$, Co$^{2+}$, Ca$^{2+}$ and Mg$^{2+}$ were added to the buffer as mixture. In addition, 500 nM UO$_2$$^{2+}$ and Hg$^{2+}$ were added to the mixture for Pb$^{2+}$ sensor; 500 nM Pb$^{2+}$ and Hg$^{2+}$ were added to the mixture for UO$_2$$^{2+}$ sensor; 500 nM Pb2+ and UO$_2$$^{2+}$; 500 nM Pb$^{2+}$, UO$_2$$^{2+}$, Hg$^{2+}$ and 500 μM cytidine, uridine were added to the mixture for adenosine sensor.
FIG. 8J is a series of calibration curves for quantification of Pb$^{2+}$ (left) and adenosine (right, light blue) in drinking water and human serum, respectively.
Figure 8A:
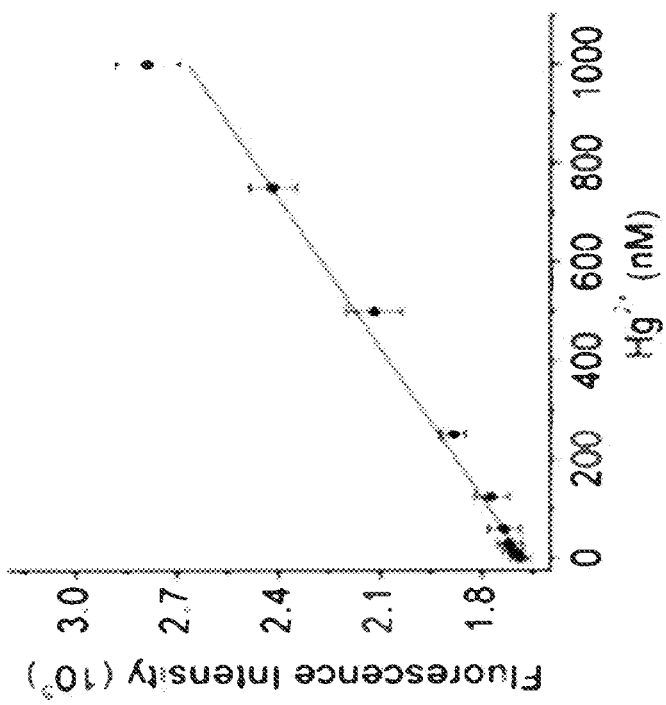

Similar to the DNAzyme and aptamer systems, the fluorescence of 0.1 µM ATMND was quenched upon binding to 0.3 µM HgAP$_{va}$ and 0.35 µM HgL$_{va}$. The subsequent addition of Hg$^{2+}$ caused the fluorescence enhancement of ATMND, probably by releasing HgL$_{va}$ and ATMND from the DNA duplex via the Hg$^{2+}$-induced structure-switching (Wang et al., *Chem. Commun.* 2008, 6005-6007; Nutiu and Li, *Angew. Chem., Int. Ed.* 2005, 44, 1061-1065; Nutiu and Li, *Chem. Eur. J.* 2004, 10, 1868-1876; Nutiu and Li, *J. Am. Chem. Soc.* 2003, 125, 4771-4778). The fluorescence intensity of the solution was found to be proportional to the concentration of Hg$^{2+}$ (FIG. 8A), with a detection limit of about 30 nM (defined as $3\sigma_b$/slope, $\sigma_b$, standard deviation of the blank samples) and a linear range at least within 0~1000 nM Hg$^{2+}$. The moderate sensitivity of this sensor compared to labeled sensors (Wang et al., *Chem. Commun.* 2008, 6005-6007) was possibly due to the fact that the vacant site approach requires a larger amount of HgAP$_{va}$ loading (300 nM) to stabilize the vacant site and that each DNA strand might need several Hg$^{2+}$ ions to induce structure-switching. Nevertheless, the selectivity of the sensor here toward Hg$^{2+}$ over other divalent metal ions was as good as the reported Hg$^{2+}$ sensors (Ono, A.; Togashi, H. *Angew. Chem., Int. Ed.* 2004, 43, 4300-4302; Wang et al., *Chem. Commun.* 2008, 6005-6007) using the T-T mismatch design (FIG. 8B).

EXAMPLE 4

Effects of pH and Salt Concentration

The pH and salt concentration affect the performance of the functional DNA sensors described herein, because both the hybridization of DNA and the activity of the functional DNAs may be affected by the conditions.

Figure 8D:
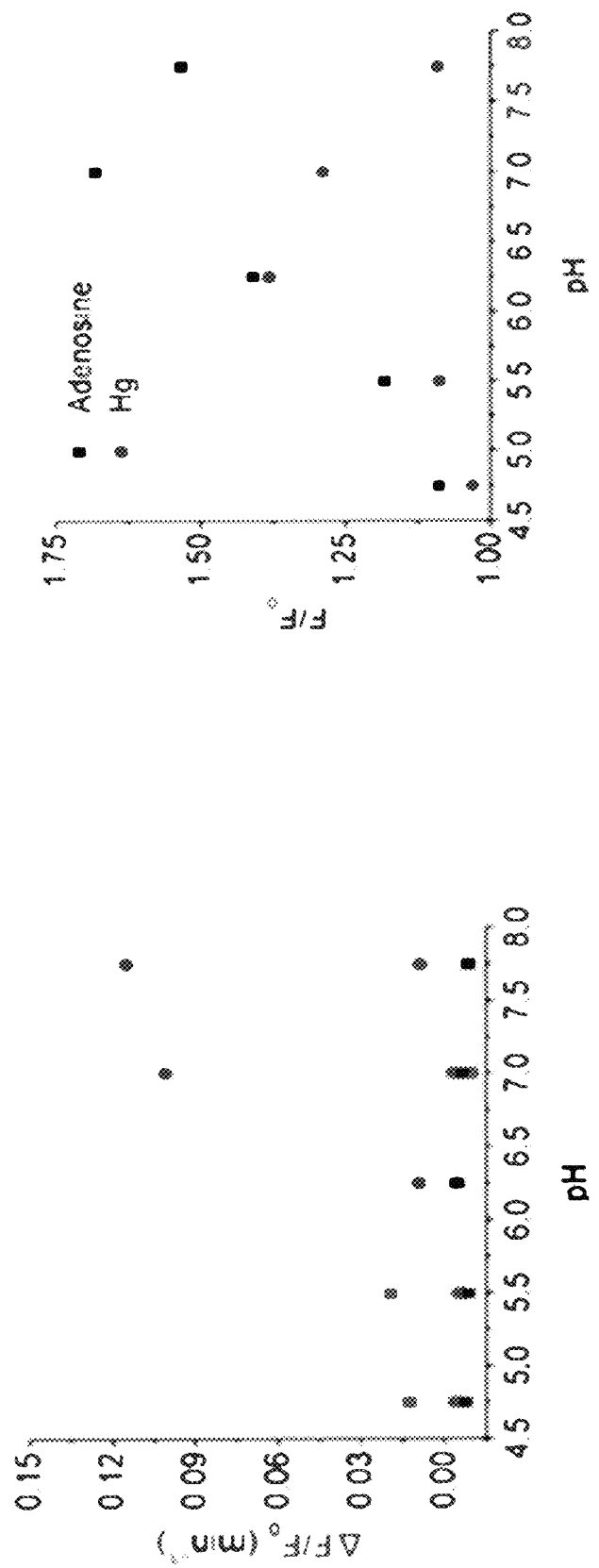

As shown in FIG. 8C, when the pH was maintained at 7.0, 5.5, 7.0 and 7.2 for Pb$^{2+}$, UO$_2^{2+}$, adenosine, and Hg$^{2+}$ sensors shown in FIGS. 1A-D, respectively, as those conditions used in the published reports, 100 mM sodium salt was found to be the optimal salt concentration to yield the highest signal response. The performance of the UO$_2^{2+}$ sensor is similar in the presence of either 100 or 300 mM NaCl. By fixing the salt concentration at 100 mM for the Pb$^{2+}$, adenosine, and Hg$^{2+}$ sensors, and at 300 mM for the UO$_2^{2+}$ sensor, the effect of pH was investigated (FIG. 8D).

For the Pb$^{2+}$ and UO$_2^{2+}$ sensors, the optimal pHs of 7.0 and 5.5, respectively, were found to be similar to the optimal pHs reported previously (Li and Lu, *J. Am. Chem. Soc.* 2000, 122, 10466-10467; Liu et al., *Proc. Nat. Acad. Sci. U.S.A.* 2007, 104, 2056-2061.; Brown et al., *ChemBioChem* 2009, 10, 486-492). Even though the Pb$^{2+}$ sensor exhibited a faster rate of fluorescence enhancement at pH 7.75 than at pH 7.0, a higher background fluorescence increase was also observed (FIG. 8D). For the adenosine and Hg$^{2+}$ sensors, a neutral pH was found to be optimal (FIG. 8D).

EXAMPLE 5

Effects of Vacant Site and DNA Sequences

To further confirm that the observed fluorescence enhancement of ATMND was induced by the weakened binding of the vacant site to ATMND via the interaction between a functional DNA and its target, two control experiments were conducted using Pb$^{2+}$-dependent DNAzyme and adenosine aptamer as models.

Figure 8F:
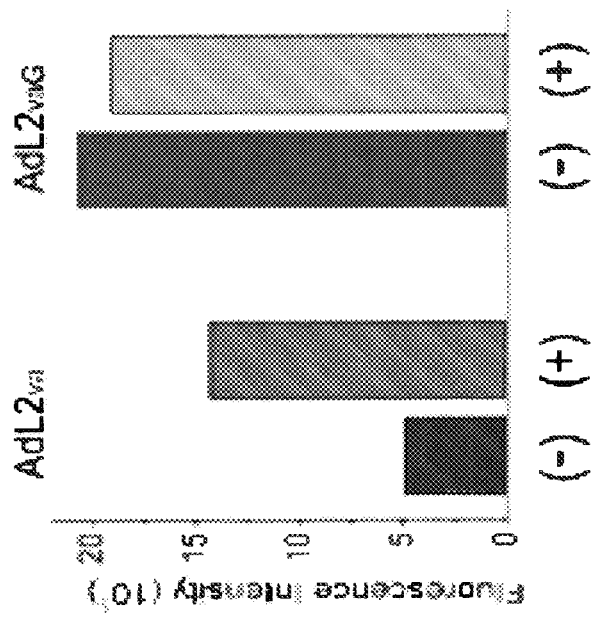
Figure 8E:
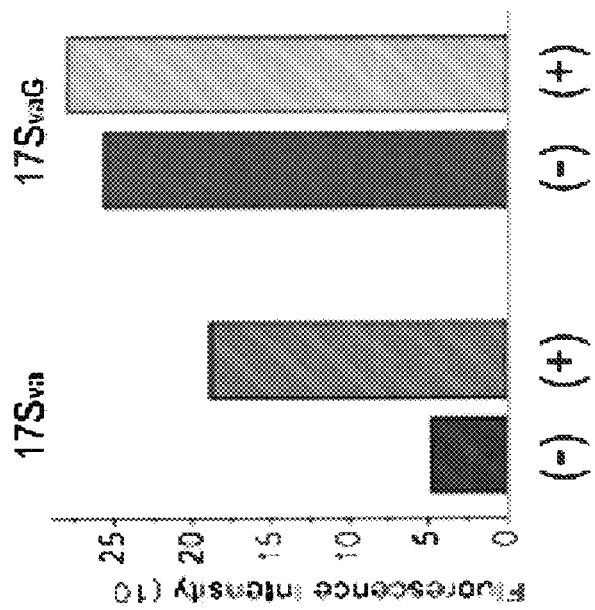

First, to confirm the role of the vacant site in the sensing, the vacant site in the loop of the 8-17 DNAzyme in Scheme 1a was "filled" by incorporating an additional G nucleotide to the 5'-end of substrate strand (named $17S_{vaG}$; SEQ ID NO: 3) to eliminate the binding site of fluorophore. In contrast to the vacant site-containing system's 200% increase of fluorescent signal in the presence of $Pb^{2+}$ as shown in FIG. 1A ($17S_{va}$/$17E_{va}$), this vacant-site-free control showed little fluorescence change (FIG. 8E). Moreover, the background fluorescence in the absence of $Pb^{2+}$ for the vacant-site-free design was much higher than that of the vacant site-containing design, probably because ATMND hardly bound to the DNA duplex without a vacant site (FIG. 8E). Similar results were also observed when the vacant site in the loop of the adenosine aptamer ($AdAP_{va}$) in FIG. 1C was filled by an incorporated G nucleotide (FIG. 8F). These results indicate that the vacant site, which serves as binding site of fluorophore, was needed for the performance of these label-free fluorescent functional DNA sensors composed of unmodified DNA.

Figure 8H:
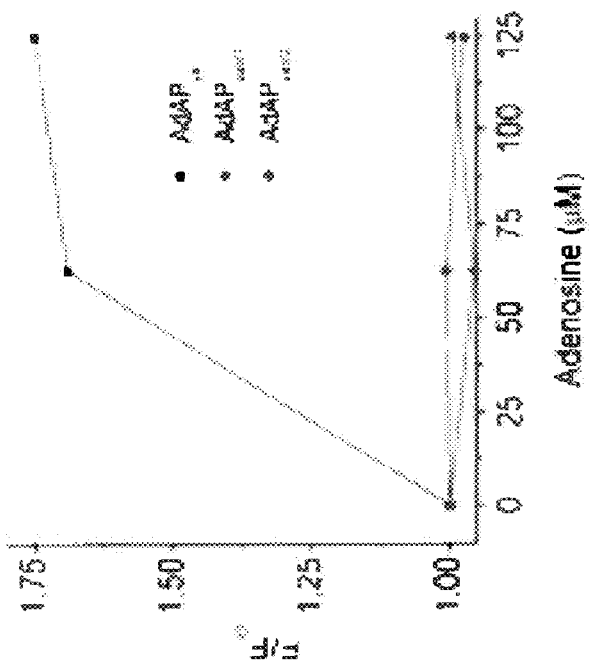
Figure 8G:
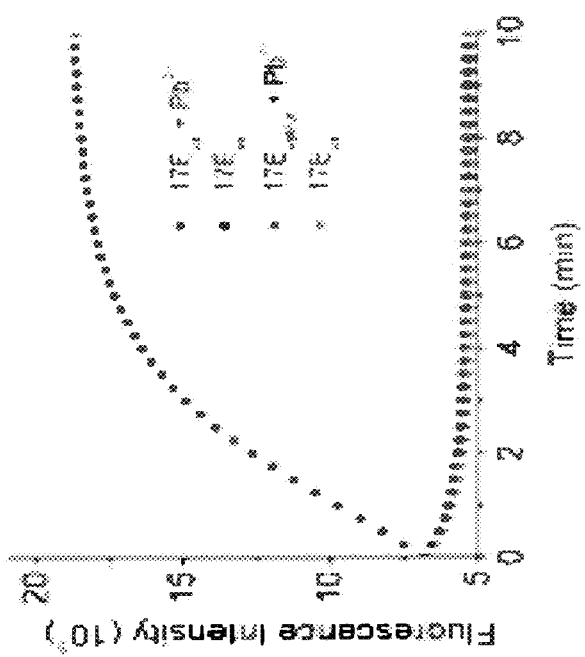

To confirm the role of the functional DNA sequences in the sensing, an inactive mutant of the $Pb^{2+}$-dependent 8-17 DNAzyme (named $17E_{vaMut}$; SEQ ID NO: 4; Li et al., *Nucleic Acids Res.* 2000, 28, 481-488; Li et al., *J. Am. Chem. Soc.* 2000, 122, 10466-10467; Brown et al., *Biochemistry* 2003, 42, 7152-7161) was investigated under the same conditions as a control of its active analogue ($17E_{va}$) in FIG. 1A. As shown in FIG. 8G, the inactive DNAzyme could quench the fluorescence of ATMND as efficiently as active $17E_{va}$ in the presence of $17S_{va}$ because a vacant site was formed within the DNA duplex in both cases. However, the addition of $Pb^{2+}$ could result in the recovery of ATMND's fluorescence only for $17E_{va}$ but not for $17E_{vaMut}$, indicating that the fluorescence enhancement was indeed the result of catalytic cleavage of substrate by DNAzyme.

Similarly, two inactive adenosine aptamers (named $AdAP_{vaM1}$ and $AdAP_{vaM2}$; SEQ ID NOS: 6 and 7; Liu and Lu, *Angew. Chem., Int. Ed.* 2006, 45, 90-94; Huizenga and Szostak, *Biochemistry* 1995, 34, 656-665) could partially quench the fluorescence of ATMND when they formed vacant sites with $AdL1_{va}$ (FIG. 8H) and $AdAP_{va}$. However, no fluorescence change was observed even when a high concentration of adenosine was present.

These results indicate that the activity of a DNAzyme or the binding of an aptamer, and the subsequent perturbation of the vacant site and release of ATMND, was the origin of fluorescence enhancement.

EXAMPLE 6

Sensor Performance in a Complex Sample Medium and Real-World Samples

After demonstrating the good sensitivity and selectivity of the sensors in simple buffered solutions, the sensors' performance in a more complex sample matrix was examined.

Figure 8I:
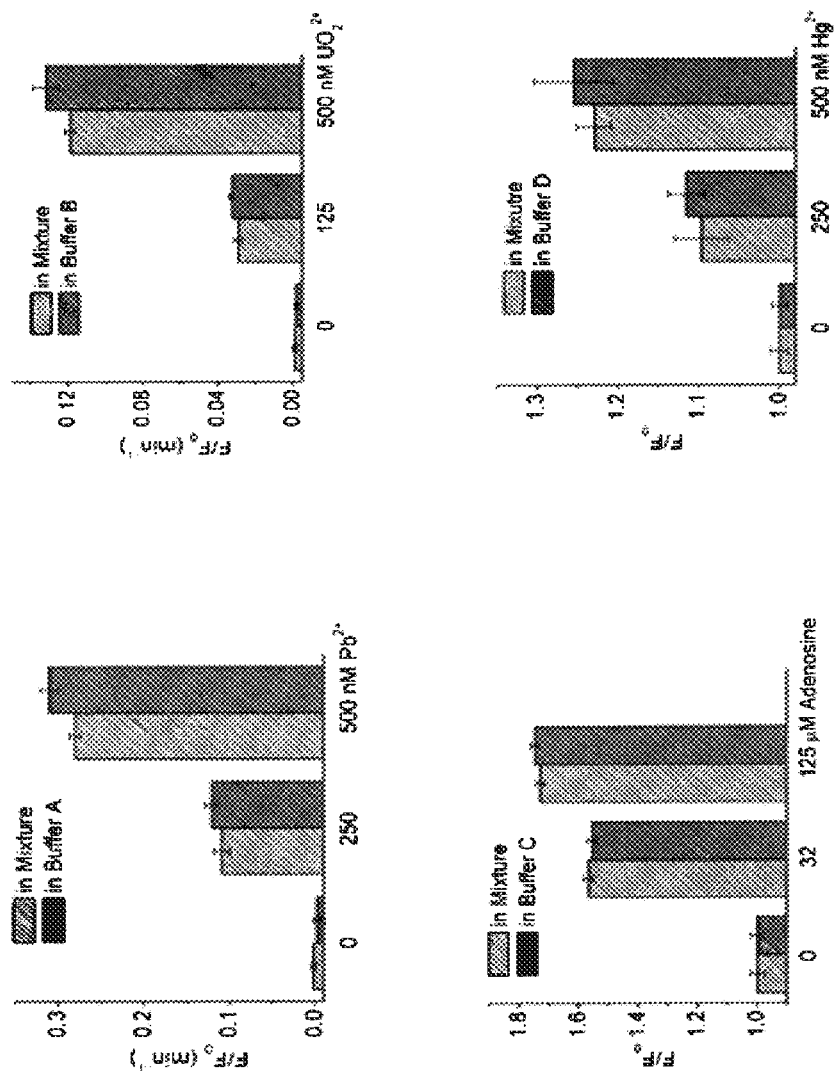

As shown in FIG. 8I, both the $Pb^{2+}$ and $UO_2^{2+}$ sensors displayed a specific response to the corresponding metal ion at low nanomolar concentrations in samples containing 1 µM $Cd^{2+}$, $Fe^{2+}$, $Ni^{2+}$, $Co^{2+}$, $Ca^{2+}$, $Mg^{2+}$, and the responses were similar to those obtained in the absence of these competing metal ions. The adenosine sensor was also tested in the presence of an additional 0.5 mM cytidine and uridine, with results consistent with those obtained in the absence of these competing nucleotides (FIG. 8I).

Figure 8J:
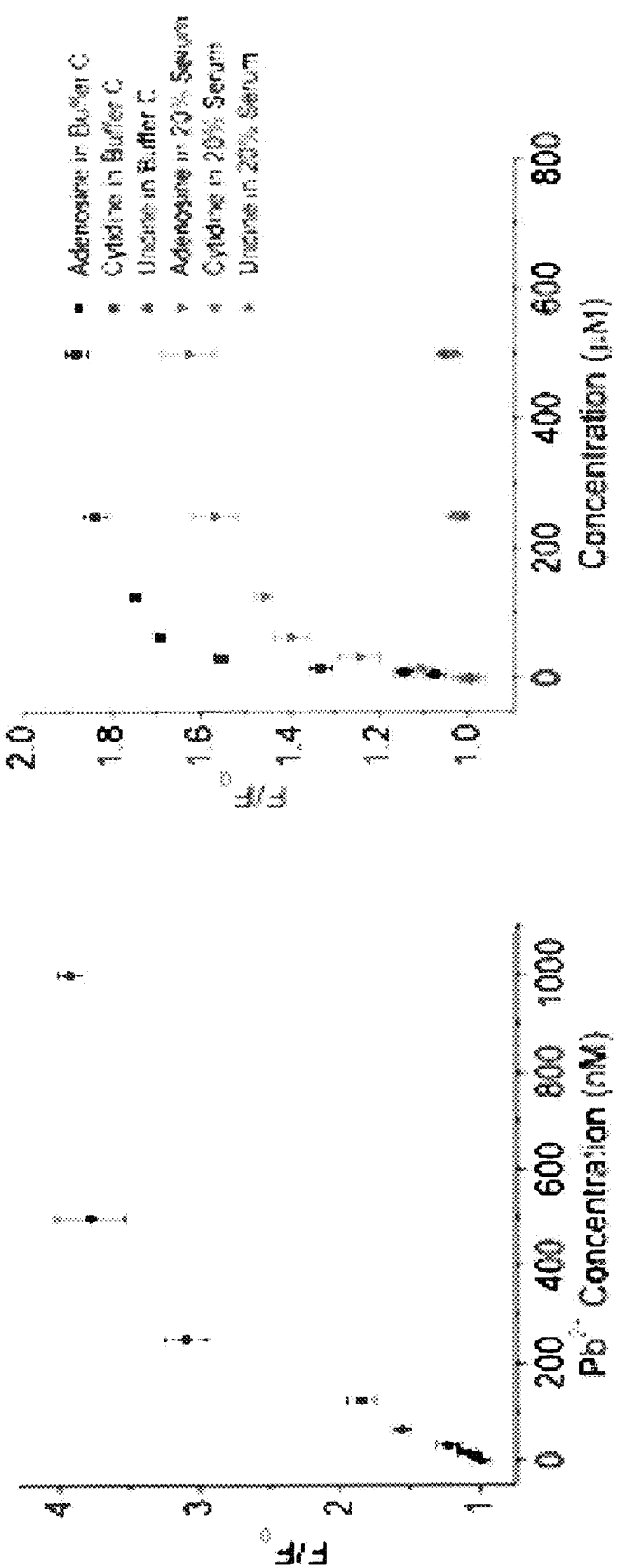

To explore their potential applications in real sample analysis, the $Pb^{2+}$ sensor and adenosine sensors designed here were used to quantify $Pb^{2+}$ in drinking water and adenosine in 20% human serum, respectively. First, calibration curves were obtained by using drinking water and serum containing different amounts of analyte (FIG. 8J). Then, blind tests were conducted using the calibration curves to evaluate the reliability of the method.

As shown in Table 1, the results demonstrate that the sensors were successful in detecting their respective targets in the real-world samples.

TABLE 1

Detection of $Pb^{2+}$ and adenosine in drinking water and human serum.

|  | Added | Found | Recovery (%) | SD (%), n = 4 |
|---|---|---|---|---|
| $Pb^{2+}$ in drinking water | 60.0 nM | 57.8 nM | 96.3 | 6.9 |
|  | 250 nM | 262 nM | 104.8 | 4.3 |
| Adenosine in 20% human serum | 32.0 µM | 30.6 | 95.6 | 4.8 |
|  | 125 | 121 | 96.8 | 5.5 |

EXAMPLE 7

Materials and Methods for Abasic Site Approach

This example provides the materials and methods used for the results described in Examples 8-12, which describe the introduction of an abasic site called dSpacer into duplex regions of DNAzymes and aptamers.

In the following sequences "X" is the abasic site/dSpacer $Pb^{2+}$-dependent DNAzyme:

$17E_{ab}$
                                                            (SEQ ID NO: 16)
5'-ACAGACATCTCTTCTCCGAGCCGGTCGAAATAGXGAG-3'

$17E_G$
                                                         (SEQ ID NO: 17)
5'-ACAGACATCTCTTCTCCGAGCCGGTCGAAATAGGGAG-3'

Substrate (a DNA/RNA chimera with a single RNA nucleotide linkage):

(SEQ ID NO: 18)
17S    3'-TGTCTGTAGAGAAGGrATATCCCTC-5'

Adenosine aptamer:

(SEQ ID NO: 19)
AAP    5'-TGTCGTTGACCTGGGGGAGTATTGCGGAGGAAGGT-3' ssDNAs for hybridization with aptamer:

(SEQ ID NO: 20)
$L1_{ab}$    3'-AGCAACTGXACC-5'

(SEQ ID NO: 21)
$L2_{ab}$    3'-AGCAACTGXACCC-5'

(SEQ ID NO: 22)
$L3_{ab}$    3'-AGCAACTGXACCCC-5'

(SEQ ID NO: 23)
$L4_{ab}$    3'-ACAGCAACTGXACCCC-5'

(SEQ ID NO: 24)
$L2_G$    3'-AGCAACTGGACCC-5'

Fluorescence measurements: For a standard $Pb^{2+}$ measurement using modified 8-17 DNAzymes, 480 µL buffer A (25 mM HEPES pH 7.0 and 100 mM NaCl), 5 μL ATMND solution (100 μM), 5 μL substrate 17S (102 μM), and 10 μL DNAzyme 17E$_{ab}$ or 17E$_G$ (107 μM) were added sequentially into a 1.5 mL microcentrifuge tube and upon vortexing, the tube was allowed to stand at room temperature for 2 min. Since no obvious difference was obtained in the results whether the mixture was annealed (by heating to 80° C. and then cooled to room temperature in 30 min.) or not, the annealing step was skipped in all the fluorescent measurements described in this study for further simplification. The solution was then transferred to a cuvette in a FluoroMax-P fluorimeter (HORIBA Jobin Yvon Inc., USA) with a constant temperature control at 5° C. After 6 min to allow the temperature to reach equilibrium, 5 μL of Pb$^{2+}$ stock solution in buffer A was added to the cuvette and followed by vortexing, and time-dependent fluorescent measurement at ex/em=358/405 nm was immediately started. Typically, the rate of fluorescence enhancement within 3~5 min after Pb$^{2+}$ addition was calculated for all the measurements. However, when Pb$^{2+}$ concentration was high (at micromolar levels), the cleavage reaction was extremely fast and therefore, only the initial rates for the first 30 s were calculated.

In a standard adenosine measurement, 450 μL buffer B (10 mM HEPES pH 7.0, 100 mM NaCl and 1 mM EDTA), 5 μL aptamer AAP (91.8 μM), 6.25 μL ssDNA L1$_{ab}$~L4$_{ab}$ or L2$_G$ (93.7 μM), and 50 μL ATMND solution (5 μM) were added sequentially into a 1.5 mL microcentrifuge tube. After vortexing, the tube was allowed to stand at room temperature for 1 min. Like in the Pb$^{2+}$ measurement using DNAzyme described above, we found no obvious difference in the results whether the mixture was annealed or not and therefore all measurements were carried out without annealing. A 5 μL of adenosine stock solution in buffer B was added to the above mixture followed by vortexing and then was allowed to stand at room temperature for 1 min. The solution was then transferred to a cuvette in the fluorimeter with a constant temperature control at 5° C. After 10 min, the fluorescence intensity at ex/em=358/405 nm was recorded. The sample showed a stable intensity signal from 8~30 min upon transferring it to the fluorimeter. A lower ATMND concentration (500 nM) was used in the adenosine experiment than in the Pb$^{2+}$ experiment (1 μM) in order to achieve lower background fluorescence, because the binding affinity of ATMND to the aptamer duplex is weaker than that with the DNAzyme duplex.

EXAMPLE 8

Design of Pb$^{2+}$-Dependent DNAzyme Containing a dSpacer Abasic Site

It was previously reported (Liu and Lu, *J. Am. Chem. Soc.* 2005, 127, 12677-12683) that a dSpacer-DNA that was originally developed by Teramae's group (Liu and Lu, *Nat. Protoc.* 2006, 1, 246-252; Nutiu and Li, *Angew. Chem., Int. Ed.* 2005, 44, 1061-1065; Nutiu, R.; Li, Y. *J. Am. Chem. Soc.* 2003, 125, 4771-4778) as sensors for nucleobase recognition can be converted into a general platform for designing label-free functional DNA sensors. These sensors are highly sensitive and feature a controllable fluorophore-binding site. It was demonstrated that a label-free approach could be achieved by incorporating Spacer C3 into adenosine aptamers (Wernette et al., *Langmuir* 2007, 23, 9513-9521; Wernette et al., *Analyst* 2006, 131, 41-47). Nevertheless, these designs still require that the DNA be modified with dSpacer or Spacer C3, which is not only expensive to make, but also difficult to introduce into biological system through encoding. Developing label-free functional DNA sensors that use unmodified DNA to achieve a controllable fluorophore-binding site, and extending this method to both DNAzymes and aptamers remain as unmet challenges.

The sensor design was based on inserting a dSpacer in functional DNA molecules such as DNAzymes and aptamers for label-free sensing applications. Through complementary hydrogen bonding toward the opposite nucleobase and stacking effects from flanking nucleobases, a fluorophore could bind to the abasic site in dsDNA, and lead to its fluorescence quenching. In the presence of the specific target, the DNAzyme-target or the aptamer-target interactions would result in the dehybridization of the DNA duplex region containing an abasic site, thereby releasing the fluorophore into the solution and recovering its quenched fluorescence. By controlling the position of the abasic site for binding different fluorophores, these fluorescent sensors can be used for detecting and quantifying a broad range of targets.

The fluorophore-labeled 8-17 DNAzyme system was used to demonstrate label-free Pb$^{2+}$ detection using an abasic site and to compare the performance of previous systems. Based on the 8-17 DNAzyme, two mutations at the 3'-end of the enzyme strand, 17E, were introduced (FIG. 9A): a T base was mutated to an abasic site for label-free fluorophore binding, and another T base at the 3'-end was eliminated for efficient dehybridization of the abasic site-containing duplex region after the substrate, 17S, was cleaved. This modified enzyme strand containing the abasic site was called 17E$_{ab}$ (SEQ ID NO: 16).

In the absence of Pb$^{2+}$, the fluorophore ATMND binds to the abasic site in the duplex region of the 17E$_{ab}$ (SEQ ID NO: 16) and 17S (SEQ ID NO: 18) (FIG. 9A), effectively quenching the fluorescence of ATMND. In the presence of Pb$^{2+}$, on the other hand, the substrate 17S would be cleaved, resulting in release of the cleavage products and formation of ssDNA. In such a case, the binding affinity of ATMND to the ssDNA region would decrease significantly, causing ATMND released and thus enhancing the fluorescent signal.

EXAMPLE 9

Formation of Duplex DNA Between 17E$_{ab}$ and 17S

To determine whether 17E$_{ab}$ and 17S could form a duplex that was essential for both ATMND binding into the abasic site as well as Pb$^{2+}$-dependent catalytic activity, the fluorescence spectra of ATMND in the absence and in the presence of 17E$_{ab}$ and 17S were collected.

When alone in solution at a concentration of 1 μM, ATMND exhibited strong blue fluorescence emission with a band centered around 405 nm (FIG. 9C, plot 1). Further addition of either 2.14 μM 17E$_{ab}$ or 1.02 μM 17S resulted in little change in the fluorescence spectra of ATMND, suggesting that the interaction between ATMND and ssDNA of either 17E$_{ab}$ or 17S was negligible. In contrast, in the presence of both 17E$_{ab}$ and 17S, the fluorescence emission of ATMND was significantly quenched by more than 90% (FIG. 9c, plot 2), which is attributable to the effective binding of ATMND to the abasic site in DNA duplex formed by 17E$_{ab}$ and 17S (Yoshimoto et al., *J. Am. Chem. Soc.* 2003, 125, 8982-8983). Therefore, the hybridization of 17E$_{ab}$ and 17S was efficient and the duplex DNA was conducive for the Pb$^{2+}$-catalyzed reaction and sensing applications.

EXAMPLE 10

Pb$^{2+}$-Catalyzed Cleavage of 17S in the 17E$_{ab}$-17S Duplex

To demonstrate the effect of the abasic site on the Pb$^{2+}$-dependent activity, an enzymatic activity assay using PAGE was used, and it was observed that in the absence of ATMND, the abasic site within the DNAzyme binding arm weakened the substrate/DNAzyme binding interaction, resulting in reduced activity. However, addition of ATMND restored the substrate/DNAzyme binding affinity and rendered similar activity compared to unmodified enzyme (FIG. 9E).

To confirm addition of $Pb^{2+}$ could result in the cleavage of the 17S and release of ATMND, 1 μM of $Pb^{2+}$ was added to a solution containing 1 μM ATMND, 2.17 μM $17E_{ab}$ and 1.02 μM 17S and more than a 7-fold fluorescence enhancement was observed after 15 min (FIG. 9C, plot 3). To ensure that the fluorescence increase was due to the presence of $Pb^{2+}$, 1 mM EDTA was added to the above solution as a control before $Pb^{2+}$ addition. Little change in fluorescence spectra could be observed under the same conditions (FIG. 9C, plot 4), suggesting the essential role of $Pb^{2+}$ for the catalytic reaction. When the essential G•T wobble pair in the 8-17 DNAzyme (FIG. 9A) was replaced with a G-C Watson-Crick base pair, the DNAzyme exhibited no $Pb^{2+}$-dependent activity (FIG. 9F), similar to that of original 8-17 DNAzyme. These results demonstrate that the new label-free DNAzyme sensor construct did not perturb the original activity of the 8-17 DNAzyme, which was crucial for the fluorescence enhancement.

A kinetics study was carried out to monitor the time-dependent emission of ATMND at 405 nm after the reaction was initiated through the addition of various amounts of $Pb^{2+}$ (FIG. 10A; for lower $Pb^{2+}$ concentration range, FIG. 9G). The rate of fluorescence enhancement ratio ($\Delta F/F_0$ per minute) showed an approximately linear relationship with $Pb^{2+}$ concentration ($C_{pb}^{2+}$) at least in 0~1 μM range as $\Delta F/F_0$ (min$^{-1}$)= $1.697 \times C_{Pb}^{2+}$ (μM) (FIG. 10B).

For $Pb^{2+}$ measurements, the rate ($\Delta F/F_0$ per minute) within 3~5 min after $Pb^{2+}$ addition was recorded rather than fluorescence intensity at a specific time point, because the rate measurement was much less vulnerable to fluctuations in the background fluorescence of the samples. This new method was very sensitive to the concentration of $Pb^{2+}$, with a detection limit measured by $3\sigma_b$/slope ($\sigma_b$, standard deviation of the blank samples) of 4 nM, which was even lower than previously reported labeled fluorescent methods (Li and Lu, *J. Am. Chem. Soc.* 2000, 122, 10466-10467; Liu and Lu, *J. Am. Chem. Soc.* 2003, 125, 6642-6643.; Liu and Lu, *J. Am. Chem. Soc.* 2005, 127, 12677-12683). In addition, this method maintained excellent selectivity over other divalent metal ions, such as $Mg^{2+}$, $Ca^{2+}$, $Sr^{2+}$, $Ba^{2+}$, $Mn^{2+}$, $Fe^{2+}$, $Co^{2+}$, $Zn^{2+}$, $Ni^{2+}$, $Hg^{2+}$, $Cd^{2+}$ (FIG. 11).

To confirm the role of the abasic site in this method, a control DNAzyme $17E_G$ (SEQ ID NO: 17) of the same DNA sequence with $17E_{ab}$, except that the abasic site was replaced by a G, was investigated under the same conditions. Little fluorescence quenching of ATMND was observed when the fluorophore was added to a solution containing $17E_G$ and 17S, and subsequent addition of $Pb^{2+}$ to the solution yielded negligible fluorescence enhancement (FIG. 12A). These results demonstrate that there was little binding of ATMND to the completely complementary $17E_G$-17S duplex, and the $Pb^{2+}$-dependent catalytic cleavage of 17S by $17E_G$ could not be transformed into a fluorescence signal change in the absence of the abasic site.

EXAMPLE 11

Design of Adenosine-Dependent Aptamer Containing a Dspacer Abasic Site

The DNAzyme-based sensing results were extended to aptamers. The adenosine aptamer (Liu and Lu, *Angew.* *Chem., Int. Ed.* 2006, 45, 90-94; Liu and Lu, *Nat. Protoc.* 2006, 1, 246-252) was used as a model system. The challenge was to transform the structural switching (Nutiu and Li, *J. Am. Chem. Soc.* 2003, 125, 4771-4778; Nutiu and Li, *Angew. Chem., Int. Ed.* 2005, 44, 1061-1065; Nutiu and Li, *J. Am. Chem. Soc.* 2003, 125, 4771-4778) of the aptamer upon target-binding into fluorescence enhancement. Because the location of ATMND on the DNA was controllable in this label-free method, an abasic site-containing ssDNA linker (called $L1_{ab}$; SEQ ID NO: 20) was designed to hybridize to the adenosine aptamer DNA (called AAP, SEQ ID NO: 19, see FIG. 9B). In the absence of the target adenosine, ATMND bound strongly to the abasic site in the duplex region, resulting in suppression of its fluorescent signal. In the presence of adenosine, the aptamer bound adenosine strongly, thereby releasing the abasic-site containing the ssDNA and ATMND from the duplex DNA into solution and recovering the quenched fluorescence of ATMND. Consequently, adenosine could be effectively detected through the fluorescence enhancement response.

EXAMPLE 12

Performance of Label-Free Fluorescent Adenosine Detection

To demonstrate the binding of the fluorophore to the AAP-$L1_{ab}$ duplex, ATMND was added to a solution containing AAP (SEQ ID NO: 19) and $L1_{ab}$ (SEQ ID NO: 20). ATMND underwent fluorescence quenching upon binding to the AAP-$L1_{ab}$ duplex (FIG. 9D, plot 1 and 2), similar to that of the $17E_{ab}$-17S system. Addition of adenosine to the solution resulted in recovering some of the quenched fluorescence of ATMND (FIG. 9D, plot 3), probably through structural switching of AAP that allows single strand DNA formation and release of ATMND from DNA duplex into solution. The kinetics of the binding and subsequent switching was fast, and a stable signal over at least 30 min could be obtained, making it possible to record fluorescence spectra 10 min after adenosine addition, at which point the equilibrium was established. The emission intensity at 405 nm rose with increasing concentration of adenosine in solution, with a linear response in the range of 0~25 μM and a detection limit ($3S_b$/slope, $\sigma_b$, standard deviation of the blank samples) of 3.4 μM (FIG. 13A). This relatively low detection limit may be ascribed to the short duplex region of AAP-$L1_{ab}$, which facilitated the binding of adenosine and release of $L1_{ab}$.

The selectivity of this sensor toward adenosine over two other nucleotides, uridine and cytidine, was very high, with little fluorescence enhancement observed for them even in concentrations at the millimolar level (FIG. 13A). Guanosine was not tested because it is not soluble in aqueous solutions at the millimolar concentration range. In addition, five mutants of AAP were also investigated under the same conditions (SEQ ID NOS: 25 and 39-42). These mutants could only induce little or no fluorescence enhancement response toward adenosine compared to APP (FIG. 13B), indicating that the activity of the aptamer was crucial for the fluorescence enhancement.

EXAMPLE 12

Tuning the Dynamic Range of an Aptamer-Containing Sensor

Most analytes of interest have varied concentration ranges in different compartments of cells or at different locations in the environment. A practical sensor needs to have a tunable dynamic range that matches the concentration ranges for the different locations; too strong a binding by the sensor can perturb the equilibrium of the sensing environment while too weak a binding by the sensor may not allow detection. Previously it has been shown that DNAzyme-based sensors can be designed to have a tunable dynamic range (Liu and Lu, *J. Am. Chem. Soc.* 2003, 125:6642-6643; Liu and Lu, *J. Am. Chem. Soc.* 2003, 125:6642-6643). However, the same strategy cannot be applied to aptamers because catalytic cleavage and turnovers were required in tuning the dynamic range of the DNAzyme sensors.

Herein disclosed is a new strategy of tuning the dynamic range of aptamers by varying the length of the abasic site-containing ssDNA, $L1_{ab}$~$L4_{ab}$ (SEQ ID NOS: 20-23), which hybridize to AAP. As shown in FIG. 14, with increasing length of $L1_{ab}$ to $L2_{ab}$~$L4_{ab}$ by more complementary base pairs to AAP, the dynamic range of the sensor can be tuned to be 3.4-200 μM, 25-400 μM, 100 μM-4 mM, and 200 μM-4 mM, respectively. Thus, increasing the number of base pairs in the duplex region formed by AAP with ssDNA from $L1_{ab}$ to $L4_{ab}$, the duplex becomes more stable, making it more difficult to carry out the structural switching that leads to fluorescence enhancement under the same experimental conditions. To achieve the same effects, more adenosine is needed. Therefore, by designing appropriate number of base pairs in the ssDNA/aptamer duplex region that is critical to the adenosine-induced APP structural switching, the dynamic range of this label-free fluorescent method can be controlled, facilitating adenosine detection over broad concentration ranges.

Figure 12B:
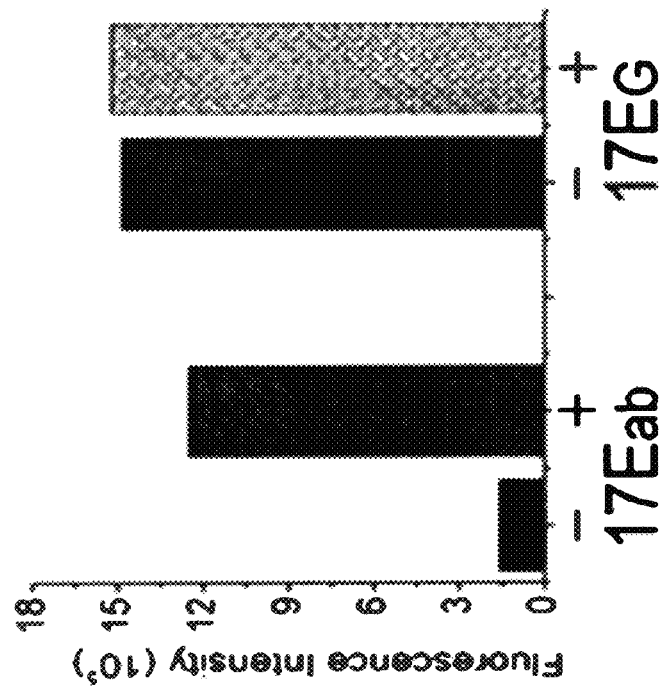

To ensure that the effects observed were due to the abasic site, a control ssDNA $L2_G$ (SEQ ID NO: 24), which is the same with $L2_{ab}$ except that the abasic site is replaced by a G base, was used under identical conditions. Such a control showed neither fluorescence quenching of ATMND with $L2_G$-AAP in the absence of adenosine nor subsequent recovery of quenching in the presence of adenosine (FIG. 12B), indicating the essential role of the abasic site.

In summary, by incorporating an abasic site of dSpacer into the duplexes of either DNAzymes or aptamers, the label-free fluorescent detection of $Pb^{2+}$ and adenosine with a fluorescent signal enhancement response was achieved using ATMND as an extrinsic fluorophore. Detection limits as low as 4 nM for $Pb^{2+}$ and 3.4 μM for adenosine were obtained for this label-free method, which also showed good selectivity toward $Pb^{2+}$ and adenosine over other divalent metal ions and nucleotides, respectively. The effect of the hybridized base-pair number on the efficiency of structural switching upon target binding with the adenosine aptamer provided the opportunity to tune the dynamic range of adenosine detection from the micromolar to the millimolar range. Since FNAs for many other metal ions and organic molecules can be obtained through in vitro selection, and the described method is independent of exact sequences used, and the location of fluorophore binding in the nucleic acid (e.g., DNA) can be controlled through the creation of abasic sites, this label-free approach can be further extended to other RNA- or DNA-based systems for detecting and quantifying a broad range of analytes.

EXAMPLE 13

Materials and Methods for Aptamer Sensor Based on Regulation of Malachite Green Fluorescence This example describes the materials and methods used for Example 14 below.

Nucleic acids were purchased from Integrated DNA Technologies, Inc. (Coralville, Iowa) with standard desalting. No further purification was performed. Malachite green and all other chemicals were purchased from Sigma-Aldrich. Buffers were prepared in Millipore water.

Sensor preparation: The sensor solution was prepared by dissolving the nucleic acid strands and malachite green in buffer. The solution was then heated to 80° C. and cooled down to room temperature in about one hour to ensure the system to fold into the structure described in FIG. 15.

Because of the poor solubility of adenosine, the highest concentration of the stock solution we can prepare is 50 mM. Thus, during the sensor preparation step, the dilution effect by the addition of adenosine was considered. In a typical procedure at the optimized conditions, 1.11 μM aptamer strand (SEQ ID NOS: 26 and 27), 1.56 μM Bridge 9-6 (SEQ ID NO: 33) and 0.67 μM MG were dissolved in 22 mM Tris buffer containing 5.56 mM NaCl, 155.6 mM KCl and 5.56 $MgCl_2$. After heating and cooling the solution as described above, 0.45 mL of the prepared solution was mixed with 0.05 mL 10-times adenosine stock solution. After 30 min, the fluorescence of the sample was measured and recorded.

Fluorescent measurements and data analysis: Fluorescence experiments were carried out on a Fluoromax-2 fluorimeter (HORIBA Jobin Yvon inc., Edison, N.J.). Emission acquisition mode was used. The fluorescence was excited by 615 nm excitation. The fluorescence at 650 nm was recorded. $F/F_0$ was plotted as sensor signal. F is the fluorescence of MG after the addition of adenosine. During optimization procedure, $F_0$ is the fluorescence of MG before addition of adenosine stock solution. For the sensor calibration curve acquisition, $F_0$ is the fluorescence of the sensor solution with addition of 0 mM adenosine (water). All the measurements were performed for 3 times and the standard deviation was plotted as the error bar.

Nucleic acid sequences: The sequences of the nucleic acids used are presented in FIG. 15. Bridging strands are named as bridge M-N, in which M is the number of the complimentary bases to the MG aptamer and N is the number of the complimentary bases to the adenosine aptamer.

Aptamer strand:

```
SEQ ID NO: 26:
5'-ACC TGG GGG AGT ATT GCG GAG GAA GGT

SEQ ID NO: 27:
5'-r(UCC CGA CUG GAA CAG GUA ACG AAU GGA)
```

Bridging Strands:

```
SEQ ID NO: 28:
5'-CAGGTTCCATT (Bridge 6-5)

SEQ ID NO: 29:
5'-CCAGGTTCCAT (Bridge 5-6)

SEQ ID NO: 30:
5'-CCAGGTTCCATT (Bridge 6-6)

SEQ ID NO: 31:
5'-CCAGGTTCCATTC (Bridge 7-6)

SEQ ID NO: 32:
5'-CCAGGTTCCATTCG (Bridge 8-6)

SEQ ID NO: 33:
5'-CCAGGTTCCATTCGT (Bridge 9-6)

SEQ ID NO: 34:
5'-CCAGGTTCCATTCGTT (Bridge 10-6)
```

Hybridization energy calculation: The energy was calculated using IDT SciTools, provided free of charge on the web by Integrated DNA Technologies, Inc. (Coralville, Iowa) to assist in the design of the system.

EXAMPLE 14

Label-Free Aptamer Malachite Green (MG) Sensor

The design of the label-free aptamer fluorescent sensor is shown in FIG. 15. The sensor contains two nucleic acid strands and MG. One strand is a chimeric conjugate of the adenosine DNA aptamer sequence (on right; SEQ ID NO: 26) and MG RNA aptamer sequence (on left; SEQ ID NO: 27), called the "aptamer strand" herein. The other is a DNA strand, called the "bridging strand" (in brown; SEQ ID NOS: 28-34), that contains sequences complimentary to both the adenosine and MG aptamers. The sequence of the bridging strand is designed so that the aptamer and bridging strands form a stable complex in buffer at room temperature to prevent the MG aptamer strand from binding MG in the solution if there is no adenosine present. Under this condition, the MG remains free in solution and almost non-fluorescent. In the presence of adenosine, however, the aptamer strand binds adenosine, leaving much less number of complimentary base pairs between the aptamer strand and bridging strand, which is less stable at room temperature, resulting in release of the bridging strand from the aptamer strand. As a consequence, the fluorescence of the MG is recovered.

The DNA/RNA chimeric aptamer described herein is expected to be less stable than all-DNA aptamer, but more stable than all-RNA aptamers. The stability can be further improved if the RNA aptamer can be replaced by a DNA aptamer that can be obtained through in vitro selection.

Sensor Optimization: Since there are two aptamers in the design, each with its own optimal buffer condition for performance, a common condition suitable for both aptamer functions was identified. Although adenosine aptamer was in vitro selected in a 20 mM Tris-acetate buffer with pH 7.6 (Huizenga and Szostak, *Biochemistry* 1995, 34, 656-665), it has been reported that adenosine aptamer-based biosensors are effective in a range of pH between 7.4 and 8.3 (Nutiu and Li, *J. Am. Chem. Soc.* 2003, 125, 4771-8; Yang et al., *J. Am. Chem. Soc.* 2008, 130, 6320-6321; Lu et al., *Chem. Commun.* 2008, 6161-6163; Liu and Lu, *J. Am. Chem. Soc.* 2007, 129, 8634-43). In addition, the $Na^+$ and $Mg^{2+}$ concentrations can be varied from 100 mM to 300 mM and from 0 to 5 mM, respectively (Id.). The system developed by Li and co-workers (Nutiu and Li, *Angew. Chem., Int. Ed.* 2005, 44, 5464-7) was used to test the performance of adenosine aptamer in different buffers, and found that the sensing performance is similar at pH between 7.4 and 8.4 and concentrations of NaCl between 150 mM and 300 mM and $MgCl_2$ between 2 mM and 5 mM.

After confirming the workable range of buffer conditions for adenosine aptamer, a common buffer condition that is also effective for MG aptamer was identified. Since MG aptamer was selected in 10 mM Na-HEPES buffer at pH 7.4, together with 100 mM KCl and 5 mM NaCl, 20 mM Tris (pH 7.4), 145 mM NaCl and 5 mM $MgCl_2$ was used as a compromise between buffers for adenosine and MG aptamers in the first trial to determine if this buffer is effective for MG aptamer. The binding of the aptamer strand and MG in the selected buffer was tested by measuring the fluorescence of MG with and without the presence of the aptamer strand. To test the role of potassium ion in the sensor performance, 1 μM aptamer strand (SEQ ID NOS: 26 and 27), bridge 6-5 (SEQ ID NO: 28) and MG in the various buffer solutions was used, and the fluorescence increase fold upon the addition of 5 mM adenosine was plotted.

A 3-order magnitude of fluorescence increase was observed in the presence of the aptamer strand (FIG. 15; SEQ ID NOS: 26 and 27), similar to that reported previously (FIG. 16A) (Babendure et al., *J. Am. Chem. Soc.* 2003, 125, 14716-7). The result shows that the aptamer strand and the common buffer condition result in comparable performance as previously reported MG aptamer and buffer conditions.

Since the MG aptamer was selected in buffer containing potassium, the effect of replacing NaCl with KCl in the buffer to increase the performance of the sensor was determined. The sensor performance using bridge 6-5 (SEQ ID NO: 28; FIG. 15) in buffers containing 20 mM Tris (pH 7.4), 5 mM $MgCl_2$ and 145 mM in total monovalent metal ions, but with different combination of $Na^+$ and $K^+$ was determined. Variation of potassium concentration did not change the signal significantly (around 10%, FIG. 16B). Monovalent metal ions are necessary for the MG aptamer affinity because the DNA strand has to fold, during which the negative charge on the DNA backbone has to be neutralized. As $K^+$ and $Na^+$ has the similar ability to help DNA fold, variation of $K^+$ concentration did not affect the sensor performance significantly. Therefore, 20 mM Tris (pH 7.4), 5 mM $MgCl_2$, 140 mM KCl and 5 mM NaCl was used as the optimized buffer to make it as close as possible to the buffer in which MG aptamer was selected. Since two aptamers are used in this label-free system, each with its own optimized condition, the range of optimal conditions is much narrower than that of the labeled systems.

Bridging Strand Optimization: Having arrived at the buffer conditions, the optimal sequence for the bridging DNA strands was determined. The design shown in FIG. 15 depends on thermodynamics of DNA hybridization and adenosine and MG bindings to their respective aptamers, which include the binding of adenosine to its aptamer, the binding MG to its aptamer, and the interaction between the aptamer strand and the bridging strand. For this design to work, several conditions must be met. First, the base parings between the aptamer strand and the bridging strand have to prevent the MG aptamer from binding MG in the absence of adenosine. At the same time, however, the base parings between the aptamer strand and the bridging strand should not inhibit the binding of adenosine if adenosine is present. Finally, once adenosine binds to adenosine aptamer and starts structural switching, the hybridization between the MG aptamer part and the bridging DNA should not be very stable at room temperature to ensure the release of it and binding of the aptamer strand to MG.

The bridging strand that contains 6 bases that are complementary to adenosine aptamer and various numbers of bases that are complementary to MG aptamer (Bridge 6-6, 7-6, 8-6, 9-6 and 10-6 were tested; SEQ ID NOS: 28-34, respectively). During the optimization procedure, the maximum fluorescence fold increase upon the addition of the adenosine which was chosen as the signal output of the sensor. Meanwhile kinetics is the consideration. That the equilibrium was reached in less than 30 min was ensured. The sensor was prepared by dissolving 1 μM aptamer strand, bridging strand and MG in the optimized buffer. Upon addition of 5 mM adenosine to the sensor solution, fluorescence ($F/F_0$, Ex: 615 nm, Em: 650 nm) increases when the number of bridging strand base complementary to MG aptamer increases from 6 to 9, and then deceases when the number is 10 (FIG. 17).

Based on these results, Bridge 9-6 (SEQ ID NO: 33) is the optimal for this aptamer. These aptamer and bridging strands form a stable complex in buffer at room temperature, with a hybridization energy (ΔG) of −29.52 kcal/mol, calculated based on IDT SciTools. In the absence of adenosine, such a stable complex prevent the MG aptamer strand from binding MG. However, the 6 base pairs of the bridging strand to the adenosine aptamer (with a ΔG of −11.03 kcal/mol) are not strong enough to inhibit the binding of the aptamer strand towards adenosine. Therefore, in the presence of adenosine, the aptamer strand binds adenosine, leaving only 9 base pairs between the aptamer strand and bridging strand. Such a 9 base pair duplex has a ΔG of only 16.55 kcal/mol, and is not very stable at room temperature. Thus, some bridging strands are released from the aptamer strands and the MG aptamers are recovered. As a result, part of the free MG molecules binds the aptamer strand, giving an increase in the fluorescent signal.

Since there are three DNA species (the aptamer and bridging strands and MG) in the system, it offers a chance to optimize the ratio of the three species separately to increase the performance of the sensor. First, both DNA strands were kept 1 μM and MG concentration was varied. As presented in FIG. 18A, MG=0.6 μM has the best performance. The aptamer strand and MG concentrations were then set to 1 μM and 0.6 μM, respectively, and the concentration of the bridging strand (bridge 9-6; SEQ ID NO: 33) varied. As shown in FIG. 18B, 1.0 μM and 1.4 μM of the Bridge 9-6 have similar fluorescence fold increase in the presence of 5 mM adenosine (around 10% difference). 1.4 μM of the Bridge 9-6 was selected to ensure the complete hybridization of the aptamer strand to the bridge strand. Therefore the optimal sensor design is for 1.4 μM Bridge 9-6 to be complementary to 1 μM aptamer strand while in the presence of 0.6 μM MG.

Performance of the Sensor: Under the optimal sensor design and buffer conditions, minimal fluorescence was observed in the absence of adenosine (bottom trace in FIG. 19A). Upon addition of 5 mM adenosine, however, a 12 fold increase in fluorescence was observed (top trace in FIG. 19A), indicating that the binding of adenosine by the adenosine aptamer caused the release of the bridging strand, recovering the affinity of the MG aptamer, which then binds MG, resulting in a fluorescence increase. To quantify concentrations of adenosine based on the increase in MG fluorescence, we measured the saturated fluorescence upon addition of different concentrations of adenosine. The sensor solution concentration was diluted to 20% of what was described to save the material. The results shown in FIG. 19B indicate that the fluorescence of MG increases with an increasing concentration of adenosine, reaching ~12 fold fluorescence increase around 5 mM adenosine. The inset of FIG. 19B shows the region between 0 and 1 mM adenosine where a linear relationship was observed between adenosine concentration and MG fluorescence. A detection limit of 20 μM at 90% confidence level was calculated, which is comparable with other adenosine aptamer-based sensors. The sensitivity of the sensor is dependent on the binding affinity of the aptamer. Usually a good aptamer-based sensor has a detection limit that is comparable to the $K_d$ value of the aptamer. A higher sensitivity for the sensor can be obtained if an aptamer with higher binding affinity is used. The binding affinities of the aptamer strand towards adenosine and MG are decreased because of the steric hindrance. However, the detection limit of this sensor is comparable to other adenosine aptamer-based sensors because the affinity of both aptamers is not significantly affected and the label-free design helps to lower the background.

To test the selectivity of the sensor, 5 mM cytidine or uridine, the highest concentration tested for adenosine, was added to the sensor solution and no fluorescence increase was observed (see FIG. 19C). These results indicate that the sensor is specific to adenosine. Guanidine was not used due to poor solubility.

In summary, it is shown herein that coupling of adenosine aptamer strand with MG aptamer strand through a bridging strand in which the fluorescence of malachite green can be regulated by the presence of adenosine. This system has sensitivity and selectivity comparable to other adenosine sensor systems, with the benefit of no need for labeling of the DNA with fluorophores. As the design is based purely on DNA hybridizations, it can be more generally applied to other aptamers for detecting a broad range of analytes.

EXAMPLE 15

Label-Free Malachite Green (Mg) Aptamer-L-Arginine Aptamer Sensor

This example describes a label-free sensor based on MG aptamer and L-arginine RNA aptamer, and demonstrates the applicability of the sensor design for detecting other target agents using RNA aptamers.

An RNA aptamer for the recognition of L-arginine is known (Geiger et al., *Nucleic Acids Res.* 1996, 24:1029-1036). The aptamer was developed into a fluorescent sensor based on the structure switching of the aptamer (Null et al., *Analyst,* 2010, 135:419-422). This aptamer can be applied in the design of the label-free sensor based on MG aptamer.

The nucleic acid strands are shown below.

Aptamer strand:

```
                                         SEQ ID NO: 27
SEQ ID NO: 61:
5'-AUG AUA AAC CGA UGC UGG GCG AUU CUC CUG AAG

UAG GGG AAG AGU UGU CAU
```

Bridging strands:

```
SEQ ID NO: 62:
5'-T TAT CAT TCC ATT CGT (Bridge 9-7)

SEQ ID NO: 63:
5'-TT TAT CAT TCC ATT CGT (Bridge 9-8)

SEQ ID NO: 64:
5'-GTT TAT CAT TCC ATT CGT (Bridge 9-8)

SEQ ID NO: 65:
5'-G GTT TAT CAT TCC ATT CGT (Bridge 9-10)

SEQ ID NO: 66:
5'-GTT TAT CAT TCC ATT CGT T (Bridge 10-8)

SEQ ID NO: 67:
5'-TT TAT CAT TCC ATT CG (Bridge 8-8)
```

The aptamer strand is the conjugate of the MG aptamer (SEQ ID NO: 27) and L-arginine aptamer (SEQ ID NO: 61). Six bridging strands (SEQ ID NOS: 62-67) are proposed by varying the numbers of the complimentary bases between the bridging strand and both aptamers. Although not listed, other bridging strands can be designed to obtain the best sensor performance.

The sensor development procedure in Example 14 can be used. For example, the buffer condition can be investigated. Because of the difference of the selection buffer of the two aptamers, a compromise has to be made. The proposed buffer component is 50 mM HEPES with pH 7.0, 100 mM NaCl and 5 mM $MgCl_2$. The applicability of the buffer can be tested by dissolving 1 µM MG and the aptamer strand in the buffer. The presence of the aptamer strand should enhance the MG fluorescence by 1000 fold. If not, the buffer formula should be improved by making it closer (in the aspects of pH value and ion strength) to the MG aptamer selection buffer.

After the finding the optimal buffer, the optimal bridge strand should be identified, for example by dissolving the bridging strand, aptamer strand and MG in buffer. The concentration may vary between 200 nM to 2 µM. After the denaturing and annealing of the sensor solution, L-arginine is added to reach a concentration of 5 mM. The fluorescence can be measured after a fixed time, e.g. 20 minutes. The bridge strand that leads to the highest fold of fluorescence increase is the optimal bridging strand.

The ratio of the three species is optimized thereafter. Similar to Example 14, the ratio of the nucleic acid strands can be kept 1:1 and the concentration of MG varied. The sensor performance can be compared by comparing the fluorescence increase with 5 mM L-arginine. The ratio of aptamer strand can then be held constant and MG optimal and vary the concentration of the bridging strand to obtain its optimal concentration.

EXAMPLE 16

Label-Free Catalytic and Molecular Beacon

This example describes methods for making and using label-free catalytic and molecular beacons that include an abasic site. Such constructs can be used for fluorescent detection of targets and fast evaluation of DNAzyme activity.

Described in the Examples above is the use of abasic and vacant sites containing FNAs for the generation of label-free fluorescent sensors for the detection of a broad range of targets. Using this as a foundation, this example describes label-free catalytic and molecular beacons (CAMBs) FNA sensors using dSpacer-containing molecular beacons (MBs) as DNA substrates. Although specific examples of molecules for detecting metal ions ($Pb^{2+}$) and organic molecules (adenosine) with high selectivity and sensitivity are provided, one skilled in the art will appreciate that based on the teachings herein, one skilled in the art can design label-free CAMBs to detect other agents of interest (such as other heavy metals).

Catalytic beacons have been used as a general platform for the development of sensors for a broad range of metal ions, such as $Pb^{2+}$ (Breaker and Joyce, *Chem. Biol.* 1994, 1, 223; Li and Lu, *J. Am. Chem. Soc.* 2000, 122, 10466), $Mg^{2+}$ (Breaker and Joyce, *Chem. Biol.* 1995, 2, 655), $Zn^{2+}$ (Santoro et al., *J. Am. Chem. Soc.* 2000, 122, 2433.), $Co^{2+}$ (Bruesehoff et al., *Comb. Chem. High Throughput Screening* 2002, 5, 327; Mei, S. H. J.; Liu et al., *J. Am. Chem. Soc.* 2003, 125, 412), $UO_2^{2+}$ (Liu et al., *Proc. Nat. Acad. Sci. U.S.A.* 2007, 104, 2056), and $Cu^{2+}$ (Cuenoud and Szostak, *Nature* 1995, 375, 611; Carmi et al., *Chem. Biol.* 1996, 3, 1039; Liu and Lu, *J. Am. Chem. Soc.* 2007, 129, 9838). The catalytic beacon normally consists of a quencher-labeled DNAzyme (or ribozyme) hybridizing with a fluorophore-labeled substrate of the DNAzyme, thus the DNAzyme has both the roles of quencher and catalyst. Upon the addition of a specific metal ion as the cofactor of the DNAzyme, the cleavage of the substrate catalyzed by the DNAzyme will perturb DNA hybridization and dramatically increase the distance between the quencher and fluorophore, resulting in the enhancement of fluorescence signal. However, to ensure low background fluorescence before the target-induced cleavage of substrate, the quencher-labeled DNAzyme is usually added in excess to minimize the free fluorophore-labeled substrate in solution because the quenching of fluorophore is via the DNA duplex formation between the DNAzyme and its substrate. Therefore, the enzymatic reaction is usually single turnover. Although multiple turnover catalytic reaction of DNAzymes can improve the sensor's sensitivity via signal amplification as protein enzymes or a DNAzyme with peroxidase activity (de Lumley-Woodyear et al. *Anal. Chem.* 1999, 71, 394; Liu et al., *J. Am. Chem. Soc.* 2008, 130, 6820; Li et al. *Chem. Commun.* 2007, 4209; Kolpashchikov, *J. Am. Chem. Soc.* 2008, 130, 2934; Elbaz et al., *Chem. Eur. J.* 2009, 15, 3411; Deng et al., *J. Am. Chem. Soc.* 2008, 130, 13095; Nakayama and Sintim, *J. Am. Chem. Soc.* 2009, 131, 10320), it is extremely challenging for the catalytic beacons, either the first (Li and Lu, *J. Am. Chem. Soc.* 2000, 122:10466) or the second generation (Liu et al., *Proc. Nat. Acad. Sci. U.S.A.* 2007, 104, 2056; Liu and Lu, *J. Am. Chem. Soc.* 2007, 129, 9838; Liu and Lu, *Anal. Chem.* 2003, 75, 6666) to realize such amplification without sacrificing low background fluorescence.

An improved sensor design called catalytic and molecular beacons (CAMBs) (Zhang et al., *Anal. Chem.* 2010, 82, 5005) was developed through the combination of both catalytic beacons (Li and Lu, *J. Am. Chem. Soc.* 2000, 122, 10466; Liu et al., *Proc. Nat. Acad. Sci. U.S.A.* 2007, 104, 2056; Liu and Lu, *J. Am. Chem. Soc.* 2007, 129, 9838; Liu and Lu, *Anal. Chem.* 2003, 75, 6666) and molecular beacons (MBs) (Tan et al., *Curr. Opin. Chem. Biol.* 2004, 8, 547; Wang et al., *Angew. Chem., Int. Ed.* 2009, 48, 856). In this design, the substrate of the DNAzyme was a MB, and the DNAzyme no longer had to take the role of quencher. Therefore, with high quenching efficiency maintained by the substrate itself, the concentration of DNAzyme used could be much lower than that of the substrate, and signal amplification via multiple turnover reactions was achieved in this way. In addition, the CAMB design could also facilitate the development of aptazyme sensors based on catalytic beacons for the sensitive detection of a broader range of targets other than metal ions.

Despite these advantages, CAMB, catalytic beacon and most other fluorescent FNA sensor designs generally require a fluorophore and a quencher labeled at internal, 3' or 5' site of the FNAs to show a fluorescence switch upon the interaction between the sensors and their targets. The covalent labeling is not only expensive and complicated but also reduces the activity of the FNAs (Jiang et al., *Anal. Chem.* 2004, 76:5230; Wang et al., *Anal. Chem.* 2005, 77:3542). Alternatively, label-free approaches that utilize unmodified nucleic acids are more cost-effective and can better reserve the FNAs' activity. Although intercalating dyes have been used as the external fluorophore for label-free fluorescent FNA sensors for the detections of different targets (Joseph et al., *Biospectroscopy* 1996, 2, 173; Li et al., *Chem. Commun.* 2007, 73; Wang and Liu, *Analyst* 2008, 133, 1593), the intercalation of the fluorophore to the FNA duplex is random and the binding site can hardly be controlled, which can hinder rational design of the FNA sensors. Some other techniques, such as the introduction of an additional aptamer that can bind an external fluorophore (Babendure et al., *J. Am. Chem. Soc.* 2003, 125, 14716; Stojanovic and Kolpashchikov, *J. Am. Chem. Soc.* 2004, 126, 9266), have been developed for the controllable binding of fluorophores to FNAs, but the conjugation of the aptamers to FNA sensors makes the rational design difficult. A Spacer C3-based approach has been developed for the label-free detection of organic molecules by fluorescent aptamer sensors (Xu et al., *Chem. Commun.* 2009, 6445; Xu et al., *Chem. Eur. J.* 2009, 15, 10375).

The examples above provide a general methodology for the design of label-free fluorescent FNA sensors for a broad range of targets, such as metal ions and organic molecules, by using either an abasic site (e.g., dSpacer) or a vacant site in the FNAs (Xiang et al., *J. Am. Chem. Soc.* 2009, 131:15352; Xiang et al., *Anal. Chem.* 2010, 82:4122). An external fluorophore binds specifically to the dSpacer or vacant site, and introduction of the abasic site or vacant site to the FNA sensors is straightforward.

Materials and Methods

The fluorophore 2-amino-5,6,7-trimethyl-1,8-naphthyridine (ATMND) was purchased from Ryan Scientific Inc. (Mt. Pleasant, S.C.). Lead acetate and all other chemicals were commercially available analytical grade from Sigma-Aldrich Chemical Co. (St. Louis, Mo.) and were used without further purification. All solutions were prepared in Milli-Q water (resistance>18 MΩ·cm). The oligonucleotides were custom synthesized by Integrated DNA Technology Inc. (Coralville, Iowa) with the sequences as follows:

$Pb^{2+}$-Dependent DNAzymes:

```
                                            (SEQ ID NO: 71)
17E (5 + 5)   5'-TCTTCTCCGAGCCGGTCGAAATAGT-3'

(SEQ ID NO: 72)
17E (5 + 6)   5'-TCTTCTCCGAGCCGGTCGAAATAGTG-3'

(SEQ ID NO: 73)
17E (6 + 6)   5'-CTCTTCTCCGAGCCGGTCGAAATAGTG-3'

(SEQ ID NO: 74)
17E (6 + 7)   5'-CTCTTCTCCGAGCCGGTCGAAATAGTGT-3'

(SEQ ID NO: 75)
17E (7 + 7)   5'-TCTCTTCTCCGAGCCGGTCGAAATAGTGT-3'

(SEQ ID NO: 76)
17E (8 + 8)   5'-ATCTCTTCTCCGAGCCGGTCGAAATAGTGTG-3'
```

Substrate MBs (DNA/RNA Chimers, each With a Single RNA Nucleotide (rA) in the Middle, X represents the dSpacer):

```
MB1
                                            (SEQ ID NO: 77)
3'-GTCCCGTAAAAAAAGTAGAGAAGGrATATCACACAAAAAAAAACGXGAC-5'

MB2
                                            (SEQ ID NO: 78)
3'-CGTCCCGTAAAAAAAGTAGAGAAGGrATATCACACAAAAAAAAACGXGACG-5'
```

Control substrate MB without dSpacer:

```
MB3
                                            (SEQ ID NO: 79)
3'-GTCCCGTAAAAAAAGTAGAGAAGGrATATCACACAAAAAAAAACGGGAC-5'
```

Aptazymes (based on a $Mg^{2+}$-dependent 10-23 DNAzyme and an adenosine aptamer):

```
AAP1 (6 + 6, 3 bp)
                                            (SEQ ID NO: 80)
5'-CTCTTCAGCGATCTAGGGGGAGTATTGCGGAGGATAGCACCCATGTT

AGTGT-3'

AAP2 (7 + 7, 2 bp)
                                            (SEQ ID NO: 81)
5'-TCTCTTCAGCGATCTGGGGGAGTATTGCGGAGGAAGCACCCATGTTA

GTGTG-3'

AAP3 (7 + 7, 3 bp)
                                            (SEQ ID NO: 82)
5'-TCTCTTCAGCGATCTAGGGGGAGTATTGCGGAGGATAGCACCCATGT

TAGTGTG-3'

AAP4 (8 + 8, 2 bp)
                                            (SEQ ID NO: 83)
5'-ATCTCTTCAGCGATCTGGGGGAGTATTGCGGAGGAAGCACCCATGTT

AGTGTGT-3'
```

Mutants of 8-17 DNAzyme:

```
                                            (SEQ ID NO: 84)
M1 5'-CTC TTC TCC GAG CCG GAC GAA TAG TG-3'

(SEQ ID NO: 85)
M2 5'-CTC TTC TGT CAG CGA CAC GAA ATA GTG-3'

(SEQ ID NO: 86)
M3 5'-CTC TTC CCC GAG CCG GTC GAA ATA GTG-3'

(SEQ ID NO: 87)
M4 5'-CTC TTC TCC GAG CCG GTC GAA TAG TG-3'

(SEQ ID NO: 88)
M5 5'-CTC TTC TCC GAG CCG GCG AAA TAG TG-3'

(SEQ ID NO: 89)
M6 5'-CTC TTC TCC GGA GCC CGG TCG AAA TAG TG-3'

(SEQ ID NO: 90)
M7 5'-CTC TTC TCA GAG CCT GTC GAA ATA GTG-3'

(SEQ ID NO: 91)
M8 5'-CTC TTC TCC GAA GCC GGT CGA AAT AGT G-3'

(SEQ ID NO: 92)
M9 5'-CTC TTC TCC GCG ACG GTC GAA ATA GTG-3'
```

Fluorophore labeled substrate DNA for gel electrophoresis:

```
                                            (SEQ ID NO: 93)
FS 5'-/FAM/ACACACTATrAGGAAGAGATG-3'
```

Kinetic fluorescence studies. For a standard measurement of $Pb^{2+}$ using label-free catalytic molecular beacon (CAMB) and 8-17 DNAzyme, 492.5 µL buffer A (25 mM HEPES at pH 7.0 and 200 mM NaCl), 2.5 µL ATMND solution (100 µM), 2.5 µL substrate MB (200 µM), and 2.5 µL 17E (6+6) DNAzyme (200 µM) were added sequentially into a 1.5 mL microcentrifuge tube, after vortexing the tube was allowed to stand at ambient condition for 1 min. The solution was then transferred to a cuvette in a FluoroMax-P fluorimeter (HORIBA Jobin Yvon Inc., Edison, N.J.) and the temperature was controlled at 5° C. for 10 min to allow the temperature to reach equilibrium. After that, 5 μL of $Pb^{2+}$ stock solution of different concentrations was added to the cuvette and followed by vortexing, then time-dependent fluorescent measurement at $\lambda_{ex/em}$=358/405 nm was immediately started. Typically, the rate of fluorescence enhancement ($\Delta F/F_0$ per minute) within 5-8 min after $Pb^{2+}$ addition was calculated for all the measurements. However, when the concentration of $Pb^{2+}$ was at micromolar levels, the cleavage reactions were extremely fast, in such a case, only the initial rates for the first 60 s were calculated.

In a standard adenosine measurement, 492.5 μL buffer B (25 mM HEPES at pH 7.2, 5 mM $MgCl_2$ and 100 mM NaCl), 2.5 μL ATMND solution (100 μM), 2.5 μL substrate MB (200 μM), and 2.5 μL aptazyme AAP2 (200 μM) were added sequentially into a 1.5 mL microcentrifuge tube. After vortexing, the tube was allowed to stand at ambient condition for 1 min. The solution was then transferred to a cuvette in the fluorimeter with a constant temperature control at 5° C. for 10 min to allow the temperature to reach equilibrium. A 5 μL of adenosine stock solution in buffer B was then added to the above mixed solution followed by vortexing and time-dependent fluorescent measurement at $\lambda_{ex/em}$=358/405 nm was immediately initiated. The rate of fluorescence enhancement ($\Delta F/F_0$ per minute) within 5-8 min after the addition of adenosine was calculated for all the measurements.

Label-Free CAMB Sensor for Detecting $Pb^{2+}$ Based on 8-17 DNAzyme

To demonstrate that the disclosed label-free CAMB sensor design can be a general methodology for the development of sensors to detect metal ions, the $Pb^{2+}$-specific 8-17 DNAzyme (Breaker and Joyce, Chem. Biol. 1994, 1, 223) was selected as a model. Lead is a very toxic heavy metal ion to human health and regulated by the U.S. Environmental Protection Agency (EPA) to be less than 15 bbp (72 nM) in drinking water. The sensor design used an abasic site-containing DNAzyme for label-free fluorescent detections (Xiang et al., J. Am. Chem. Soc. 2009, 131:15352) and CAMB sensors (Zhang et al., Anal. Chem. 2010, 82:5005).

As shown in FIG. 24, instead of engineering the 8-17 DNAzyme binding arm with an abasic site, both ends of the substrate strand (top) of the DNAyzme were extended to form a substrate molecular beacon (MB); in this case, the abasic site was within the stem region of the MB, and no chemical modification to either the DNAzyme (bottom) or substrate strand was needed. Through complementary hydrogen bonding toward the opposite nucleobase (cytosine) and π-π stacking effects from the flanking nucleobases (guanines), the external fluorophore ATMND could bind to the abasic site in the hybridized stem region of the MB, resulting in the quenching of its fluorescence. Upon the addition of target metal ion $Pb^{2+}$, the DNAzyme would catalyze the cleavage of the MB substrate, and the MB stem region would dehybridize owing to the significant decrease in its melting temperature, thereby releasing the ATMND into the solution and recovering its quenched fluorescence. Therefore, the concentration of $Pb^{2+}$ can be monitored by the fluorescence enhancement of ATMND.

To demonstrate that the MB stem region could form a stable duplex for the binding of ATMND to the abasic site, the fluorescence spectra of ATMND in the absence and presence of MB1 (SEQ ID NO: 77), which contained a stem of 6 base pairs and a dSpacer, were collected. As shown in FIG. 25, when alone in buffer solution at a concentration of 0.5 μM, ATMND exhibited intensely blue fluorescence emission with a band centered at 405 nm. Upon further addition of MB1, the fluorescence emission of ATMND was quenched by 56%, which was attributed to the binding of ATMND to the abasic site in hybridized MB stem region, because a control strand without any abasic site in the stem could not induce any quenching of the fluorescence (FIG. 26).

To achieve higher quenching efficiency for lower fluorescence background, an extra G-C base pair was added to MB1 (the modified sequence is designated as MB2; SEQ ID NO: 78) to enhance the stability of stem region and facilitate the binding of ATMND to the abasic site. MB2 showed a better quenching efficiency and the fluorescence of ATMND was quenched by more than 85%. MB substrates with even longer stem lengths were not tested because the melting temperature of their stem region (9 bases or more) were calculated to be more than 40° C. in buffer solution with 200 mM NaCl, which were difficult to be dehybridized by the $Pb^{2+}$-induced cleavage reaction under the experimental conditions. Therefore, MB2 was chosen as the substrate molecular beacon design and used in further investigations.

To confirm the presence of $Pb^{2+}$ could result in the cleavage of MB2 and subsequent release of ATMND into solution, 1 μM of $Pb^{2+}$ was added to a buffer solution containing 0.5 μM ATMND, 1 μM 17E (6+6) and 1 μM MB2. A more than 3-fold fluorescence enhancement was observed after 15 min (FIG. 26). These results indicate that the label-free CAMB sensor design did not perturb the original activity of the 8-17 DNAzyme, which is crucial for the fluorescence enhancement.

To optimize the sensing performance, the effect of the arm length of 8-17 DNAzyme strand was also investigated. Reducing the arm length on each side of the cleavage site (3' of rA) from 8 to 6 bases resulted in a faster increase of fluorescence signal, indicating that the shorter arm length could facilitate the dehybridization of the substrate MB2 stem after cleavage. However, if the arm length was shorter than 6 bases at either side, it would weaken the hybridization between the substrate and DNAzyme, and hence, reduce the efficiency of the DNAzyme-catalyzed reaction (FIG. 27). Therefore, the optimal arm length of DNAzyme was determined to be 6 bases on each side of the cleavage site (called 17E (6+6); SEQ ID NO: 73).

In addition, the rate of fluorescence enhancement increased when the salt (NaCl) concentration increased from 100 to 200 mM, but decreased when increased to 300 mM (FIG. 28). Based on the above results, the 17E (6+6) DNAzyme with 6 bases on each arm in a buffer solution containing 200 mM NaCl was selected for further $Pb^{2+}$ sensing experiments.

Under the optimized conditions, kinetics studies were performed to monitor the time-dependent fluorescence response of ATMND at 405 nm after the reaction was initiated by the addition of different concentrations of $Pb^{2+}$ (FIG. 29A). Instead of using the data of fluorescence intensity at a certain time point, the rate of fluorescence enhancement ($\Delta F/F_0$ per minute) within 5-8 min after the addition of $Pb^{2+}$ was recorded, because the rate measurement showed better resistance to fluctuations in the background fluorescence of the samples.

As shown in FIG. 29B, the rate of fluorescence enhancement ($\Delta F/F_0$ per minute) showed an approximately linear relationship with $Pb^{2+}$ concentration ($C_{Pb^{2+}}$) in the range of 0-2 μM as $\Delta F/F_0$ ($min^{-1}$)=0.146×$C_{Pb}^{2+}$ (μM). The label-free CAMB sensor was very sensitive to $Pb^{2+}$ with a detection limit measured by $3\sigma_b$/slope ($\sigma_b$, standard deviation of the blank samples) to be 3.8 nM, which is comparable or even lower than some previously reported labeled and label-free fluorescent methods (Li and Lu, J. Am. Chem. Soc. 2000, 122:10466; Liu and Lu, Anal. Chem. 2003, 75:6666; Brown et al., Biochemistry 2003, 42:7152; Kim et al., Nat. Chem.

Biol. 2007, 3:763; Liu and Lu, Methods Mol. Biol. 2006, 335:275), and considerably lower than the EPA-defined maximal contamination level of $Pb^{2+}$ in drinking water. In addition, this method maintained an excellent selectivity for $Pb^{2+}$ over other divalent metal ions, such as $Mg^{2+}$, $Ca^{2+}$, $Sr^{2+}$, $Ba^{2+}$, $Mn^{2+}$, $Fe^{2+}$, $Co^{2+}$, $Zn^{2+}$, $Ni^{2+}$, $Hg^{2+}$ and $Cd^{2+}$ (FIG. 30).

Label-Free CAMB Sensor for Detecting Adenosine Based on an Adenosine Aptazyme

Benefits of the disclosed label-free CAMB sensor over the reported label-free fluorescent methods based on Spacer C3, dSpacer or vacant site (Xu et al., *Chem. Commun.* 2009, 6445; Xu et al., *Chem. Eur. J.* 2009, 15:10375; Xiang et al., *J. Am. Chem. Soc.* 2009, 131:15352; Xiang et al., *Anal. Chem.* 2010, 82:4122) include the possibility of multiple turnover reactions for signal amplification, and the ease for rational design of aptazyme (Breaker, *Curr. Opin. Biotechnol.* 2002, 13:31) sensors for a broader range of targets. The previously reported label-free methods based on Spacer C3, dSpacer or vacant site generally required more amount of DNAzyme than its substrates to minimize the amount of un-hybridized substrate in solution, because the presence of un-hybridized substrate strand could inhibit the fluorescence enhancement induced by the target-induced catalytic reactions and lower the sensitivity of the sensor or cause false negative results. In this case, when the DNAzyme sensor is directly transformed into an aptazyme one, the excess aptazymes in solution can bind targets but have no hybridized substrates to cleave for the production of fluorescence change, resulting in lower sensitivity and even false negative results. However, in the label-free CAMB sensor design, the DNAzyme strand does not need to be added in excess to ensure the efficient DNA hybridization with its substrate, because the presence of un-hybridized substrate does not affect the signal enhancement by the target.

The label-free CAMB system was applied to aptazyme sensors for the detection of broader range of targets, such as organic molecules. FIG. 31 depicts the strategy for the label-free fluorescence detection of adenosine using an allosteric DNAzyme (aptazyme; Elbaz et al., *Chem. Eur. J.* 2009, 15, 3411) based on a $Mg^{2+}$-dependent 10-23 DNAzyme (Breaker and Joyce, *Chem. Biol.* 1995, 2, 655) and an adenosine aptamer (Nutiu and Li, *J. Am. Chem. Soc.* 2003, 125:4771) because the hairpin structure in its catalytic core can be modified with its catalytic activity reserved. As the case of the label-free CAMB $Pb^{2+}$ sensor described above, the fluorophore ATMND can bind to the abasic site in the hybridized MB stem region of the substrate, which leads to its fluorescence quenching. After the addition of the apatazyme strand, the formation of the substrate-aptazyme duplex could not induce the cleavage of the substrate and the subsequent release of ATMND from the stem region unless the target adenosine was present in the $Mg^{2+}$-containing buffer. In the presence of adenosine, a fluorescence enhancement signal was generated through releasing of ATMND into the buffer.

To optimize the sensing performance, the effect of the arm length of apatazyme strand was also investigated. AAP1, 2, 3 and 4 were tested. As shown in FIG. 32, the optimal arm length of apatazyme was determined to be 7 bases on each side of the cleavage site (called AAP2 (7+7); SEQ ID NO: 81).

In a solution containing 0.5 µM ATMND, 1 µM AAP2 (SEQ ID NO: 81) and 1 µM MB2 (SEQ ID NO: 78), upon the addition of 5 mM $Mg^{2+}$, little fluorescence enhancement was observed, indicating that the aptazyme was inactive without adenosine as the target. In the presence of adenosine, fluorescence enhancement was observed, indication that the aptazyme was activated by adenosine and led to the release of ATMND from MB stem duplex into solution by the catalytic cleavage of the substrate (FIG. 31).

As shown in FIG. 33, the rate of fluorescence enhancement ratio ($\Delta F/F_0$ per minute) increased with increasing the concentration of adenosine and reached a plateau at ~500 µM. A detection limit ($3\sigma_b$/slope, $\sigma_b$, standard deviation of the blank samples) as low as 1.4 µM was obtained, which was comparable or even lower than most reported fluorescent sensors for adenosine without signal amplification or the previous label-free methods using a Spacer C3, dSpacer, or vacant site (Xu et al., *Chem. Commun.* 2009, 6445; Xu et al., *Chem. Eur. J.* 2009, 15:10375; Xiang et al., *J. Am. Chem. Soc.* 2009, 131: 15352; Xiang et al., *Anal. Chem.* 2010, 82:4122), because the activated aptazyme could catalyze multiple turnover cleavage of the substrate MBs for signal amplification and the rate measurement in this work was much less vulnerable to fluctuations in the background fluorescence than the intensity measurement used in the reported works.

The selectivity toward adenosine over other nucleotides such as uridine and cytidine was determined. As shown in FIG. 34, little fluorescence enhancement of the label-free CAMB sensor was observed for these control compounds even in concentrations up to 500 µM, indicating that the sensor was very selective to adenosine. Guanosine was not tested for its low solubility in aqueous solutions.

EXAMPLE 17

Evaluation of DNAzyme Activity by Label-Free CAMB Sensors

This example describes methods of using the label-free substrate MBs described above in Example 16 to evaluate the activity of a DNAzyme. Because no labeling or modification to the FNA (e.g., DNAzyme) is needed, the sensors can also be used to evaluate the activity of DNAzymes under both single and multiple turnover conditions. Compared to traditional PAGE methods for DNAzyme activity, this method is simpler, faster, real-time, and can achieve single and multiple turnover activity evaluation. Thus, the disclosed method provided is fast, low-cost, applicable to both single and multiple turnover assays, and provides real-time for monitoring the enzymatic cleavage reactions.

PAGE gel methods that are traditionally used for determining the activity of DNAzymes are complicated and time consuming (Breaker and; Joyce, *Chem. Biol.* 1994, 1:223; Breaker and Joyce, *Chem. Biol.* 1995, 2:655). For faster assays, the activity can also be monitored by fluorescent sensors such as catalytic beacons (Li and Lu, *J. Am. Chem. Soc.* 2000, 122, 10466; Liu, J.; Brown et al., *Proc. Nat. Acad. Sci. U.S.A.* 2007, 104, 2056; Liu and Lu, *J. Am. Chem. Soc.* 2007, 129, 9838; Liu and Lu, *Anal. Chem.* 2003, 75, 6666) or abasic site containing label-free sensors (Xu et al., *Chem. Commun.* 2009, 6445; Xu et al., *Chem. Eur. J.* 2009, 15:10375; Xiang, et al., *J. Am. Chem. Soc.* 2009, 131:15352.). However, these methods need either labeled DNAzyme that is costly or excess DNAzymes over substrate that can only do single turn over assays. Since the DNAzymes used for the label-free CAMB sensors described herein do not need to be modified and their concentrations are independent on those of the substrate MBs, the sensor design can be used for fast evaluation of the DNAzymes' activities under both single and multiple turnover conditions.

To demonstrate this application, the activities of 8-17 DNAzyme (Breaker and; Joyce, *Chem. Biol.* 1994, 1:223) and its 9 mutants (M1-M9; Brown et al., *Biochemistry* 2003, 42:7152; SEQ ID NOS: 84-92) were evaluated under single turnover and multiple turnover conditions using our label-free CAMB system. For fast evaluation of DNAzyme activity of 8-17 DNAzyme and its 9 mutants (M1~M9) by the label-free CAMB sensor, the rate of fluorescence enhancement ($\Delta F/F_0$ per minute) of 0.5 µM ATMND, 1 µM substrate MB2 and 2 µM DNAzyme for single turnover reaction; or 0.5 µM ATMND, 1 µM substrate MB and 0.2 µM DNAzyme for multiple turnover reaction, were tested in the presence of 100 µM $Pb^{2+}$ in buffer A under the same procedures described in Example 16.

As displayed in Table 2 (and FIG. 35), the fluorescence enhancement rates of the DNAzymes followed the order of 8-17, M2 with high activity>M7, M4, M1, M3 with medium activity>M6, M8, M5, M9 with low activity, according to the results of fluorescent kinetic curves. This order of activity is in agreement with previous mutation studies on the DNAzyme (Brown et al., *Biochemistry* 2003, 42:7152).

TABLE 2

Cleavage rates for the 8-17 DNAzyme and its mutants
in the presence of 100 µM $Pb^{2+}$ (pH 7.0)

| 8-17 mutants | Cleavage rate ($min^{-1}$) [a] | | Cleavage rate ($min^{-1}$) [b] | |
|---|---|---|---|---|
| | Single-turnover [c] | Multiple-turnover [d] | Single-turnover | Multiple-turnover |
| 8-17 | 1.13 | 0.094 | 2.39 | 0.63 |
| M1 | 0.022 | $2.0 \times 10^{-3}$ | 0.13 | 0.013 |
| M2 | 1.02 | 0.117 | 3.59 | 0.68 |
| M3 | 0.014 | $3.1 \times 10^{-3}$ | 0.024 | 0.016 |
| M4 | 0.066 | 0.010 | 0.56 | 0.13 |
| M5 | $1.4 \times 10^{-3}$ | $1.2 \times 10^{-4}$ | 0.011 | —[e] |
| M6 | $1.7 \times 10^{-3}$ | — | — | — |
| M7 | 0.095 | 0.014 | 0.182 | 0.026 |
| M8 | $1.6 \times 10^{-3}$ | $4.8 \times 10^{-4}$ | 0.016 | 0.007 |
| M9 | — | — | — | 0.006 |

[a] Measured by label-free CAMB based fluorescence method;
[b] measured by conventional PAGE assay;
[c] in the condition of 2 µM DNAzyme and 1 µM MB2;
[d] in the condition of 0.2 µM DNAzyme and 1 µM MB2;
[e] the symbol "—" indicated that the cleavage rate was less than $1.0 \times 10^{-4}$ ($min^{-1}$) under the detection conditions.

To further ensure that the method was reliable, conventional enzymatic activity assay was determined using fluorescence PAGE under the same conditions. Briefly, a mixture solution (200 µL) in buffer A containing 1 µM fluorophore labeled substrate DNA FS, 2 µM or 0.2 µM DNAzyme was incubated at 5° C. for 15 min in order to allow the temperature to reach equilibrium. After incubation, 20 µL of the solution was taken out and added to a tube with 2 µL of 100 mM EDTA as stop solution. This was a control sample to indicate the extent of cleavage before the reaction was initiated by $Pb^{2+}$. Then 1.8 µL of $Pb^{2+}$ stock solution (10 mM) was added into the mixed DNAzyme/substrate solution to initiate the reaction. At various predetermined time-points, a 20 µL aliquot of the reaction mixture was added to 2 µL of stop solution in each tube. The cleaved and uncleaved substrates were separated by 15% denaturing polyacrylamide gel electrophoresis, and then analyzed by a fluorescence image scanner (FLA-3000G; Fuji, Tokyo, Japan) using 473 nm as excitation. The percent cleavage at a certain time was calculated by dividing the amount of cleavage product by the total amount of substrate plus product, after deduction of background fluorescence in the gel. The rate constants were afforded by fitting the equation $y=y_0+Ae^{-x/t}$ (Brown et al., *Biochemistry* 2003, 42, 7152).

As shown in FIGS. 36A and B, the order of the cleavage rates was well in accordance with the one obtained by the assays based on the disclosed label-free CAMB sensors. In addition, it was reported that in the presence of high concentration of $Pb^{2+}$, the cleavage rates of 8-17 and M2 were too fast for accurate determination using the conventional PAGE assay (Liu and Lu, *Methods Mol. Biol.* 2006, 335:275), but the disclosed method can measure them because the fluorescence monitoring is real-time.

In summary, the label-free CAMB-based method can be used for fast evaluation of DNAzyme activity. It is low cost, can be used for both single and multiple turnover assays, and for real-time monitoring of the enzymatic cleavage reaction. Compared to conventional of DNAzyme activity assays based on PAGE gels assays and those based on other fluorescent sensors, the label-free CAMB-based method is simpler, faster, and capable of real-time monitoring.

In summary, label-free fluorescent catalytic and molecular beacon (CAMB) sensors can detect metal ions and organic molecules. The sensor design has both the advantages of the label-free sensors that are low-cost and well preserve the activity of the functional nucleic acids (FNAs) and that of the CAMB sensors which exhibit signal amplification via multiple turnover reactions and ease for the rational design of aptazymes. By using the 8-17 DNAzyme and the aptazyme of adenosine based on 10-23 DNAzyme as examples, the disclosed sensors can be used to detect $Pb^{2+}$ and adenosine with high selectivity and sensitivity (detection limits of 3.8 nM and 1.4 µM, respectively).

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

We claim:

1. A sensor, comprising
a catalytic nucleic acid molecule specific for a target agent comprising an enzyme nucleic acid strand and a substrate nucleic acid strand,
wherein the enzyme nucleic acid strand comprises a 3'-end and a 5'-end and an active site specific for a target agent,
wherein the substrate nucleic acid strand comprises a 3'-end and a 5'-end,
wherein the substrate nucleic acid strand comprises nucleotides at the 5'-end of the substrate nucleic acid strand that permits formation of a loop of at least six nucleotides at the 5'-end of the substrate nucleic acid strand, and
wherein the substrate nucleic acid strand hybridizes with the enzyme nucleic acid strand, thereby forming a vacant site between the 3'-end of the enzyme nucleic acid strand and the 5'-end of the substrate nucleic acid strand, wherein the vacant site is opposite to a cytosine present in the substrate nucleic acid strand and wherein the vacant site can bind to a fluorophore,
wherein in the absence of the target agent, fluorescence of the fluorophore when bound to the vacant site is quenched, and wherein in the presence of the target agent, catalytic cleavage of substrate nucleic acid strand perturbs the vacant site and releases the fluorophore bound to the vacant site resulting in increased fluorescence.

2. The sensor of claim 1, wherein the vacant site is flanked by guanines present on a 3'-nucleotide of the enzyme nucleic acid strand and a 5'-nucleotide of the substrate nucleic acid strand.

3. The sensor of claim 1, wherein at least one pair of nucleotides are mismatched upon hybridization of the substrate nucleic acid molecule with the enzyme nucleic acid strand.

4. The sensor of claim 1, wherein the catalytic nucleic acid comprises a DNAzyme or an aptazyme.

5. The sensor of claim 1, wherein the sensor is attached to a solid support.

6. A kit comprising:
the sensor of claim 1; and
one or more of a buffer, a chart for correlating detected fluorescence and amount of target agent present, or a test agent.

7. A method for detecting a target agent, comprising
contacting the sensor of claim 1 with a sample under conditions sufficient to allow the target agent in the sample to bind to the sensor resulting in cleavage of the sensor or a conformational change of the sensor; and
detecting fluorescence, wherein detection of fluorescence indicates the presence of the target agent in the sample, and an absence of detected fluorescence indicates the absence of the target agent in the sample.

8. The method of claim 7, further comprising quantifying the target agent, wherein a level of fluorescence detected indicates an amount of target agent present.

9. The sensor of claim 1, wherein the catalytic nucleic acid comprises a DNAzyme.

10. The sensor of claim 1, wherein the catalytic nucleic acid comprises an RNAzyme.

11. The sensor of claim 1, wherein the loop is formed by at least 15 nucleotides between the vacant site and the cytosine opposite to the vacant site.

12. The sensor of claim 1, wherein the target agent is a metal.

13. The sensor of claim 1, wherein the target agent is a heavy metal.

14. The sensor of claim 1, wherein the target agent is mercury, cadmium, arsenic, chromium, thallium, magnesium, copper, lead or uranium.

15. The sensor of claim 1, wherein the target agent is lead or uranium.

16. The sensor of claim 1, wherein the target agent is a pathogen, protein, recreational drug, or cell.

17. The sensor of claim 1, wherein the fluorophore is quenched in the presence of cytosine.

18. The sensor of claim 1, wherein the fluorophore is 2-amino-5,6,7-trimethyl-1,8-naphthyridine (ATMND).

19. The sensor of claim 1, wherein the fluorophore is 3,5-diamino-6-chloro-2-pyrazine carbonitrile (DCPC), fluorescein, rhodamine, malachite green (MG) or an Alexa Fluor fluorophore.

* * * * *

SEQUENCE LISTING

<160> NUMBER OF SEQ ID NOS: 97

<210> SEQ ID NO 1
<211> LENGTH: 35
<212> TYPE: DNA
<213> ORGANISM: Artificial sequence
<220> FEATURE:
<223> OTHER INFORMATION: Synthetic oligonucleotide sensor

<400> SEQUENCE: 1
acagacatct cttctccgag ccggtcgaaa tagtg                              35

```
<210> SEQ ID NO 2
<211> LENGTH: 40
<212> TYPE: DNA
<213> ORGANISM: Artificial sequence
<220> FEATURE:
<223> OTHER INFORMATION: Synthetic oligonucleotide sensor
<220> FEATURE:
<221> NAME/KEY: misc_feature
<222> LOCATION: (25)..(25)
<223> OTHER INFORMATION: n is an adenine ribonucleotide (rA)

<400> SEQUENCE: 2
gacgatgaaa catcgtccca ctatnggaag agatgtctgt                              40

<210> SEQ ID NO 3
<211> LENGTH: 41
<212> TYPE: DNA
<213> ORGANISM: Artificial sequence
<220> FEATURE:
<223> OTHER INFORMATION: Synthetic oligonucleotide sensor
<220> FEATURE:
<221> NAME/KEY: misc_feature
<222> LOCATION: (26)..(26)
<223> OTHER INFORMATION: n is an adenine ribonucleotide (rA)

<400> SEQUENCE: 3
ggacgatgaa acatcgtccc actatnggaa gagatgtctg t                            41

<210> SEQ ID NO 4
<211> LENGTH: 35
<212> TYPE: DNA
<213> ORGANISM: Artificial sequence
<220> FEATURE:
<223> OTHER INFORMATION: Synthetic oligonucleotide sensor

<400> SEQUENCE: 4
acagacatct cttccccgag ccggtcgaaa tagtg                                   35

<210> SEQ ID NO 5
<211> LENGTH: 44
<212> TYPE: DNA
<213> ORGANISM: Artificial sequence
<220> FEATURE:
<223> OTHER INFORMATION: Synthetic oligonucleotide aptamer

<400> SEQUENCE: 5
gatcacaaag tgatcccacc tgggggagta ttgcggagga aggt                         44

<210> SEQ ID NO 6
<211> LENGTH: 44
<212> TYPE: DNA
<213> ORGANISM: Artificial sequence
<220> FEATURE:
<223> OTHER INFORMATION: Synthetic oligonucleotide inactive aptamer

<400> SEQUENCE: 6
gatcacaaag tgatcccacc tggggtgta ttgcggagga aggt                          44

<210> SEQ ID NO 7
<211> LENGTH: 44
<212> TYPE: DNA
<213> ORGANISM: Artificial sequence
<220> FEATURE:
<223> OTHER INFORMATION: Synthetic oligonucleotide inactive aptamer

<400> SEQUENCE: 7
gatcacaaag tgatcccacc tgggggagta ttgcggaggt aggt                         44
```

```
<210> SEQ ID NO 8
<211> LENGTH: 7
<212> TYPE: DNA
<213> ORGANISM: Artificial sequence
<220> FEATURE:
<223> OTHER INFORMATION: Synthetic oligonucleotide that binds an
      adenosine aptamer

<400> SEQUENCE: 8 ccaggtg                                                                    7

<210> SEQ ID NO 9
<211> LENGTH: 8
<212> TYPE: DNA
<213> ORGANISM: Artificial sequence
<220> FEATURE:
<223> OTHER INFORMATION: Synthetic oligonucleotide that binds an
      adenosine aptamer

<400> SEQUENCE: 9 cccaggtg                                                                   8

<210> SEQ ID NO 10
<211> LENGTH: 9
<212> TYPE: DNA
<213> ORGANISM: Artificial sequence
<220> FEATURE:
<223> OTHER INFORMATION: Synthetic oligonucleotide that binds an
      adenosine aptamer

<400> SEQUENCE: 10 ccccaggtg                                                                  9

<210> SEQ ID NO 11
<211> LENGTH: 9
<212> TYPE: DNA
<213> ORGANISM: Artificial sequence
<220> FEATURE:
<223> OTHER INFORMATION: Synthetic oligonucleotide that binds an
      adenosine aptamer

<400> SEQUENCE: 11 cccaggtgg                                                                  9

<210> SEQ ID NO 12
<211> LENGTH: 49
<212> TYPE: DNA
<213> ORGANISM: Artificial sequence
<220> FEATURE:
<223> OTHER INFORMATION: Synthetic oligonucleotide sensor

<400> SEQUENCE: 12
cacgtccatc tctgcagtcg ggtagttaaa ccgaccttca gacatagtg                     49

<210> SEQ ID NO 13
<211> LENGTH: 41
<212> TYPE: DNA
<213> ORGANISM: Artificial sequence
<220> FEATURE:
<223> OTHER INFORMATION: Synthetic oligonucleotide sensor
<220> FEATURE:
<221> NAME/KEY: misc_feature
<222> LOCATION: (25)..(25)
<223> OTHER INFORMATION: n is an adenine ribonucleotide (rA)

<400> SEQUENCE: 13
gacgatgaaa catcgtccca ctatnggaag agatggacgt g                             41
```

<210> SEQ ID NO 14
<211> LENGTH: 50
<212> TYPE: DNA
<213> ORGANISM: Artificial sequence
<220> FEATURE:
<223> OTHER INFORMATION: Synthetic oligonucleotide aptamer

<400> SEQUENCE: 14
gacgatgaaa catcgtccct gtttgtttgt tggccccct tctttcttac          50

<210> SEQ ID NO 15
<211> LENGTH: 7
<212> TYPE: DNA
<213> ORGANISM: Artificial sequence
<220> FEATURE:
<223> OTHER INFORMATION: Synthetic oligonucleotide that binds an aptamer

<400> SEQUENCE: 15 caaacag          7

<210> SEQ ID NO 16
<211> LENGTH: 37
<212> TYPE: DNA
<213> ORGANISM: Artificial sequence
<220> FEATURE:
<223> OTHER INFORMATION: Synthetic oligonucleotide sensor
<220> FEATURE:
<221> NAME/KEY: misc_feature
<222> LOCATION: (34)..(34)
<223> OTHER INFORMATION: n is an abasic site

<400> SEQUENCE: 16
acagacatct cttctccgag ccggtcgaaa tagngag          37

<210> SEQ ID NO 17
<211> LENGTH: 37
<212> TYPE: DNA
<213> ORGANISM: Artificial sequence
<220> FEATURE:
<223> OTHER INFORMATION: Synthetic oligonucleotide for an inacive
      DNAzyme

<400> SEQUENCE: 17
acagacatct cttctccgag ccggtcgaaa tagggag          37

<210> SEQ ID NO 18
<211> LENGTH: 24
<212> TYPE: DNA
<213> ORGANISM: Artificial sequence
<220> FEATURE:
<223> OTHER INFORMATION: Synthetic oligonucleotide sensor
<220> FEATURE:
<221> NAME/KEY: misc_feature
<222> LOCATION: (9)..(9)
<223> OTHER INFORMATION: n is an adenine ribonucleotide (rA)

<400> SEQUENCE: 18
ctccctatag gaagagatgt ctgt          24

<210> SEQ ID NO 19
<211> LENGTH: 35
<212> TYPE: DNA
<213> ORGANISM: Artificial sequence
<220> FEATURE:
<223> OTHER INFORMATION: Synthetic oligonucleotide aptamer

<400> SEQUENCE: 19
tgtcgttgac ctgggggagt attgcggagg aaggt                                    35

<210> SEQ ID NO 20
<211> LENGTH: 12
<212> TYPE: DNA
<213> ORGANISM: Artificial sequence
<220> FEATURE:
<223> OTHER INFORMATION: Synthetic oligonucleotide that binds an
      adenosine aptamer
<220> FEATURE:
<221> NAME/KEY: misc_feature
<222> LOCATION: (4)..(4)
<223> OTHER INFORMATION: n is an abasic site

<400> SEQUENCE: 20
ccangtcaac ga                                                             12

<210> SEQ ID NO 21
<211> LENGTH: 13
<212> TYPE: DNA
<213> ORGANISM: Artificial sequence
<220> FEATURE:
<223> OTHER INFORMATION: Synthetic oligonucleotide that binds an
      adenosine aptamer
<220> FEATURE:
<221> NAME/KEY: misc_feature
<222> LOCATION: (5)..(5)
<223> OTHER INFORMATION: n is an abasic site

<400> SEQUENCE: 21
cccangtcaa cga                                                            13

<210> SEQ ID NO 22
<211> LENGTH: 14
<212> TYPE: DNA
<213> ORGANISM: Artificial sequence
<220> FEATURE:
<223> OTHER INFORMATION: Synthetic oligonucleotide that binds an
      adenosine aptamer
<220> FEATURE:
<221> NAME/KEY: misc_feature
<222> LOCATION: (6)..(6)
<223> OTHER INFORMATION: n is an abasic site

<400> SEQUENCE: 22
ccccangtca acga                                                           14

<210> SEQ ID NO 23
<211> LENGTH: 16
<212> TYPE: DNA
<213> ORGANISM: Artificial sequence
<220> FEATURE:
<223> OTHER INFORMATION: Synthetic oligonucleotide that binds an
      adenosine aptamer
<220> FEATURE:
<221> NAME/KEY: misc_feature
<222> LOCATION: (6)..(6)
<223> OTHER INFORMATION: n is an abasic site

<400> SEQUENCE: 23
ccccangtca acgaca                                                         16

<210> SEQ ID NO 24
<211> LENGTH: 13
<212> TYPE: DNA
<213> ORGANISM: Artificial sequence
<220> FEATURE:
<223> OTHER INFORMATION: Synthetic oligonucleotide that binds an
      adenosine aptamer

```
<400> SEQUENCE: 24
cccaggtcaa cga                                                             13

<210> SEQ ID NO 25
<211> LENGTH: 35
<212> TYPE: DNA
<213> ORGANISM: Artificial sequence
<220> FEATURE:
<223> OTHER INFORMATION: Synthetic oligonucleotide aptamer

<400> SEQUENCE: 25
tgtcgttgac ctgggggagt attgcggagg gaggt                                     35

<210> SEQ ID NO 26
<211> LENGTH: 27
<212> TYPE: DNA
<213> ORGANISM: Artificial sequence
<220> FEATURE:
<223> OTHER INFORMATION: Synthetic oligonucleotide aptamer

<400> SEQUENCE: 26
acctggggga gtattgcgga ggaaggt                                              27

<210> SEQ ID NO 27
<211> LENGTH: 27
<212> TYPE: RNA
<213> ORGANISM: Artificial sequence
<220> FEATURE:
<223> OTHER INFORMATION: Synthetic oligonucleotide aptamer

<400> SEQUENCE: 27
ucccgacugg aacagguaac gaaugga                                              27

<210> SEQ ID NO 28
<211> LENGTH: 11
<212> TYPE: DNA
<213> ORGANISM: Artificial sequence
<220> FEATURE:
<223> OTHER INFORMATION: Synthetic oligonucleotide bridging strands that
      bind an aptamer

<400> SEQUENCE: 28
caggttccat t                                                               11

<210> SEQ ID NO 29
<211> LENGTH: 11
<212> TYPE: DNA
<213> ORGANISM: Artificial sequence
<220> FEATURE:
<223> OTHER INFORMATION: Synthetic oligonucleotide bridging strands that
      bind an aptamer

<400> SEQUENCE: 29
ccaggttcca t                                                               11

<210> SEQ ID NO 30
<211> LENGTH: 12
<212> TYPE: DNA
<213> ORGANISM: Artificial sequence
<220> FEATURE:
<223> OTHER INFORMATION: Synthetic oligonucleotide bridging strands that
      bind an aptamer

<400> SEQUENCE: 30
ccaggttcca tt                                                              12
```

<210> SEQ ID NO 31
<211> LENGTH: 13
<212> TYPE: DNA
<213> ORGANISM: Artificial sequence
<220> FEATURE:
<223> OTHER INFORMATION: Synthetic oligonucleotide bridging strands that
      bind an aptamer

<400> SEQUENCE: 31
ccaggttcca ttc                                                          13

<210> SEQ ID NO 32
<211> LENGTH: 14
<212> TYPE: DNA
<213> ORGANISM: Artificial sequence
<220> FEATURE:
<223> OTHER INFORMATION: Synthetic oligonucleotide bridging strands that
      bind an aptamer

<400> SEQUENCE: 32
ccaggttcca ttcg                                                         14

<210> SEQ ID NO 33
<211> LENGTH: 15
<212> TYPE: DNA
<213> ORGANISM: Artificial sequence
<220> FEATURE:
<223> OTHER INFORMATION: Synthetic oligonucleotide bridging strands that
      bind an aptamer

<400> SEQUENCE: 33
ccaggttcca ttcgt                                                        15

<210> SEQ ID NO 34
<211> LENGTH: 16
<212> TYPE: DNA
<213> ORGANISM: Artificial sequence
<220> FEATURE:
<223> OTHER INFORMATION: Synthetic oligonucleotide bridging strands that
      bind an aptamer

<400> SEQUENCE: 34
ccaggttcca ttcgtt                                                       16

<210> SEQ ID NO 35
<211> LENGTH: 17
<212> TYPE: DNA
<213> ORGANISM: Artificial sequence
<220> FEATURE:
<223> OTHER INFORMATION: Synthetic oligonucleotide that binds a
      theophylline aptamer
<220> FEATURE:
<221> NAME/KEY: misc_feature
<222> LOCATION: (13)..(13)
<223> OTHER INFORMATION: n is an abasic site

<400> SEQUENCE: 35
attcgcccat agngtga                                                      17

<210> SEQ ID NO 36
<211> LENGTH: 36
<212> TYPE: DNA
<213> ORGANISM: Artificial sequence
<220> FEATURE:
<223> OTHER INFORMATION: Synthetic oligonucleotide for an inactive lead
      DNAzyme

```
<400> SEQUENCE: 36
acagacatct cttctccgag ccggtcgaaa taggga                               36

<210> SEQ ID NO 37
<211> LENGTH: 37
<212> TYPE: DNA
<213> ORGANISM: Artificial sequence
<220> FEATURE:
<223> OTHER INFORMATION: Synthetic oligonucleotide for an inactive lead
      DNAzyme
<220> FEATURE:
<221> NAME/KEY: misc_feature
<222> LOCATION: (34)..(34)
<223> OTHER INFORMATION: n is an abasic site

<400> SEQUENCE: 37
acagacatct cttccccgag ccggtcgaaa tagngag                              37

<210> SEQ ID NO 38
<211> LENGTH: 37
<212> TYPE: DNA
<213> ORGANISM: Artificial sequence
<220> FEATURE:
<223> OTHER INFORMATION: Synthetic oligonucleotide for an inactive lead
      DNAzyme
<220> FEATURE:
<221> NAME/KEY: misc_feature
<222> LOCATION: (34)..(34)
<223> OTHER INFORMATION: n is an abasic site

<400> SEQUENCE: 38
acagacatct cttccccgag ccggtcgaaa tagngag                              37

<210> SEQ ID NO 39
<211> LENGTH: 35
<212> TYPE: DNA
<213> ORGANISM: Artificial sequence
<220> FEATURE:
<223> OTHER INFORMATION: Synthetic oligonucleotide aptamer

<400> SEQUENCE: 39
tgtcgttgac ctgggggcgt attgcggagg aaggt                                35

<210> SEQ ID NO 40
<211> LENGTH: 35
<212> TYPE: DNA
<213> ORGANISM: Artificial sequence
<220> FEATURE:
<223> OTHER INFORMATION: Synthetic oligonucleotide aptamer

<400> SEQUENCE: 40
tgtcgttgac ctgggggagt attgcggagg caggt                                35

<210> SEQ ID NO 41
<211> LENGTH: 35
<212> TYPE: DNA
<213> ORGANISM: Artificial sequence
<220> FEATURE:
<223> OTHER INFORMATION: Synthetic oligonucleotide aptamer

<400> SEQUENCE: 41
tgtcgttgac ctgggggagt attgcggagg taggt                                35

<210> SEQ ID NO 42
<211> LENGTH: 35
<212> TYPE: DNA
<213> ORGANISM: Artificial sequence
```

```
<220> FEATURE:
<223> OTHER INFORMATION: Synthetic oligonucleotide aptamer

<400> SEQUENCE: 42
tgtcgttgac ctgggggtgt attgcggagg aaggt                          35

<210> SEQ ID NO 43
<211> LENGTH: 35
<212> TYPE: DNA
<213> ORGANISM: Artificial sequence
<220> FEATURE:
<223> OTHER INFORMATION: Synthetic oligonucleotide sensor
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (33)..(35)
<223> OTHER INFORMATION: n is a, c, g, or t

<400> SEQUENCE: 43
nnnnnnnnnn nntctccgag ccggtcgaaa tannn                          35

<210> SEQ ID NO 44
<211> LENGTH: 40
<212> TYPE: DNA
<213> ORGANISM: Artificial sequence
<220> FEATURE:
<223> OTHER INFORMATION: Synthetic oligonucleotide aptamer
<220> FEATURE:
<221> NAME/KEY: misc_feature
<222> LOCATION: (1)..(17)
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t
<220> FEATURE:
<221> NAME/KEY: misc_feature
<222> LOCATION: (25)..(25)
<223> OTHER INFORMATION: n is an adenine ribonucleotide (rA)
<220> FEATURE:
<221> NAME/KEY: misc_feature
<222> LOCATION: (29)..(40)
<223> OTHER INFORMATION: n is a, c, g, or t

<400> SEQUENCE: 44
nnnnnnnnnn nnnnnnncnn ntatnggann nnnnnnnnnn                     40

<210> SEQ ID NO 45
<211> LENGTH: 49
<212> TYPE: DNA
<213> ORGANISM: Artificial sequence
<220> FEATURE:
<223> OTHER INFORMATION: Synthetic oligonucleotide aptamer
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (47)..(49)
<223> OTHER INFORMATION: n is a, c, g, or t

<400> SEQUENCE: 45
nnnnnnnnnn nntgcagtcg ggtagttaaa ccgaccttca gacatannn            49

<210> SEQ ID NO 46
<211> LENGTH: 41
<212> TYPE: DNA
```

<213> ORGANISM: Artificial sequence
<220> FEATURE:
<223> OTHER INFORMATION: Synthetic oligonucleotide aptamer
<220> FEATURE:
<221> NAME/KEY: misc_feature
<222> LOCATION: (1)..(17)
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t
<220> FEATURE:
<221> NAME/KEY: misc_feature
<222> LOCATION: (25)..(25)
<223> OTHER INFORMATION: n is an adenine ribonucleotide (rA)
<220> FEATURE:
<221> NAME/KEY: misc_feature
<222> LOCATION: (30)..(41)
<223> OTHER INFORMATION: n is a, c, g, or t

<400> SEQUENCE: 46
nnnnnnnnnn nnnnnnncnn ntatnggaan nnnnnnnnnn n          41

<210> SEQ ID NO 47
<211> LENGTH: 44
<212> TYPE: DNA
<213> ORGANISM: Artificial sequence
<220> FEATURE:
<223> OTHER INFORMATION: Synthetic oligonucleotide aptamer
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 47
nnnnnnnnnn nnnnncnacc tggggagta ttgcggagga aggt          44

<210> SEQ ID NO 48
<211> LENGTH: 8
<212> TYPE: DNA
<213> ORGANISM: Artificial sequence
<220> FEATURE:
<223> OTHER INFORMATION: Synthetic oligonucleotide that binds an
      adenosine aptamer
<220> FEATURE:
<221> NAME/KEY: misc_feature
<222> LOCATION: (8)..(8)
<223> OTHER INFORMATION: n is a, c, g, or t

<400> SEQUENCE: 48 cccaggtn          8

<210> SEQ ID NO 49
<211> LENGTH: 50
<212> TYPE: DNA
<213> ORGANISM: Artificial sequence
<220> FEATURE:
<223> OTHER INFORMATION: Synthetic oligonucleotide aptamer
<220> FEATURE:
<221> NAME/KEY: misc_feature
<222> LOCATION: (1)..(17)
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t
<220> FEATURE:
<221> NAME/KEY: misc_feature
<222> LOCATION: (25)..(25)

```
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (32)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t

<400> SEQUENCE: 49
nnnnnnnnnn nnnnnnncnn ntttntttnt tnnnnnnnnt tntttnttnn           50

<210> SEQ ID NO 50
<211> LENGTH: 7
<212> TYPE: DNA
<213> ORGANISM: Artificial sequence
<220> FEATURE:
<223> OTHER INFORMATION: Synthetic oligonucleotide that binds a mercury
      aptamer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (5)..(7)
<223> OTHER INFORMATION: n is a, c, g, or t

<400> SEQUENCE: 50 naaannn                                                           7

<210> SEQ ID NO 51
<211> LENGTH: 37
<212> TYPE: DNA
<213> ORGANISM: Artificial sequence
<220> FEATURE:
<223> OTHER INFORMATION: Synthetic oligonucleotide sensor
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (34)..(34)
<223> OTHER INFORMATION: n is an abasic site
<220> FEATURE:
<221> NAME/KEY: misc_feature
<222> LOCATION: (35)..(37)
<223> OTHER INFORMATION: n is a, c, g, or t

<400> SEQUENCE: 51
nnnnnnnnnn nntctccgag ccggtcgaaa tannnnn                         37

<210> SEQ ID NO 52
<211> LENGTH: 24
<212> TYPE: DNA
```

```
<213> ORGANISM: Artificial sequence
<220> FEATURE:
<223> OTHER INFORMATION: Synthetic oligonucleotide substrate of a sensor
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is an adenine ribonucleotide (rA)
<220> FEATURE:
<221> NAME/KEY: misc_feature
<222> LOCATION: (13)..(24)
<223> OTHER INFORMATION: n is a, c, g, or t

<400> SEQUENCE: 52
nnncntatng gannnnnnnn nnnn                                            24

<210> SEQ ID NO 53
<211> LENGTH: 35
<212> TYPE: DNA
<213> ORGANISM: Artificial sequence
<220> FEATURE:
<223> OTHER INFORMATION: Synthetic oligonucleotide aptamer
<220> FEATURE:
<221> NAME/KEY: misc_feature
<222> LOCATION: (1)..(8)
<223> OTHER INFORMATION: n is a, c, g, or t

<400> SEQUENCE: 53
nnnnnnnnac ctgggggagt attgcggagg aaggt                                35

<210> SEQ ID NO 54
<211> LENGTH: 12
<212> TYPE: DNA
<213> ORGANISM: Artificial sequence
<220> FEATURE:
<223> OTHER INFORMATION: Synthetic oligonucleotide that binds an
      adenosine aptamer
<220> FEATURE:
<221> NAME/KEY: misc_feature
<222> LOCATION: (4)..(4)
<223> OTHER INFORMATION: n is an abasic site
<220> FEATURE:
<221> NAME/KEY: misc_feature
<222> LOCATION: (7)..(12)
<223> OTHER INFORMATION: n is a, c, g, or t

<400> SEQUENCE: 54
ccangtnnnn nn                                                         12

<210> SEQ ID NO 55
<211> LENGTH: 29
<212> TYPE: DNA
<213> ORGANISM: Artificial sequence
<220> FEATURE:
<223> OTHER INFORMATION: Synthetic oligonucleotide sensor
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (23)..(29)
<223> OTHER INFORMATION: n is a, c, g, or t

<400> SEQUENCE: 55
```
nnnnnnrggc tagctacaac gannnnnnn                29

<210> SEQ ID NO 56
<211> LENGTH: 15
<212> TYPE: DNA
<213> ORGANISM: Artificial sequence
<220> FEATURE:
<223> OTHER INFORMATION: Synthetic oligonucleotide sensor
<220> FEATURE:
<221> NAME/KEY: misc_feature
<222> LOCATION: (1)..(7)
<223> OTHER INFORMATION: n is a, c, g, or t
<220> FEATURE:
<221> NAME/KEY: misc_feature
<222> LOCATION: (8)..(8)
<223> OTHER INFORMATION: n is an a or g ribonucleotide
<220> FEATURE:
<221> NAME/KEY: misc_feature
<222> LOCATION: (10)..(15)
<223> OTHER INFORMATION: n is a, c, g, or t

<400> SEQUENCE: 56
nnnnnnnnyn nnnnn                15

<210> SEQ ID NO 57
<211> LENGTH: 28
<212> TYPE: DNA
<213> ORGANISM: Artificial sequence
<220> FEATURE:
<223> OTHER INFORMATION: Synthetic oligonucleotide sensor
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (22)..(28)
<223> OTHER INFORMATION: n is a, c, g, or t

<400> SEQUENCE: 57
nnnnnntccg agccggtcga annnnnnn                28

<210> SEQ ID NO 58
<211> LENGTH: 15
<212> TYPE: DNA
<213> ORGANISM: Artificial sequence
<220> FEATURE:
<223> OTHER INFORMATION: Synthetic oligonucleotide sensor
<220> FEATURE:
<221> NAME/KEY: misc_feature
<222> LOCATION: (1)..(7)
<223> OTHER INFORMATION: n is a, c, g, or t
<220> FEATURE:
<221> NAME/KEY: misc_feature
<222> LOCATION: (8)..(8)
<223> OTHER INFORMATION: n is an a, g, t, u or a ribonucleotide
<220> FEATURE:
<221> NAME/KEY: misc_feature
<222> LOCATION: (10)..(15)
<223> OTHER INFORMATION: n is a, c, g, or t

<400> SEQUENCE: 58
nnnnnnnngn nnnnn                15

<210> SEQ ID NO 59
<211> LENGTH: 21
<212> TYPE: DNA
<213> ORGANISM: Artificial sequence
<220> FEATURE:
<223> OTHER INFORMATION: Synthetic oligonucleotide sensor
<220> FEATURE:
<221> NAME/KEY: misc_feature

```
<222> LOCATION: (1)..(5)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 59
nnnnnctggg ccyyyyrrrn c                                         21

<210> SEQ ID NO 60
<211> LENGTH: 14
<212> TYPE: DNA
<213> ORGANISM: Artificial sequence
<220> FEATURE:
<223> OTHER INFORMATION: Synthetic oligonucleotide sensor
<220> FEATURE:
<221> NAME/KEY: misc_feature
<222> LOCATION: (10)..(14)
<223> OTHER INFORMATION: n is a, c, g, or t

<400> SEQUENCE: 60
yyyaatacgn nnnn                                                 14

<210> SEQ ID NO 61
<211> LENGTH: 51
<212> TYPE: RNA
<213> ORGANISM: Artificial sequence
<220> FEATURE:
<223> OTHER INFORMATION: Synthetic oligonucleotide aptamer

<400> SEQUENCE: 61
augauaaacc gaugcugggc gauucuccug aaguagggga agaguuguca u        51

<210> SEQ ID NO 62
<211> LENGTH: 16
<212> TYPE: DNA
<213> ORGANISM: Artificial sequence
<220> FEATURE:
<223> OTHER INFORMATION: Synthetic oligonucleotide bridging strands that
      bind an aptamer

<400> SEQUENCE: 62
ttatcattcc attcgt                                               16

<210> SEQ ID NO 63
<211> LENGTH: 17
<212> TYPE: DNA
<213> ORGANISM: Artificial sequence
<220> FEATURE:
<223> OTHER INFORMATION: Synthetic oligonucleotide bridging strands that
      bind an aptamer

<400> SEQUENCE: 63
tttatcattc cattcgt                                              17

<210> SEQ ID NO 64
<211> LENGTH: 18
<212> TYPE: DNA
<213> ORGANISM: Artificial sequence
<220> FEATURE:
<223> OTHER INFORMATION: Synthetic oligonucleotide bridging strands that
      bind an aptamer

<400> SEQUENCE: 64
gtttatcatt ccattcgt                                             18
```

```
<210> SEQ ID NO 65
<211> LENGTH: 19
<212> TYPE: DNA
<213> ORGANISM: Artificial sequence
<220> FEATURE:
<223> OTHER INFORMATION: Synthetic oligonucleotide bridging strands that
      bind an aptamer

<400> SEQUENCE: 65
ggtttatcat tccattcgt                                                  19

<210> SEQ ID NO 66
<211> LENGTH: 19
<212> TYPE: DNA
<213> ORGANISM: Artificial sequence
<220> FEATURE:
<223> OTHER INFORMATION: Synthetic oligonucleotide bridging strands that
      bind an aptamer

<400> SEQUENCE: 66
gtttatcatt ccattcgtt                                                  19

<210> SEQ ID NO 67
<211> LENGTH: 16
<212> TYPE: DNA
<213> ORGANISM: Artificial sequence
<220> FEATURE:
<223> OTHER INFORMATION: Synthetic oligonucleotide bridging strands that
      bind an aptamer

<400> SEQUENCE: 67
tttatcattc cattcg                                                     16

<210> SEQ ID NO 68
<211> LENGTH: 43
<212> TYPE: RNA
<213> ORGANISM: Artificial sequence
<220> FEATURE:
<223> OTHER INFORMATION: Synthetic oligonucleotide aptamer

<400> SEQUENCE: 68
ucacucuaug ggcgauacca gccgaaaggc ccuuggcagc guc                       43

<210> SEQ ID NO 69
<211> LENGTH: 17
<212> TYPE: DNA
<213> ORGANISM: Artificial sequence
<220> FEATURE:
<223> OTHER INFORMATION: Synthetic oligonucleotide that binds a
      theophylline aptamer

<400> SEQUENCE: 69
attcgcccat agagtga                                                    17

<210> SEQ ID NO 70
<211> LENGTH: 43
<212> TYPE: RNA
<213> ORGANISM: Artificial sequence
<220> FEATURE:
<223> OTHER INFORMATION: Synthetic oligonucleotide aptamer

<400> SEQUENCE: 70
ucacccuaug ggcgauacca gccgaaaggc ccuuggcagc guc                       43

<210> SEQ ID NO 71
<211> LENGTH: 25
<212> TYPE: DNA
```

<213> ORGANISM: Artificial sequence
<220> FEATURE:
<223> OTHER INFORMATION: Synthetic oligonucleotide sensor

<400> SEQUENCE: 71
tcttctccga gccggtcgaa atagt                                           25

<210> SEQ ID NO 72
<211> LENGTH: 26
<212> TYPE: DNA
<213> ORGANISM: Artificial sequence
<220> FEATURE:
<223> OTHER INFORMATION: Synthetic oligonucleotide sensor

<400> SEQUENCE: 72
tcttctccga gccggtcgaa atagtg                                          26

<210> SEQ ID NO 73
<211> LENGTH: 27
<212> TYPE: DNA
<213> ORGANISM: Artificial sequence
<220> FEATURE:
<223> OTHER INFORMATION: Synthetic oligonucleotide sensor

<400> SEQUENCE: 73
ctcttctccg agccggtcga aatagtg                                         27

<210> SEQ ID NO 74
<211> LENGTH: 28
<212> TYPE: DNA
<213> ORGANISM: Artificial sequence
<220> FEATURE:
<223> OTHER INFORMATION: Synthetic oligonucleotide sensor

<400> SEQUENCE: 74
ctcttctccg agccggtcga aatagtgt                                        28

<210> SEQ ID NO 75
<211> LENGTH: 29
<212> TYPE: DNA
<213> ORGANISM: Artificial sequence
<220> FEATURE:
<223> OTHER INFORMATION: Synthetic oligonucleotide sensor

<400> SEQUENCE: 75
tctcttctcc gagccggtcg aaatagtgt                                       29

<210> SEQ ID NO 76
<211> LENGTH: 31
<212> TYPE: DNA
<213> ORGANISM: Artificial sequence
<220> FEATURE:
<223> OTHER INFORMATION: Synthetic oligonucleotide sensor

<400> SEQUENCE: 76
atctcttctc cgagccggtc gaaatagtgt g                                    31

<210> SEQ ID NO 77
<211> LENGTH: 48
<212> TYPE: DNA
<213> ORGANISM: Artificial sequence
<220> FEATURE:
<223> OTHER INFORMATION: Synthetic oligonucleotide substrate of a sensor
<220> FEATURE:
<221> NAME/KEY: misc_feature
<222> LOCATION: (4)..(4)
<223> OTHER INFORMATION: n is an abasic site

```
<220> FEATURE:
<221> NAME/KEY: misc_feature
<222> LOCATION: (24)..(24)
<223> OTHER INFORMATION: n is an adenine ribonucleotide (rA)

<400> SEQUENCE: 77
cagngcaaaa aaaaacacac tatnggaaga gatgaaaaaa atgccctg                    48

<210> SEQ ID NO 78
<211> LENGTH: 50
<212> TYPE: DNA
<213> ORGANISM: Artificial sequence
<220> FEATURE:
<223> OTHER INFORMATION: Synthetic oligonucleotide substrate of a sensor
<220> FEATURE:
<221> NAME/KEY: misc_feature
<222> LOCATION: (5)..(5)
<223> OTHER INFORMATION: n is an abasic site
<220> FEATURE:
<221> NAME/KEY: misc_feature
<222> LOCATION: (25)..(25)
<223> OTHER INFORMATION: n is an adenosine ribonucleotide

<400> SEQUENCE: 78
gcagngcaaa aaaaaacaca ctatnggaag agatgaaaaa aatgccctgc                  50

<210> SEQ ID NO 79
<211> LENGTH: 48
<212> TYPE: DNA
<213> ORGANISM: Artificial sequence
<220> FEATURE:
<223> OTHER INFORMATION: Synthetic oligonucleotide substrate
<220> FEATURE:
<221> NAME/KEY: misc_feature
<222> LOCATION: (24)..(24)
<223> OTHER INFORMATION: n is an adenosine ribonucleotide

<400> SEQUENCE: 79
cagggcaaaa aaaaacacac tatnggaaga gatgaaaaaa atgccctg                    48

<210> SEQ ID NO 80
<211> LENGTH: 52
<212> TYPE: DNA
<213> ORGANISM: Artificial sequence
<220> FEATURE:
<223> OTHER INFORMATION: Synthetic oligonucleotide aptazyme for
      adenosine

<400> SEQUENCE: 80
ctcttcagcg atctaggggg agtattgcgg aggatagcac ccatgttagt gt               52

<210> SEQ ID NO 81
<211> LENGTH: 52
<212> TYPE: DNA
<213> ORGANISM: Artificial sequence
<220> FEATURE:
<223> OTHER INFORMATION: Synthetic oligonucleotide aptazyme for
      adenosine

<400> SEQUENCE: 81
tctcttcagc gatctggggg agtattgcgg aggaagcacc catgttagtg tg               52

<210> SEQ ID NO 82
<211> LENGTH: 54
<212> TYPE: DNA
<213> ORGANISM: Artificial sequence
<220> FEATURE:
<223> OTHER INFORMATION: Synthetic oligonucleotide aptazyme for
      adenosine
```

<400> SEQUENCE: 82
tctcttcagc gatctagggg gagtattgcg gaggatagca cccatgttag tgtg    54

<210> SEQ ID NO 83
<211> LENGTH: 54
<212> TYPE: DNA
<213> ORGANISM: Artificial sequence
<220> FEATURE:
<223> OTHER INFORMATION: Synthetic oligonucleotide aptazyme for
      adenosine

<400> SEQUENCE: 83
atctcttcag cgatctgggg gagtattgcg gaggaagcac ccatgttagt gtgt    54

<210> SEQ ID NO 84
<211> LENGTH: 26
<212> TYPE: DNA
<213> ORGANISM: Artificial sequence
<220> FEATURE:
<223> OTHER INFORMATION: Synthetic oligonucleotide DNAzyme specific for
      lead

<400> SEQUENCE: 84
ctcttctccg agccggacga atagtg    26

<210> SEQ ID NO 85
<211> LENGTH: 27
<212> TYPE: DNA
<213> ORGANISM: Artificial sequence
<220> FEATURE:
<223> OTHER INFORMATION: Synthetic oligonucleotide DNAzyme specific for
      lead

<400> SEQUENCE: 85
ctcttctgtc agcgacacga aatagtg    27

<210> SEQ ID NO 86
<211> LENGTH: 27
<212> TYPE: DNA
<213> ORGANISM: Artificial sequence
<220> FEATURE:
<223> OTHER INFORMATION: Synthetic oligonucleotide DNAzyme specific for
      lead

<400> SEQUENCE: 86
ctcttccccg agccggtcga aatagtg    27

<210> SEQ ID NO 87
<211> LENGTH: 26
<212> TYPE: DNA
<213> ORGANISM: Artificial sequence
<220> FEATURE:
<223> OTHER INFORMATION: Synthetic oligonucleotide DNAzyme specific for
      lead

<400> SEQUENCE: 87
ctcttctccg agccggtcga atagtg    26

<210> SEQ ID NO 88
<211> LENGTH: 26
<212> TYPE: DNA
<213> ORGANISM: Artificial sequence
<220> FEATURE:
<223> OTHER INFORMATION: Synthetic oligonucleotide DNAzyme specific for
      lead

```
<400> SEQUENCE: 88
ctcttctccg agccggcgaa atagtg                                          26

<210> SEQ ID NO 89
<211> LENGTH: 29
<212> TYPE: DNA
<213> ORGANISM: Artificial sequence
<220> FEATURE:
<223> OTHER INFORMATION: Synthetic oligonucleotide DNAzyme specific for
      lead

<400> SEQUENCE: 89
ctcttctccg gagcccggtc gaaatagtg                                       29

<210> SEQ ID NO 90
<211> LENGTH: 27
<212> TYPE: DNA
<213> ORGANISM: Artificial sequence
<220> FEATURE:
<223> OTHER INFORMATION: Synthetic oligonucleotide DNAzyme specific for
      lead

<400> SEQUENCE: 90
ctcttctcag agcctgtcga aatagtg                                         27

<210> SEQ ID NO 91
<211> LENGTH: 28
<212> TYPE: DNA
<213> ORGANISM: Artificial sequence
<220> FEATURE:
<223> OTHER INFORMATION: Synthetic oligonucleotide DNAzyme specific for
      lead

<400> SEQUENCE: 91
ctcttctccg aagccggtcg aaatagtg                                        28

<210> SEQ ID NO 92
<211> LENGTH: 27
<212> TYPE: DNA
<213> ORGANISM: Artificial sequence
<220> FEATURE:
<223> OTHER INFORMATION: Synthetic oligonucleotide DNAzyme specific for
      lead

<400> SEQUENCE: 92
ctcttctccg cgacggtcga aatagtg                                         27

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide substrate for DNA for
      gel electrophoresis
<220> FEATURE:
<221> NAME/KEY: misc_feature
<222> LOCATION: (10)..(10)
<223> OTHER INFORMATION: n is an adenosine ribonucleotide

<400> SEQUENCE: 93
acacactatn ggaagagatg                                                 20

<210> SEQ ID NO 94
<211> LENGTH: 50
<212> TYPE: DNA
<213> ORGANISM: Artificial Sequence
<220> FEATURE:
```

```
<223> OTHER INFORMATION: Synthetic oligonucleotide sensor
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (6)..(25)
<223> OTHER INFORMATION: n is a, c, g, or t
<220> FEATURE:
<221> NAME/KEY: misc_feature
<222> LOCATION: (26)..(26)
<223> OTHER INFORMATION: n is an adenine ribonucleotide (rA)
<220> FEATURE:
<221> NAME/KEY: misc_feature
<222> LOCATION: (27)..(45)
<223> OTHER INFORMATION: n is a, c, g, or t
<220> FEATURE:
<221> NAME/KEY: misc_feature
<222> LOCATION: (46)..(46)
<223> OTHER INFORMATION: n is an abasic site
<220> FEATURE:
<221> NAME/KEY: misc_feature
<222> LOCATION: (47)..(50)
<223> OTHER INFORMATION: n is a, c, g, or t

<400> SEQUENCE: 94
nnnncnnnnn nnnnnnnnnn nnnnnnnnnn nnnnnnnnnn nnnnnnnnnn        50

<210> SEQ ID NO 95
<211> LENGTH: 27
<212> TYPE: DNA
<213> ORGANISM: Artificial Sequence
<220> FEATURE:
<223> OTHER INFORMATION: Synthetic oligonucleotide sensor
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (21)..(27)
<223> OTHER INFORMATION: n is a, c, g, or t

<400> SEQUENCE: 95
nnnnnnaagc tggccgagcc nnnnnnn                                 27

<210> SEQ ID NO 96
<211> LENGTH: 51
<212> TYPE: DNA
<213> ORGANISM: Artificial Sequence
<220> FEATURE:
<223> OTHER INFORMATION: Synthetic oligonucleotide sensor
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (6)..(25)
<223> OTHER INFORMATION: n is a, c, g, or t
<220> FEATURE:
<221> NAME/KEY: misc_feature
<222> LOCATION: (26)..(26)
<223> OTHER INFORMATION: n is an adenine ribonucleotide (rA)
<220> FEATURE:
<221> NAME/KEY: misc_feature
<222> LOCATION: (27)..(46)
<223> OTHER INFORMATION: n is a, c, g, or t
<220> FEATURE:
<221> NAME/KEY: misc_feature
<222> LOCATION: (47)..(47)
<223> OTHER INFORMATION: n is an abasic site
<220> FEATURE:
<221> NAME/KEY: misc_feature
```

```
<222> LOCATION: (48)..(51)
<223> OTHER INFORMATION: n is a, c, g, or t

<400> SEQUENCE: 96
nnnncnnnnn nnnnnnnnnn nnnnnnnnnn nnnnnnnnnn nnnnnnnnnn n         51

<210> SEQ ID NO 97
<211> LENGTH: 51
<212> TYPE: DNA
<213> ORGANISM: Artificial Sequence
<220> FEATURE:
<223> OTHER INFORMATION: Synthetic oligonucleotide sensor
<220> FEATURE:
<221> NAME/KEY: misc_feature
<222> LOCATION: (1)..(7)
<223> OTHER INFORMATION: n is a, c, g, or t
<220> FEATURE:
<221> NAME/KEY: misc_feature
<222> LOCATION: (46)..(51)
<223> OTHER INFORMATION: n is a, c, g, or t

<400> SEQUENCE: 97
nnnnnnntgt acccacgaag gaggcgttat gaggggtct agcgannnnn n           51
```